US010087228B2

(12) United States Patent
Erickson

(10) Patent No.: US 10,087,228 B2
(45) Date of Patent: Oct. 2, 2018

(54) CHIMERIC LEPTIN POLYPEPTIDE AND METHOD OF USING THE SAME

(71) Applicant: Aegerion Pharmaceuticals, Inc., Cambridge, MA (US)

(72) Inventor: Mary Erickson, San Diego, CA (US)

(73) Assignee: Aegerion Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/703,523

(22) Filed: May 4, 2015

(65) Prior Publication Data

US 2016/0083446 A1  Mar. 24, 2016

Related U.S. Application Data

(63) Continuation of application No. 13/852,521, filed on Mar. 28, 2013, which is a continuation of application No. PCT/US2011/053774, filed on Sep. 28, 2011.

(60) Provisional application No. 61/422,091, filed on Dec. 10, 2010, provisional application No. 61/387,402, filed on Sep. 28, 2010.

(51) Int. Cl.
*A61K 38/22* (2006.01)
*C07K 14/575* (2006.01)
*C07K 14/00* (2006.01)
*A61K 38/00* (2006.01)

(52) U.S. Cl.
CPC .......... *C07K 14/5759* (2013.01); *C07K 14/00* (2013.01); *C07K 14/575* (2013.01); *A61K 38/00* (2013.01); *A61K 38/2264* (2013.01); *C07K 2319/33* (2013.01)

(58) Field of Classification Search
CPC .................................................. C07K 14/575
See application file for complete search history.

(56) References Cited

U.S. PATENT DOCUMENTS

| | | | |
|---|---|---|---|
| 4,179,337 A | 12/1979 | Davis et al. | |
| 5,552,523 A | 9/1996 | Basinski et al. | |
| 5,554,727 A | 9/1996 | Basinski et al. | |
| 5,559,208 A | 9/1996 | Basinski et al. | |
| 5,580,954 A | 12/1996 | DiMarchi et al. | |
| 5,594,101 A | 1/1997 | Becker et al. | |
| 5,686,411 A | 11/1997 | Gaeta et al. | |
| 5,691,309 A | 11/1997 | Basinski et al. | |
| 5,756,461 A | 5/1998 | Stephens | |
| 5,824,778 A | 10/1998 | Ishikawa et al. | |
| 5,824,784 A | 10/1998 | Kinsller et al. | |
| 5,851,995 A | 12/1998 | Basinski et al. | |
| 6,309,853 B1 | 10/2001 | Friedman et al. | |
| 6,319,685 B1 | 11/2001 | Gilligan et al. | |
| 6,326,468 B1 | 12/2001 | Canne et al. | |
| 6,475,984 B2* | 11/2002 | Kirwin | A61K 9/5015 514/4.8 |
| 6,872,700 B1 | 3/2005 | Young et al. | |
| 7,183,254 B2 | 2/2007 | DePaoli et al. | |
| 2006/0030530 A1 | 2/2006 | Yen et al. | |
| 2007/0020284 A1 | 1/2007 | Mann et al. | |
| 2007/0238669 A1 | 10/2007 | Haque et al. | |
| 2008/0176804 A1 | 7/2008 | Mack et al. | |
| 2008/0207512 A1 | 8/2008 | Roth et al. | |
| 2008/0274952 A1 | 11/2008 | Soares et al. | |
| 2010/0104588 A1 | 4/2010 | Dennis | |
| 2010/0184641 A1 | 7/2010 | Dorwald et al. | |
| 2013/0274182 A1 | 10/2013 | Erickson et al. | |

FOREIGN PATENT DOCUMENTS

| | | |
|---|---|---|
| EP | 0 401 384 A1 | 2/1990 |
| EP | 0725079 | 8/1996 |
| WO | 83/004053 A1 | 11/1983 |
| WO | 96/005309 A2 | 2/1996 |
| WO | 96/23517 A1 | 8/1996 |
| WO | 97/02004 A2 | 1/1997 |
| WO | 98/12224 A1 | 3/1998 |
| WO | 98/28427 A1 | 7/1998 |
| WO | 98/41222 | 9/1998 |
| WO | 98/42861 | 10/1998 |
| WO | 98/55139 A1 | 12/1998 |
| WO | 2002/004488 A2 | 1/2002 |
| WO | 2004/039832 A2 | 5/2004 |
| WO | 2004/039853 A1 | 5/2004 |
| WO | 05/027978 | 3/2005 |
| WO | 2006/083254 A1 | 8/2006 |
| WO | 2007/114838 A1 | 10/2007 |

(Continued)

OTHER PUBLICATIONS

Hall et al 2006, Am. J. Physiology, 289: R545-R553.*
Rohner-Jearnrenaud et al. The New Eng. J. Med., 334: 324-325, 1996.*
Grasso et al. Endocrinol. 138: 1413-1418, 1997.*
International Search Report dated Apr. 25, 2012 for PCT Application No. PCT/US11/53786 , 4 pages.
Dennis et al., "Albumin Binding as a General Strategy for Improving the Pharmacokinetics of Proteins", *JBC*, 2002, vol. 277, No. 38, pp. 35035-35043.
Ricci et al., "Mutational Approach to Improve Physical Stability of Protein Therapeutics Susceptible to Aggregation", *Misbehaving Proteins: Protein (Mis)Folding, Aggression, and Stability*, 2006, Murphy et al. Eds, New York. Springer. pp. 331-350.

(Continued)

*Primary Examiner* — Gyan Chandra
(74) *Attorney, Agent, or Firm* — Haug Partners LLP

(57) ABSTRACT

The disclosure provides chimeric polypeptides and nucleic acid molecules encoding chimeric polypeptides. Also provided are pharmaceutical compositions and methods of treatment for diseases and disorders including lipodystrophy, dyslipidemia, hyperlipidemia, overweight, obesity, hypothalamic amenorrhea, Alzheimer's disease, leptin deficiency, fatty liver disease or diabetes (including type I and type II). Additional diseases and disorders which can be treated by the compounds and methods described herein include nonalcoholic steatohepatitis (NASH) and nonalcoholic fatty liver disease (NAFLD), metabolic syndrome X and Huntington's Disease.

7 Claims, 4 Drawing Sheets

Specification includes a Sequence Listing.

(56) References Cited

FOREIGN PATENT DOCUMENTS

| WO | 2007/139941 A2 | 12/2007 |
|---|---|---|
| WO | 2007/140284 A2 | 12/2007 |
| WO | 2008/082274 A1 | 7/2008 |
| WO | 2009/011544 A2 | 1/2009 |
| WO | 2009/016043 A2 | 2/2009 |
| WO | 09/042922 | 4/2009 |
| WO | 2009/064298 A1 | 5/2009 |
| WO | 2009/100255 A2 | 8/2009 |
| WO | 2009/149379 A2 | 12/2009 |
| WO | 13/009539 | 1/2013 |

OTHER PUBLICATIONS

Jonsson et al., "Engineering of a femtomolar affinity binding protein to human serum albumin", *Protein Eng. Design & Selection*, 2008, vol. 221, pp. 515-527.
He et al., "Atomic structure and chemistry of human serum albumin", *Nature*, 1992, vol. 358, pp. 358:209.
Sheffield, "Modification of Clearance of Therapeutic and Potentially Therapeutic Proteins", 2001, *Curr. Drug Targets—Cardiovascular & Hematological Disorders*, 2001, vol. 1, pp. 1-22.
Murakami et al., "The role of neuropeptide Y in the antiobesity action of the obese gene product", *Biochem. Biophys. Res. Comm.*, 1995, vol. 209, pp. 944-952.
Malik et al., "Polyethylene Glycol (PEG)-modified Granulocyte-Macrophage Colony-stimulating Factor (GM-CSF) with Conserved Biological Activity", *Exp. Hematol*, 1992, vol. 20, pp. 1028-1035.
Tenenbaum, "Leptin's Legacy", *HHMI Bulletin*, 2003, pp. 25-27.
Chicurel, "Whatever happened to leptin", *Nature*, 2000, vol. 404, pp. 538-540.
Scarpace et al., "Leptin resistance exacerbate diet-induced obesity and is associated with diminished maximal leptin signaling capacity in rats", *Diabetalogia*, 2005, vol. 48, pp. 1075-1083.
Bays et al., "Current and Investigational Antiobesity Agents and Obesity Therapeutic Treatment Targets", *Obesity Research*, 2004, vol. 12, No. 8, pp. 1197-1211.
International Search Report dated Feb. 23, 2012 for PCT Application No. PCT/US11/53774, 4 pages.
UniProtKB Direct Submission Q706Do. LEP_HALGR (Jul. 10, 2007) Retrieved from the Internet Oct. 7, 2013, http://www.uniprot.org/uniprot/Q706DO.txt?version=22>.
Search Report dated Aug. 15, 2013 for Eurasian Application No. 201390497, 4 pages (Including English Summary).
Johansson et al., "Structure, Specificity, and Mode of Interaction for Bacterial Albumin-binding Modules", Journal of Biological Chemistry, 2002, 277:8114-8120.
Supplementary European Search Report from the counterpart European Patent Application No. 11833075 dated Jun. 4, 2014.
Extended European Search Report from the counterpart European Patent Application No. 11833080 dated Jun. 5, 2014.
J. A. Hammond: "Molecular cloning and expression of leptin in gray and harbor seal blubber, bone marrow, and lung and its potential role in marine mammal respiratory physiology", American Journal of Physiology. Regulatory, Integrative and Comparative Physiology, vol. 289, No. 2, Aug. 2005, pp. R545-R553.

\* cited by examiner

SEQUENCE LISTING

```
<160> NUMBER OF SEQ ID NOS: 164

<210> SEQ ID NO 1
<211> LENGTH: 146
<212> TYPE: PRT
<213> ORGANISM: Unknown
<220> FEATURE:
<223> OTHER INFORMATION: Leptin of unknown murine species
<220> FEATURE:
<221> NAME/KEY: MOD_RES
<222> LOCATION: (28)..(28)
<223> OTHER INFORMATION: May or may not be present

<400> SEQUENCE: 1

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Gln Ala Ser Gly Leu Glu Thr Leu Glu Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Gln Gln Leu Asp Leu Ser Pro
    130                 135                 140

Gly Cys
145

<210> SEQ ID NO 2
<211> LENGTH: 146
<212> TYPE: PRT
<213> ORGANISM: Unknown
<220> FEATURE:
<223> OTHER INFORMATION: Leptin of unknown murine species

<400> SEQUENCE: 2

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30
```

Lys Gln Arg Val Thr Gly Leu Asp Phe Ile Pro Gly Leu His Pro Ile
                35                  40                  45

Leu Ser Leu Ser Lys Met Asp Gln Thr Leu Ala Val Tyr Gln Gln Val
 50                  55                  60

Leu Thr Ser Leu Pro Ser Gln Asn Val Leu Gln Ile Ala Asn Asp Leu
 65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
                100                 105                 110

Val Leu Glu Ala Ser Leu Tyr Ser Thr Glu Val Val Ala Leu Ser Arg
                115                 120                 125

Leu Gln Gly Ser Leu Gln Asp Ile Leu Gln Gln Leu Asp Val Ser Pro
                130                 135                 140

Glu Cys
145

<210> SEQ ID NO 3
<211> LENGTH: 145
<212> TYPE: PRT
<213> ORGANISM: Unknown
<220> FEATURE:
<223> OTHER INFORMATION: Leptin of unknown murine species

<400> SEQUENCE: 3

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Ser Val Ser Ala Lys
                20                  25                  30

Gln Arg Val Thr Gly Leu Asp Phe Ile Pro Gly Leu His Pro Ile Leu
                35                  40                  45

Ser Leu Ser Lys Met Asp Gln Thr Leu Ala Val Tyr Gln Gln Val Leu
 50                  55                  60

Thr Ser Leu Pro Ser Gln Asn Val Leu Gln Ile Ala Asn Asp Leu Glu
65                   70                  75                  80

Asn Leu Arg Asp Leu Leu His Leu Leu Ala Phe Ser Lys Ser Cys Ser
                85                  90                  95

Leu Pro Gln Thr Ser Gly Leu Gln Lys Pro Glu Ser Leu Asp Gly Val
                100                 105                 110

Leu Glu Ala Ser Leu Tyr Ser Thr Glu Val Val Ala Leu Ser Arg Leu
                115                 120                 125

Gln Gly Ser Leu Gln Asp Ile Leu Gln Gln Leu Asp Val Ser Pro Glu
                130                 135                 140

Cys
145

<210> SEQ ID NO 4
<211> LENGTH: 147
<212> TYPE: PRT
<213> ORGANISM: Unknown
<220> FEATURE:
<223> OTHER INFORMATION: Leptin of unknown murine species
<220> FEATURE:
<221> NAME/KEY: MOD_RES
<222> LOCATION: (29)..(29)
<223> OTHER INFORMATION: May or may not be present

<400> SEQUENCE: 4

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys
145

<210> SEQ ID NO 5
<211> LENGTH: 147
<212> TYPE: PRT
<213> ORGANISM: Unknown
<220> FEATURE:
<223> OTHER INFORMATION: Leptin of unknown murine species

<400> SEQUENCE: 5

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ala Lys Gln Arg Val Thr Gly Leu Asp Phe Ile Pro Gly Leu His Pro
        35                  40                  45

Ile Leu Ser Leu Ser Lys Met Asp Gln Thr Leu Ala Val Tyr Gln Gln
50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

<210> SEQ ID NO 6
<211> LENGTH: 146
<212> TYPE: PRT
<213> ORGANISM: Unknown
<220> FEATURE:
<223> OTHER INFORMATION: Leptin of unknown murine species

<400> SEQUENCE: 6
```

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Ser Val Ser Ala
                20                  25                  30

Lys Gln Arg Val Thr Gly Leu Asp Phe Ile Pro Gly Leu His Pro Ile
            35                  40                  45

Leu Ser Leu Ser Lys Met Asp Gln Thr Leu Ala Val Tyr Gln Gln Val
    50                  55                  60

Leu Thr Ser Leu Pro Ser Gln Asn Val Leu Gln Ile Ala Asn Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Val Ser Pro
    130                 135                 140

Glu Cys
145

<210> SEQ ID NO 7
<211> LENGTH: 146
<212> TYPE: PRT
<213> ORGANISM: Unknown
<220> FEATURE:
<223> OTHER INFORMATION: Leptin from unknown Sus species

<400> SEQUENCE: 7

Val Pro Ile Trp Arg Val Gln Asp Asp Thr Lys Thr Leu Ile Lys Thr
1               5                   10                  15

Ile Val Thr Arg Ile Ser Asp Ile Ser His Met Gln Ser Val Ser Ser
                20                  25                  30

Lys Gln Arg Val Thr Gly Leu Asp Phe Ile Pro Gly Leu His Pro Val
            35                  40                  45

Leu Ser Leu Ser Lys Met Asp Gln Thr Leu Ala Ile Tyr Gln Gln Ile
    50                  55                  60

Leu Thr Ser Leu Pro Ser Arg Asn Val Ile Gln Ile Ser Asn Asp Leu
65                  70                  75                  80

Glu Asn Leu Arg Asp Leu Leu His Leu Leu Ala Ser Ser Lys Ser Cys
                85                  90                  95

Pro Leu Pro Gln Ala Arg Ala Leu Glu Thr Leu Glu Ser Leu Gly Gly
            100                 105                 110

Val Leu Glu Ala Ser Leu Tyr Ser Thr Glu Val Val Ala Leu Ser Arg
        115                 120                 125

Leu Gln Gly Ala Leu Gln Asp Met Leu Arg Gln Leu Asp Leu Ser Pro
    130                 135                 140

Gly Cys
145

<210> SEQ ID NO 8
<211> LENGTH: 147
<212> TYPE: PRT
<213> ORGANISM: Unknown
<220> FEATURE:
<223> OTHER INFORMATION: Leptin from unknown Sus species
```

-continued

<400> SEQUENCE: 8

Met Val Pro Ile Trp Arg Val Gln Asp Asp Thr Lys Thr Leu Ile Lys
1               5                   10                  15

Thr Ile Val Thr Arg Ile Ser Asp Ile Ser His Met Gln Ser Val Ser
            20                  25                  30

Ser Lys Gln Arg Val Thr Gly Leu Asp Phe Ile Pro Gly Leu His Pro
        35                  40                  45

Val Leu Ser Leu Ser Lys Met Asp Gln Thr Leu Ala Ile Tyr Gln Gln
    50                  55                  60

Ile Leu Thr Ser Leu Pro Ser Arg Asn Val Ile Gln Ile Ser Asn Asp
65                  70                  75                  80

Leu Glu Asn Leu Arg Asp Leu Leu His Leu Leu Ala Ser Ser Lys Ser
                85                  90                  95

Cys Pro Leu Pro Gln Ala Arg Ala Leu Glu Thr Leu Glu Ser Leu Gly
            100                 105                 110

Gly Val Leu Glu Ala Ser Leu Tyr Ser Thr Glu Val Val Ala Leu Ser
        115                 120                 125

Arg Leu Gln Gly Ala Leu Gln Asp Met Leu Arg Gln Leu Asp Leu Ser
    130                 135                 140

Pro Gly Cys
145

<210> SEQ ID NO 9
<211> LENGTH: 146
<212> TYPE: PRT
<213> ORGANISM: Unknown
<220> FEATURE:
<223> OTHER INFORMATION: Leptin from unknown Bos species
<220> FEATURE:
<221> NAME/KEY: MOD_RES
<222> LOCATION: (28)..(28)
<223> OTHER INFORMATION: May or may not be present

<400> SEQUENCE: 9

Val Pro Ile Cys Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Thr Ser Leu Pro Ser Arg Asn Val Val Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 10
<211> LENGTH: 147

```
<212> TYPE: PRT
<213> ORGANISM: Unknown
<220> FEATURE:
<223> OTHER INFORMATION: Leptin from unknown Bos species
<220> FEATURE:
<221> NAME/KEY: MOD_RES
<222> LOCATION: (29)..(29)
<223> OTHER INFORMATION: May or may not be present

<400> SEQUENCE: 10

Met Val Pro Ile Cys Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Leu Leu Ser Leu Ser Lys Met Asp Gln Thr Leu Ala Ile Tyr Gln Gln
    50                  55                  60

Ile Leu Thr Ser Leu Pro Ser Arg Asn Val Val Gln Ile Ser Asn Asp
65                  70                  75                  80

Leu Glu Asn Leu Arg Asp Leu Leu His Leu Leu Ala Ala Ser Lys Ser
                85                  90                  95

Cys Pro Leu Pro Gln Val Arg Ala Leu Glu Ser Leu Glu Ser Leu Gly
            100                 105                 110

Val Val Leu Glu Ala Ser Leu Tyr Ser Thr Glu Val Val Ala Leu Ser
        115                 120                 125

Arg Leu Gln Gly Ser Leu Gln Asp Met Leu Arg Gln Leu Asp Leu Ser
    130                 135                 140

Pro Gly Cys
145

<210> SEQ ID NO 11
<211> LENGTH: 167
<212> TYPE: PRT
<213> ORGANISM: Homo sapiens

<400> SEQUENCE: 11

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160
```

Leu Asp Leu Ser Pro Gly Cys
                165

<210> SEQ ID NO 12
<211> LENGTH: 146
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Thr or Ala
<220> FEATURE:
<221> NAME/KEY: MOD_RES
<222> LOCATION: (28)..(28)
<223> OTHER INFORMATION: May or may not be present

<400> SEQUENCE: 12

Val Pro Ile Gln Lys Val Gln Asp Asp Thr Lys Thr Leu Ile Lys Thr
1               5                   10                  15

Ile Val Thr Arg Ile Asn Asp Ile Ser His Xaa Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 13
<211> LENGTH: 147
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Thr or Ala
<220> FEATURE:
<221> NAME/KEY: MOD_RES
<222> LOCATION: (29)..(29)
<223> OTHER INFORMATION: May or may not be present

<400> SEQUENCE: 13

Met Val Pro Ile Gln Lys Val Gln Asp Asp Thr Lys Thr Leu Ile Lys
1               5                   10                  15

Thr Ile Val Thr Arg Ile Asn Asp Ile Ser His Xaa Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

```
Leu Glu Asn Leu Arg Asp Leu Leu His Val Leu Ala Phe Ser Lys Ser
                85                  90                  95
Cys His Leu Pro Trp Ala Ser Gly Leu Glu Thr Leu Asp Ser Leu Gly
            100                 105                 110
Gly Val Leu Glu Ala Ser Gly Tyr Ser Thr Glu Val Val Ala Leu Ser
        115                 120                 125
Arg Leu Gln Gly Ser Leu Gln Asp Met Leu Trp Gln Leu Asp Leu Ser
    130                 135                 140
Pro Gly Cys
145

<210> SEQ ID NO 14
<211> LENGTH: 146
<212> TYPE: PRT
<213> ORGANISM: Macaca mulatta

<400> SEQUENCE: 14

Val Pro Ile Gln Lys Val Gln Ser Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Arg Val Thr Gly Leu Asp Phe Ile Pro Gly Leu His Pro Val
        35                  40                  45
Leu Thr Leu Ser Gln Met Asp Gln Thr Leu Ala Ile Tyr Gln Gln Ile
    50                  55                  60
Leu Ile Asn Leu Pro Ser Arg Asn Val Ile Gln Ile Ser Asn Asp Leu
65                  70                  75                  80
Glu Asn Leu Arg Asp Leu Leu His Leu Leu Ala Phe Ser Lys Ser Cys
                85                  90                  95
His Leu Pro Leu Ala Ser Gly Leu Glu Thr Leu Glu Ser Leu Gly Asp
            100                 105                 110
Val Leu Glu Ala Ser Leu Tyr Ser Thr Glu Val Val Ala Leu Ser Arg
        115                 120                 125
Leu Gln Gly Ser Leu Gln Asp Met Leu Trp Gln Leu Asp Leu Ser Pro
    130                 135                 140
Gly Cys
145

<210> SEQ ID NO 15
<211> LENGTH: 147
<212> TYPE: PRT
<213> ORGANISM: Macaca mulatta

<400> SEQUENCE: 15

Met Val Pro Ile Gln Lys Val Gln Ser Asp Thr Lys Thr Leu Ile Lys
1               5                   10                  15
Thr Ile Val Thr Arg Ile Asn Asp Ile Ser His Thr Gln Ser Val Ser
            20                  25                  30
Ser Lys Gln Arg Val Thr Gly Leu Asp Phe Ile Pro Gly Leu His Pro
        35                  40                  45
Val Leu Thr Leu Ser Gln Met Asp Gln Thr Leu Ala Ile Tyr Gln Gln
    50                  55                  60
Ile Leu Ile Asn Leu Pro Ser Arg Asn Val Ile Gln Ile Ser Asn Asp
65                  70                  75                  80
Leu Glu Asn Leu Arg Asp Leu Leu His Leu Leu Ala Phe Ser Lys Ser
                85                  90                  95
```

```
Cys His Leu Pro Leu Ala Ser Gly Leu Glu Thr Leu Glu Ser Leu Gly
            100                 105                 110

Asp Val Leu Glu Ala Ser Leu Tyr Ser Thr Glu Val Ala Leu Ser
        115                 120                 125

Arg Leu Gln Gly Ser Leu Gln Asp Met Leu Trp Gln Leu Asp Leu Ser
130                 135                 140

Pro Gly Cys
145

<210> SEQ ID NO 16
<211> LENGTH: 146
<212> TYPE: PRT
<213> ORGANISM: Unknown
<220> FEATURE:
<223> OTHER INFORMATION: Leptin from unknown Rattus species

<400> SEQUENCE: 16

Val Pro Ile His Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Arg Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Ile
50                  55                  60

Leu Thr Ser Leu Pro Ser Gln Asn Val Leu Gln Ile Ala His Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Arg Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Leu Ser Pro
130                 135                 140

Glu Cys
145

<210> SEQ ID NO 17
<211> LENGTH: 147
<212> TYPE: PRT
<213> ORGANISM: Unknown
<220> FEATURE:
<223> OTHER INFORMATION: Leptin from unknown Rattus species

<400> SEQUENCE: 17

Met Val Pro Ile His Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ala Arg Gln Arg Val Thr Gly Leu Asp Phe Ile Pro Gly Leu His Pro
        35                  40                  45

Ile Leu Ser Leu Ser Lys Met Asp Gln Thr Leu Ala Val Tyr Gln Gln
50                  55                  60

Ile Leu Thr Ser Leu Pro Ser Gln Asn Val Leu Gln Ile Ala His Asp
65                  70                  75                  80

Leu Glu Asn Leu Arg Asp Leu Leu His Leu Leu Ala Phe Ser Lys Ser
```

```
                     85                  90                  95

Cys Ser Leu Pro Gln Thr Arg Gly Leu Gln Lys Pro Glu Ser Leu Asp
                100                 105                 110

Gly Val Leu Glu Ala Ser Leu Tyr Ser Thr Glu Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 18
<211> LENGTH: 145
<212> TYPE: PRT
<213> ORGANISM: Ornithorhynchus anatinus

<400> SEQUENCE: 18

Ile Ser Ile Glu Lys Ile Gln Ala Asp Thr Lys Thr Leu Thr Lys Thr
1               5                   10                  15

Ile Ile Thr Arg Ile Ile Gln Leu Ser Thr Gln Asn Gly Val Ser Thr
            20                  25                  30

Asp Gln Arg Val Ser Gly Leu Asp Phe Ile Pro Gly Asn Gln Gln Phe
        35                  40                  45

Gln Asn Leu Ala Asp Met Asp Gln Thr Leu Ala Val Tyr Gln Gln Ile
    50                  55                  60

Leu Ser Ser Leu Pro Met Pro Asp Arg Thr Gln Ile Ser Asn Asp Leu
65                  70                  75                  80

Glu Asn Leu Arg Ser Leu Phe Ala Leu Leu Ala Thr Leu Lys Asn Cys
                85                  90                  95

Pro Phe Thr Arg Ser Asp Gly Leu Asp Thr Met Glu Ile Trp Gly Gly
                100                 105                 110

Ile Val Glu Glu Ser Leu Tyr Ser Thr Glu Val Val Thr Leu Asp Arg
            115                 120                 125

Leu Arg Lys Ser Leu Lys Asn Ile Glu Lys Gln Leu Asp His Ile Gln
        130                 135                 140

Gly
145

<210> SEQ ID NO 19
<211> LENGTH: 166
<212> TYPE: PRT
<213> ORGANISM: Ornithorhynchus anatinus

<400> SEQUENCE: 19

Met Arg Cys Ile Leu Leu Tyr Gly Phe Leu Cys Val Trp Gln His Leu
1               5                   10                  15

Tyr Tyr Ser His Pro Ile Ser Ile Glu Lys Ile Gln Ala Asp Thr Lys
            20                  25                  30

Thr Leu Thr Lys Thr Ile Ile Thr Arg Ile Ile Gln Leu Ser Thr Gln
        35                  40                  45

Asn Gly Val Ser Thr Asp Gln Arg Val Ser Gly Leu Asp Phe Ile Pro
    50                  55                  60

Gly Asn Gln Gln Phe Gln Asn Leu Ala Asp Met Asp Gln Thr Leu Ala
65                  70                  75                  80

Val Tyr Gln Gln Ile Leu Ser Ser Leu Pro Met Pro Asp Arg Thr Gln
                85                  90                  95

Ile Ser Asn Asp Leu Glu Asn Leu Arg Ser Leu Phe Ala Leu Leu Ala
```

```
                 100                 105                 110
Thr Leu Lys Asn Cys Pro Phe Thr Arg Ser Asp Gly Leu Asp Thr Met
        115                 120                 125

Glu Ile Trp Gly Gly Ile Val Glu Glu Ser Leu Tyr Ser Thr Glu Val
        130                 135                 140

Val Thr Leu Asp Arg Leu Arg Lys Ser Leu Lys Asn Ile Glu Lys Gln
145                 150                 155                 160

Leu Asp His Ile Gln Gly
                165

<210> SEQ ID NO 20
<211> LENGTH: 146
<212> TYPE: PRT
<213> ORGANISM: Homo sapiens

<400> SEQUENCE: 20

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 21
<211> LENGTH: 146
<212> TYPE: PRT
<213> ORGANISM: Homo sapiens

<400> SEQUENCE: 21

Val Pro Ile Gln Lys Val Gln Asp Asp Thr Lys Thr Leu Ile Lys Thr
1               5                   10                  15

Ile Val Thr Arg Ile Asn Asp Ile Ser His Ala Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
```

```
                    100                 105                 110
Val Leu Glu Ala Ser Gly Tyr Ser Thr Glu Val Val Ala Leu Ser Arg
                115                 120                 125

Leu Gln Gly Ser Leu Gln Asp Met Leu Trp Gln Leu Asp Leu Ser Pro
        130                 135                 140

Gly Cys
145

<210> SEQ ID NO 22
<211> LENGTH: 145
<212> TYPE: PRT
<213> ORGANISM: Homo sapiens

<400> SEQUENCE: 22

Val Pro Ile Gln Lys Val Gln Asp Asp Thr Lys Thr Leu Ile Lys Thr
1               5                   10                  15

Ile Val Thr Arg Ile Asn Asp Ile Ser His Thr Ser Val Ser Ser Lys
                20                  25                  30

Gln Lys Val Thr Gly Leu Asp Phe Ile Pro Gly Leu His Pro Ile Leu
            35                  40                  45

Thr Leu Ser Lys Met Asp Gln Thr Leu Ala Val Tyr Gln Gln Ile Leu
        50                  55                  60

Thr Ser Met Pro Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
                100                 105                 110

Leu Glu Ala Ser Gly Tyr Ser Thr Glu Val Val Ala Leu Ser Arg Leu
            115                 120                 125

Gln Gly Ser Leu Gln Asp Met Leu Trp Gln Leu Asp Leu Ser Pro Gly
        130                 135                 140

Cys
145

<210> SEQ ID NO 23
<211> LENGTH: 145
<212> TYPE: PRT
<213> ORGANISM: Homo sapiens

<400> SEQUENCE: 23

Val Pro Ile Gln Lys Val Gln Asp Asp Thr Lys Thr Leu Ile Lys Thr
1               5                   10                  15

Ile Val Thr Arg Ile Asn Asp Ile Ser His Ala Ser Val Ser Ser Lys
                20                  25                  30

Gln Lys Val Thr Gly Leu Asp Phe Ile Pro Gly Leu His Pro Ile Leu
            35                  40                  45

Thr Leu Ser Lys Met Asp Gln Thr Leu Ala Val Tyr Gln Gln Ile Leu
        50                  55                  60

Thr Ser Met Pro Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
                100                 105                 110

Leu Glu Ala Ser Gly Tyr Ser Thr Glu Val Val Ala Leu Ser Arg Leu
```

```
                    115                 120                 125

Gln Gly Ser Leu Gln Asp Met Leu Trp Gln Leu Asp Leu Ser Pro Gly
        130                 135                 140

Cys
145

<210> SEQ ID NO 24
<211> LENGTH: 147
<212> TYPE: PRT
<213> ORGANISM: Homo sapiens

<400> SEQUENCE: 24

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 25
<211> LENGTH: 147
<212> TYPE: PRT
<213> ORGANISM: Homo sapiens

<400> SEQUENCE: 25

Met Val Pro Ile Gln Lys Val Gln Asp Asp Thr Lys Thr Leu Ile Lys
1               5                   10                  15

Thr Ile Val Thr Arg Ile Asn Asp Ile Ser His Ala Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
```

```
            130                 135                 140
Pro Gly Cys
145

<210> SEQ ID NO 26
<211> LENGTH: 146
<212> TYPE: PRT
<213> ORGANISM: Homo sapiens

<400> SEQUENCE: 26

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 27
<211> LENGTH: 146
<212> TYPE: PRT
<213> ORGANISM: Homo sapiens

<400> SEQUENCE: 27

Met Val Pro Ile Gln Lys Val Gln Asp Asp Thr Lys Thr Leu Ile Lys
1               5                   10                  15

Thr Ile Val Thr Arg Ile Asn Asp Ile Ser His Ala Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
```

<210> SEQ ID NO 28
<211> LENGTH: 145
<212> TYPE: PRT
<213> ORGANISM: Unknown
<220> FEATURE:
<223> OTHER INFORMATION: Description of Unknown: Seal leptin polypeptide

<400> SEQUENCE: 28

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
                20                  25                  30

Pro Arg Val Ala Gly Leu Asp Phe Ile Pro Arg Val Gln Ser Val Arg
            35                  40                  45

Thr Leu Ser Gly Met Asp Gln Ile Leu Ala Thr Tyr Gln Gln Ile Leu
        50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
130                 135                 140

Cys
145

<210> SEQ ID NO 29
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
                20                  25                  30

Pro Arg Val Ala Gly Leu Asp Phe Ile Pro Arg Val Gln Ser Val Arg
            35                  40                  45

Thr Leu Ser Gly Met Asp Gln Ile Leu Ala Thr Tyr Gln Gln Ile Leu
        50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
130                 135                 140

Cys
145

<210> SEQ ID NO 30
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 31
<211> LENGTH: 146
<212> TYPE: PRT
<213> ORGANISM: Unknown
<220> FEATURE:
<223> OTHER INFORMATION: Description of Unknown: Seal leptin polypeptide

<400> SEQUENCE: 31

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

```
Leu Lys Ala Ala Leu Gln Asp Met Leu Arg Gln Leu Asp Arg Asn Pro
    130                 135                 140

Gly Cys
145
```

<210> SEQ ID NO 32
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
                20                  25                  30

Arg Pro Arg Val Ala Gly Leu Asp Phe Ile Pro Arg Val Gln Ser Val
            35                  40                  45

Arg Thr Leu Ser Gly Met Asp Gln Ile Leu Ala Thr Tyr Gln Gln Ile
        50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145
```

<210> SEQ ID NO 33
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Ser Ser
                20                  25                  30

Arg Pro Arg Val Ala Gly Leu Asp Phe Ile Pro Arg Val Gln Ser Val
            35                  40                  45

Arg Thr Leu Ser Gly Met Asp Gln Ile Leu Ala Thr Tyr Gln Gln Ile
        50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

Pro Val Pro Arg Ala Arg Gly Ser Asp Thr Ile Lys Gly Leu Gly Asn
            100                 105                 110
```

```
Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 34
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Val Pro Ile Gln Lys Val Gln Asp Asp Thr Lys Thr
225                 230                 235                 240

Leu Ile Lys Thr Ile Val Thr Arg Ile Asn Asp Ile Ser His Thr Gln
                245                 250                 255

Ser Val Ser Ser Lys Gln Lys Val Thr Gly Leu Asp Phe Ile Pro Gly
            260                 265                 270

Leu His Pro Ile Leu Thr Leu Ser Lys Met Asp Gln Thr Leu Ala Val
        275                 280                 285

Tyr Gln Gln Ile Leu Thr Ser Met Pro Ser Arg Asn Val Ile Gln Ile
    290                 295                 300

Ser Asn Asp Leu Glu Asn Leu Arg Asp Leu Leu His Val Leu Ala Phe
305                 310                 315                 320
```

```
Ser Lys Ser Cys His Leu Pro Trp Ala Ser Gly Leu Glu Thr Leu Asp
            325                 330                 335

Ser Leu Gly Gly Val Leu Glu Ala Ser Gly Tyr Ser Thr Glu Val Val
            340                 345                 350

Ala Leu Ser Arg Leu Gln Gly Ser Leu Gln Asp Met Leu Trp Gln Leu
            355                 360                 365

Asp Leu Ser Pro Gly Cys
            370
```

<210> SEQ ID NO 35
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Gln Leu Asp Leu Ser
        130                 135                 140

Pro Gly Cys
145
```

<210> SEQ ID NO 36
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Cys Asn Asp
65                  70                  75                  80
```

```
Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 37
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gly Gln Leu Asp Leu Ser
    130                 135                 140

Pro Gly Cys
145

<210> SEQ ID NO 38
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60
```

```
Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys Ser Leu Pro Gln Ala Ser Gly Leu Glu Thr Leu Gly Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 39
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys Ser Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 40
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
            35                  40                  45
```

```
Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Asp Ser Leu Gly
                100                 105                 110

Glu Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 41
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
                100                 105                 110

Glu Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 42
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30
```

```
Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys Ser Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 43
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Val Ser
    130                 135                 140

Pro Glu Cys
145

<210> SEQ ID NO 44
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Val Pro Ile Gln Lys Val Gln Asp Asp Thr Lys Thr Leu Ile Lys
 1               5                  10                  15
```

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Thr Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 45
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Glu Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Glu Cys
145

<210> SEQ ID NO 46
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 47
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Val Ser
        130                 135                 140

Pro Glu Cys
145

<210> SEQ ID NO 48
<211> LENGTH: 147
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Thr Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

<210> SEQ ID NO 49
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Thr Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Glu Cys
145

<210> SEQ ID NO 50
<211> LENGTH: 147
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 50

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys
145

<210> SEQ ID NO 51
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Glu Cys
145

```
<210> SEQ ID NO 52
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Pro Ile Gln Lys Val Gln Asp Asp Thr Lys Thr Leu Ile Lys Thr Ile
1               5                   10                  15

Val Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 53
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Pro Ile Gln Lys Val Gln Asp Asp Thr Lys Thr Leu Ile Lys Thr
1               5                   10                  15

Ile Val Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
```

<210> SEQ ID NO 54
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Lys Met Asp Gln Thr Leu Ala Val Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 55
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Lys Met Asp Gln Thr Leu Ala Val Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro

```
                130                 135                 140

Gly Cys
145

<210> SEQ ID NO 56
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Gln Gly Ser Leu Gln Asp Met Leu Trp Gln Leu Asp Leu Asn Pro Gly
    130                 135                 140

Cys
145

<210> SEQ ID NO 57
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
```

```
                    115                 120                 125
Leu Gln Gly Ser Leu Gln Asp Met Leu Trp Gln Leu Asp Leu Asn Pro
        130                 135                 140
Gly Cys
145

<210> SEQ ID NO 58
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Pro Ile Gln Arg Val Gln Asp Asp Thr Lys Thr Leu Ile Lys Thr Ile
1               5                   10                  15

Ile Thr Arg Ile Asn Asp Ile Ser His Thr Gln Ser Val Ser Ser Lys
            20                  25                  30

Gln Lys Val Thr Gly Leu Asp Phe Ile Pro Gly Leu His Pro Ile Leu
        35                  40                  45

Thr Leu Ser Gly Met Asp Gln Ile Leu Ala Thr Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 59
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Pro Ile Gln Arg Val Gln Asp Asp Thr Lys Thr Leu Ile Lys Thr
1               5                   10                  15

Ile Ile Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
```

```
              100                 105                 110
Val Leu Arg Ala Ser Val His Ser Thr Glu Val Val Ala Leu Ser Arg
            115                 120                 125

Leu Lys Ala Ala Leu Gln Asp Met Leu Arg Gln Leu Asp Arg Asn Pro
        130                 135                 140

Gly Cys
145

<210> SEQ ID NO 60
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys His
                85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 61
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
```

```
                85                  90                  95
His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 62
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Pro Ile Gln Lys Val Gln Asp Asp Thr Lys Thr Leu Ile Lys Thr Ile
1               5                   10                  15

Val Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 63
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Pro Ile Gln Lys Val Gln Asp Asp Thr Lys Thr Leu Ile Lys Thr
1               5                   10                  15

Ile Val Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Asn Val Ile Gln Ile Ser Asn Asp Leu
```

```
                65                  70                  75                  80
Glu Asn Leu Arg Asp Leu Leu His Val Leu Ala Phe Ser Lys Ser Cys
                    85                  90                  95

Pro Val Pro Arg Ala Arg Gly Ser Asp Thr Ile Lys Gly Leu Gly Asn
                100                 105                 110

Val Leu Arg Ala Ser Val His Ser Thr Glu Val Val Ala Leu Ser Arg
                115                 120                 125

Leu Lys Ala Ala Leu Gln Asp Met Leu Arg Gln Leu Asp Arg Asn Pro
        130                 135                 140

Gly Cys
145

<210> SEQ ID NO 64
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Pro Ile Gln Arg Val Gln Asp Asp Thr Lys Thr Leu Ile Lys Thr Ile
1               5                   10                  15

Ile Thr Arg Ile Asn Asp Ile Ser His Thr Gln Ser Val Ser Ser Lys
                20                  25                  30

Gln Lys Val Thr Gly Leu Asp Phe Ile Pro Gly Leu His Pro Ile Leu
            35                  40                  45

Thr Leu Ser Gly Met Asp Gln Ile Leu Ala Thr Tyr Gln Gln Ile Leu
        50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 65
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Pro Ile Gln Arg Val Gln Asp Asp Thr Lys Thr Leu Ile Lys Thr
1               5                   10                  15

Ile Ile Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Gly Met Asp Gln Ile Leu Ala Thr Tyr Gln Gln Ile
```

```
                50                  55                  60
Leu Thr Ser Leu Gln Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
                 85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 66
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Pro Ile Gln Arg Val Gln Asp Asp Thr Lys Thr Leu Ile Lys Thr Ile
 1               5                  10                  15

Ile Thr Arg Ile Asn Asp Ile Ser Pro Pro Gln Gly Val Cys Ser Arg
             20                  25                  30

Pro Arg Val Ala Gly Leu Asp Phe Ile Pro Arg Val Gln Ser Val Arg
         35                  40                  45

Thr Leu Ser Gly Met Asp Gln Ile Leu Ala Thr Tyr Gln Gln Ile Leu
     50                  55                  60

Thr Ser Leu Gln Ser Arg Asn Val Ile Gln Ile Ser Asn Asp Leu Glu
 65                  70                  75                  80

Asn Leu Arg Asp Leu Leu His Val Leu Ala Phe Ser Lys Ser Cys His
                 85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 67
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Pro Ile Gln Arg Val Gln Asp Asp Thr Lys Thr Leu Ile Lys Thr
 1               5                  10                  15

Ile Ile Thr Arg Ile Asn Asp Ile Ser Pro Pro Gln Gly Val Cys Ser
             20                  25                  30

Arg Pro Arg Val Ala Gly Leu Asp Phe Ile Pro Arg Val Gln Ser Val
```

```
                35                  40                  45
Arg Thr Leu Ser Gly Met Asp Gln Ile Leu Ala Thr Tyr Gln Gln Ile
 50                  55                  60

Leu Thr Ser Leu Gln Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
                 85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Lys Ala Ala Leu Gln Asp Met Leu Arg Gln Leu Asp Arg Asn Pro
            130                 135                 140

Gly Cys
145

<210> SEQ ID NO 68
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Pro Ile Gln Arg Val Gln Asp Asp Thr Lys Thr Leu Ile Lys Thr Ile
 1               5                  10                  15

Ile Thr Arg Ile Asn Asp Ile Ser His Thr Gln Ser Val Ser Ser Lys
                 20                  25                  30

Gln Lys Val Thr Gly Leu Asp Phe Ile Pro Gly Leu His Pro Ile Leu
             35                  40                  45

Thr Leu Ser Gly Met Asp Gln Ile Leu Ala Thr Tyr Gln Gln Ile Leu
 50                  55                  60

Thr Ser Leu Gln Ser Arg Ser Val Val Gln Ile Ala Asn Asp Leu Ala
 65                  70                  75                  80

Asn Leu Arg Ala Leu Leu Arg Leu Leu Ala Ser Ala Lys Ser Cys Pro
                 85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
            115                 120                 125

Gln Gly Ser Leu Gln Asp Met Leu Trp Gln Leu Asp Leu Asn Pro Gly
            130                 135                 140

Cys
145

<210> SEQ ID NO 69
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Pro Ile Gln Arg Val Gln Asp Asp Thr Lys Thr Leu Ile Lys Thr
 1               5                  10                  15

Ile Ile Thr Arg Ile Asn Asp Ile Ser His Thr Gln Ser Val Ser Ser
```

```
                 20                  25                  30
Lys Gln Lys Val Thr Gly Leu Asp Phe Ile Pro Gly Leu His Pro Ile
             35                  40                  45
Leu Thr Leu Ser Gly Met Asp Gln Ile Leu Ala Thr Tyr Gln Gln Ile
         50                  55                  60
Leu Thr Ser Leu Gln Ser Arg Ser Val Val Gln Ile Ala Asn Asp Leu
 65                  70                  75                  80
Ala Asn Leu Arg Ala Leu Leu Arg Leu Leu Ala Ser Ala Lys Ser Cys
                 85                  90                  95
Pro Val Pro Arg Ala Arg Gly Ser Asp Thr Ile Lys Gly Leu Gly Asn
            100                 105                 110
Val Leu Arg Ala Ser Val His Ser Thr Glu Val Val Ala Leu Ser Arg
            115                 120                 125
Leu Gln Gly Ser Leu Gln Asp Met Leu Trp Gln Leu Asp Leu Asn Pro
        130                 135                 140
Gly Cys
145

<210> SEQ ID NO 70
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Pro Ile Gln Arg Val Gln Asp Asp Thr Lys Thr Leu Ile Lys Thr Ile
 1               5                  10                  15
Ile Thr Arg Ile Asn Asp Ile Ser His Thr Gln Ser Val Ser Ser Lys
             20                  25                  30
Gln Lys Val Thr Gly Leu Asp Phe Ile Pro Gly Leu His Pro Ile Leu
             35                  40                  45
Thr Leu Ser Gly Met Asp Gln Ile Leu Ala Thr Tyr Gln Gln Ile Leu
         50                  55                  60
Thr Ser Leu Gln Ser Arg Ser Val Val Gln Ile Ala Asn Asp Leu Ala
 65                  70                  75                  80
Asn Leu Arg Ala Leu Leu Arg Leu Leu Ala Ser Ala Lys Ser Cys His
                 85                  90                  95
Leu Pro Trp Ala Ser Gly Leu Glu Thr Leu Asp Ser Leu Gly Gly Val
            100                 105                 110
Leu Glu Ala Ser Gly Tyr Ser Thr Glu Val Val Ala Leu Ser Arg Leu
            115                 120                 125
Lys Ala Ala Leu Gln Asp Met Leu Arg Gln Leu Asp Arg Asn Pro Gly
        130                 135                 140
Cys
145

<210> SEQ ID NO 71
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Pro Ile Gln Arg Val Gln Asp Asp Thr Lys Thr Leu Ile Lys Thr
```

```
            1               5                  10                 15
         Ile Ile Thr Arg Ile Asn Asp Ile Ser His Thr Gln Ser Val Ser Ser
                        20                 25                 30

Lys Gln Lys Val Thr Gly Leu Asp Phe Ile Pro Gly Leu His Pro Ile
                        35                 40                 45

Leu Thr Leu Ser Gly Met Asp Gln Ile Leu Ala Thr Tyr Gln Gln Ile
             50                 55                 60

Leu Thr Ser Leu Gln Ser Arg Ser Val Val Gln Ile Ala Asn Asp Leu
         65                 70                 75                 80

Ala Asn Leu Arg Ala Leu Leu Arg Leu Leu Ala Ser Ala Lys Ser Cys
                        85                 90                 95

His Leu Pro Trp Ala Ser Gly Leu Glu Thr Leu Asp Ser Leu Gly Gly
                        100                105                110

Val Leu Glu Ala Ser Gly Tyr Ser Thr Glu Val Val Ala Leu Ser Arg
                        115                120                125

Leu Lys Ala Ala Leu Gln Asp Met Leu Arg Gln Leu Asp Arg Asn Pro
                        130                135                140

Gly Cys
         145

<210> SEQ ID NO 72
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Pro Ile Gln Arg Val Gln Asp Asp Thr Lys Thr Leu Ile Lys Thr Ile
         1               5                  10                 15

Ile Thr Arg Ile Asn Asp Ile Ser His Thr Gln Ser Val Ser Ser Lys
                        20                 25                 30

Gln Lys Val Thr Gly Leu Asp Phe Ile Pro Gly Leu His Pro Ile Leu
                        35                 40                 45

Thr Leu Ser Gly Met Asp Gln Ile Leu Ala Thr Tyr Gln Gln Ile Leu
             50                 55                 60

Thr Ser Leu Gln Ser Arg Asn Val Ile Gln Ile Ser Asn Asp Leu Glu
         65                 70                 75                 80

Asn Leu Arg Asp Leu Leu His Val Leu Ala Phe Ser Lys Ser Cys His
                        85                 90                 95

Leu Pro Trp Ala Ser Gly Leu Glu Thr Leu Asp Ser Leu Gly Gly Val
                        100                105                110

Leu Glu Ala Ser Gly Tyr Ser Thr Glu Val Val Ala Leu Ser Arg Leu
                        115                120                125

Lys Ala Ala Leu Gln Asp Met Leu Arg Gln Leu Asp Arg Asn Pro Gly
                        130                135                140

Cys
         145

<210> SEQ ID NO 73
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 73

Met Pro Ile Gln Arg Val Gln Asp Asp Thr Lys Thr Leu Ile Lys Thr
1               5                   10                  15

Ile Ile Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Gly Met Asp Gln Ile Leu Ala Thr Tyr Gln Gln Ile
        50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Lys Ala Ala Leu Gln Asp Met Leu Arg Gln Leu Asp Arg Asn Pro
130                 135                 140

Gly Cys
145

<210> SEQ ID NO 74
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Pro Ile Gln Lys Val Gln Asp Asp Thr Lys Thr Leu Ile Lys Thr Ile
1               5                   10                  15

Val Thr Arg Ile Asn Asp Ile Ser Pro Pro Gln Gly Val Ser Ser Arg
                20                  25                  30

Pro Arg Val Ala Gly Leu Asp Phe Ile Pro Arg Val Gln Ser Val Arg
            35                  40                  45

Thr Leu Ser Gly Met Asp Gln Ile Leu Ala Thr Tyr Gln Gln Ile Leu
        50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
130                 135                 140

Cys
145

<210> SEQ ID NO 75
<211> LENGTH: 146
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 75

Met Pro Ile Gln Lys Val Gln Asp Asp Thr Lys Thr Leu Ile Lys Thr
1               5                   10                  15

Ile Val Thr Arg Ile Asn Asp Ile Ser Pro Pro Gln Gly Val Ser Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 76
<211> LENGTH: 145
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 76

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
            20                  25                  30

Pro Arg Val Ala Gly Leu Asp Phe Ile Pro Arg Val Gln Ser Val Arg
        35                  40                  45

Thr Leu Ser Lys Met Asp Gln Thr Leu Ala Val Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 77
<211> LENGTH: 146

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Ser Ser
            20                  25                  30

Arg Pro Arg Val Ala Gly Leu Asp Phe Ile Pro Arg Val Gln Ser Val
        35                  40                  45

Arg Thr Leu Ser Lys Met Asp Gln Thr Leu Ala Val Tyr Gln Gln Ile
50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 78
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Gln Gly Ser Leu Gln Asp Met Leu Trp Gln Leu Asp Leu Asn Pro Gly
    130                 135                 140

Cys
145
```

```
<210> SEQ ID NO 79
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Ser Ser
                20                  25                  30

Arg Pro Arg Val Ala Gly Leu Asp Phe Ile Pro Arg Val Gln Ser Val
            35                  40                  45

Arg Thr Leu Ser Gly Met Asp Gln Ile Leu Ala Thr Tyr Gln Gln Ile
        50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Gln Gly Ser Leu Gln Asp Met Leu Trp Gln Leu Asp Leu Asn Pro
130                 135                 140

Gly Cys
145

<210> SEQ ID NO 80
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
                20                  25                  30

Pro Arg Val Ala Gly Leu Asp Phe Ile Pro Arg Val Gln Ser Val Arg
            35                  40                  45

Thr Leu Ser Gly Met Asp Gln Ile Leu Ala Thr Tyr Gln Gln Ile Leu
        50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys His
                85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Lys Ala Ala Leu Gln Asp Met Leu Arg Gln Leu Asp Arg Asn Pro Gly
130                 135                 140
```

Cys
145

<210> SEQ ID NO 81
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Ser Ser
                20                  25                  30

Arg Pro Arg Val Ala Gly Leu Asp Phe Ile Pro Arg Val Gln Ser Val
            35                  40                  45

Arg Thr Leu Ser Gly Met Asp Gln Ile Leu Ala Thr Tyr Gln Gln Ile
        50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 82
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Pro Ile Gln Lys Val Gln Asp Asp Thr Lys Thr Leu Ile Lys Thr Ile
1               5                   10                  15

Val Thr Arg Ile Asn Asp Ile Ser Pro Gln Gly Val Ser Ser Arg
                20                  25                  30

Pro Arg Val Ala Gly Leu Asp Phe Ile Pro Arg Val Gln Ser Val Arg
            35                  40                  45

Thr Leu Ser Gly Met Asp Gln Ile Leu Ala Thr Tyr Gln Gln Ile Leu
        50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

```
Lys Ala Ala Leu Gln Asp Met Leu Arg Gln Leu Asp Arg Asn Pro Gly
        130                 135                 140

Cys
145

<210> SEQ ID NO 83
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Pro Ile Gln Lys Val Gln Asp Asp Thr Lys Thr Leu Ile Lys Thr
1               5                   10                  15

Ile Val Thr Arg Ile Asn Asp Ile Ser Pro Pro Gln Gly Val Ser Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 84
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
            100                 105                 110
```

```
Leu Glu Ala Ser Gly Tyr Ser Thr Glu Val Val Ala Leu Ser Arg Leu
        115                 120                 125

Lys Ala Ala Leu Gln Asp Met Leu Arg Gln Leu Asp Arg Asn Pro Gly
130                 135                 140

Cys
145

<210> SEQ ID NO 85
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Ser Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 86
<211> LENGTH: 37
<212> TYPE: PRT
<213> ORGANISM: Rattus norvegicus

<400> SEQUENCE: 86

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 87
<211> LENGTH: 37
<212> TYPE: PRT
<213> ORGANISM: Homo sapiens

<400> SEQUENCE: 87

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30
```

-continued

```
                20                  25                  30

Gly Ser Asn Thr Tyr
        35

<210> SEQ ID NO 88
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
                20                  25                  30

Gly Ser Asn Thr Tyr
        35

<210> SEQ ID NO 89
<211> LENGTH: 32
<212> TYPE: PRT
<213> ORGANISM: Homo sapiens

<400> SEQUENCE: 89

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                20                  25                  30

<210> SEQ ID NO 90
<211> LENGTH: 32
<212> TYPE: PRT
<213> ORGANISM: Unknown
<220> FEATURE:
<223> OTHER INFORMATION: Polypeptide from unknown Oncorhynchus species

<400> SEQUENCE: 90

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
                20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
    polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (21)..(21)
<223> OTHER INFORMATION: Lys, Cys or Asn
<220> FEATURE:
<221> NAME/KEY: MOD_RES
<222> LOCATION: (24)..(24)
<223> OTHER INFORMATION: Lys, Cys or Gly
<220> FEATURE:
<221> NAME/KEY: MOD_RES
<222> LOCATION: (25)..(25)
<223> OTHER INFORMATION: Lys, Cys or Pro
<220> FEATURE:
<221> NAME/KEY: MOD_RES
<222> LOCATION: (26)..(26)
<223> OTHER INFORMATION: Lys, Cys or Ile
<220> FEATURE:
<221> NAME/KEY: MOD_RES
<222> LOCATION: (27)..(27)
<223> OTHER INFORMATION: Lys, Cys or Leu
<220> FEATURE:
<221> NAME/KEY: MOD_RES
<222> LOCATION: (28)..(29)
<223> OTHER INFORMATION: Lys, Cys or Pro
<220> FEATURE:
<221> NAME/KEY: MOD_RES
<222> LOCATION: (31)..(31)
<223> OTHER INFORMATION: Lys, Cys or Asn

<400> SEQUENCE: 92

Lys Cys Asn Thr Ala Thr Cys Ala Thr Gln Arg Leu Ala Asn Phe Leu
1               5                   10                  15

Val His Ser Ser Xaa Asn Phe Xaa Xaa Xaa Xaa Xaa Thr Xaa Val
            20                  25                  30

Gly Ser Asn Thr Tyr
            35

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 93

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Asn Val Gly
            20                  25                  30

Ser Asn Thr Tyr
            35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (37)..(37)
<223> OTHER INFORMATION: AMIDATION

<400> SEQUENCE: 94

Lys Cys Asn Thr Ala Thr Cys Ala Thr Gln Arg Leu Ala Asn Phe Leu
1               5                   10                  15

Val Arg Ser Ser Lys Asn Leu Gly Pro Val Leu Pro Pro Thr Asn Val
            20                  25                  30

Gly Ser Asn Thr Tyr
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 95

Cys Asn Thr Ala Thr Cys Ala Thr Gln Arg Leu Ala Asn Phe Leu Val
1               5                   10                  15

Arg Ser Ser Lys Asn Leu Gly Pro Val Leu Pro Pro Thr Asn Val Gly
            20                  25                  30

Ser Asn Thr Tyr
        35

<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 96

Lys Cys Asn Thr Ala Thr Cys Ala Thr Gln Arg Leu Ala Asn Phe Leu
1               5                   10                  15

Val Arg Ser Ser Asn Asn Leu Gly Pro Lys Leu Pro Pro Thr Asn Val
            20                  25                  30

Gly Ser Asn Thr Tyr
        35

<210> SEQ ID NO 97
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 97

Cys Asn Thr Ala Thr Cys Ala Thr Gln Arg Leu Ala Asn Phe Leu Val
1               5                   10                  15
```

-continued

```
Arg Ser Ser Asn Asn Leu Gly Pro Lys Leu Pro Pro Thr Asn Val Gly
            20                  25                  30

Ser Asn Thr Tyr
        35

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 98

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Lys Val
            20                  25                  30

Gly Ser Asn Thr Tyr
        35

<210> SEQ ID NO 99
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 99

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Lys Val Gly
            20                  25                  30

Ser Asn Thr Tyr
        35

<210> SEQ ID NO 100
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 100

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

```
<210> SEQ ID NO 101
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 101

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 102
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 102

Cys Asn Thr Ala Thr Cys Ala Thr Gln Arg Leu Ala Asn Phe Leu Val
1               5                   10                  15

His Ser Ser Lys Asn Phe Gly Pro Ile Leu Pro Pro Thr Asn Val Gly
            20                  25                  30

Ser Asn Thr Tyr
        35

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 103

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 104
<211> LENGTH: 36
<212> TYPE: PRT
<213> ORGANISM: Artificial Sequence
<220> FEATURE:
<223> OTHER INFORMATION: Description of Artificial Sequence: Synthetic
```

```
                              polypeptide
<220> FEATURE:
<221> NAME/KEY: MOD_RES
<222> LOCATION: (36)..(36)
<223> OTHER INFORMATION: AMIDATION

<400> SEQUENCE: 104

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Lys Val Gly
            20                  25                  30

Ser Asn Thr Tyr
        35

<210> SEQ ID NO 105
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 105

Cys Asn Thr Ala Thr Cys Ala Thr Gln Arg Leu Ala Asn Phe Leu Val
1               5                   10                  15

His Ser Ser Asn Asn Phe Lys Pro Ile Leu Pro Pro Thr Asn Val Gly
            20                  25                  30

Ser Asn Thr Tyr
        35

<210> SEQ ID NO 106
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 106

Cys Asn Thr Ala Thr Cys Ala Thr Gln Arg Leu Ala Asn Phe Leu Val
1               5                   10                  15

His Ser Ser Asn Asn Phe Gly Lys Ile Leu Pro Pro Thr Asn Val Gly
            20                  25                  30

Ser Asn Thr Tyr
        35

<210> SEQ ID NO 107
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 107
```

Cys Asn Thr Ala Thr Cys Ala Thr Gln Arg Leu Ala Asn Phe Leu Val
1               5                   10                  15

His Ser Ser Asn Asn Phe Gly Pro Ile Lys Pro Pro Thr Asn Val Gly
            20                  25                  30

Ser Asn Thr Tyr
        35

<210> SEQ ID NO 108
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 108

Cys Asn Thr Ala Thr Cys Ala Thr Gln Arg Leu Ala Asn Phe Leu Val
1               5                   10                  15

His Ser Ser Asn Asn Phe Gly Pro Ile Leu Lys Pro Thr Asn Val Gly
            20                  25                  30

Ser Asn Thr Tyr
        35

<210> SEQ ID NO 109
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 109

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Lys Thr Asn Val Gly
            20                  25                  30

Ser Asn Thr Tyr
        35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 110

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

```
Gly Ser Asn Thr Tyr
        35

<210> SEQ ID NO 111
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 112
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 113
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

<210> SEQ ID NO 114
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
            20                  25                  30
```

Ser Asn Thr Tyr
        35

<210> SEQ ID NO 115
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 116
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Thr Asn Val Gly
            20                  25                  30

Ser Asn Thr Tyr
        35

<210> SEQ ID NO 117
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 118
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val

```
                    20                  25                  30

Gly Ser Asn Thr Tyr
        35

<210> SEQ ID NO 119
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Pro Ser Thr Asn Val
                    20                  25                  30

Gly Ser Asn Thr Tyr
        35

<210> SEQ ID NO 120
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
                    20                  25                  30

Ser Asn Thr Tyr
        35

<210> SEQ ID NO 121
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                    20                  25                  30

Gly Ser Asn Thr Tyr
        35

<210> SEQ ID NO 122
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Lys Ala Asn Thr Ala Thr Cys Ala Thr Gln Arg Leu Ala Asn Phe Leu
1               5                   10                  15
```

```
Val His Ser Ser Asn Asn Phe Gly Ala Ile Leu Ser Ser Thr Asn Val
            20                  25                  30

Gly Ser Asn Thr Tyr
        35

<210> SEQ ID NO 123
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Lys Ala Asn Thr Ala Thr Ala Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 124
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 125
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Pro Thr Asn Val
            20                  25                  30

Gly Ser Asn Thr Tyr
        35

<210> SEQ ID NO 126
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Lys Cys Asn Thr Ala Thr Cys Ala Thr Gln Arg Leu Ala Asn Phe Leu
1               5                   10                  15
```

```
Val His Ser Ser Asn Asn Phe Gly Pro Ile Leu Pro Ser Thr Asn Val
            20                  25                  30

Gly Ser Asn Thr Tyr
        35

<210> SEQ ID NO 127
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Ser Thr Asn Val Gly
            20                  25                  30

Ser Asn Thr Tyr
        35

<210> SEQ ID NO 128
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Thr Asn Val
            20                  25                  30

Gly Ser Asn Thr Tyr
        35

<210> SEQ ID NO 129
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 130
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Cys Asn Thr Ala Thr Cys Ala Thr Gln Arg Leu Ala Asn Phe Leu Val
```

His Ser Ser Asn Asn Leu Gly Pro Val Leu Pro Ser Thr Asn Val Gly
            20                  25                  30

Ser Asn Thr Tyr
        35

<210> SEQ ID NO 131
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 132
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

<210> SEQ ID NO 133
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 134
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
            35

<210> SEQ ID NO 135
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
            35

<210> SEQ ID NO 136
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
            35

<210> SEQ ID NO 137
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
            35

<210> SEQ ID NO 138
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
            35

<210> SEQ ID NO 139
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
            35

<210> SEQ ID NO 140
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
            35

<210> SEQ ID NO 141
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
            35

<210> SEQ ID NO 142
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 142

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

<210> SEQ ID NO 143
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 144
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 145
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 146
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: N-terminal linked to mPEG40KD
<220> FEATURE:
<221> NAME/KEY: MOD_RES
<222> LOCATION: (37)..(37)
<223> OTHER INFORMATION: AMIDATION

<400> SEQUENCE: 146

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 147
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: N-terminal linked to mPEG40KD
<220> FEATURE:
<221> NAME/KEY: MOD_RES
<222> LOCATION: (36)..(36)
<223> OTHER INFORMATION: ACETYLATION

<400> SEQUENCE: 147

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Asn Val Gly
            20                  25                  30

Ser Asn Thr Tyr
        35

<210> SEQ ID NO 148
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 148

Lys Cys Asn Thr Ala Thr Cys Ala Thr Gln Arg Leu Ala Asn Phe Leu
1               5                   10                  15

Val Arg Ser Ser Lys Asn Leu Gly Pro Val Leu Pro Pro Thr Asn Val
            20                  25                  30

Gly Ser Asn Thr Tyr
        35

<210> SEQ ID NO 149
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 149

Cys Asn Thr Ala Thr Cys Ala Thr Gln Arg Leu Ala Asn Phe Leu Val
1               5                   10                  15

Arg Ser Ser Lys Asn Leu Gly Pro Val Leu Pro Pro Thr Asn Val Gly
            20                  25                  30

Ser Asn Thr Tyr
        35

<210> SEQ ID NO 150
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 150

Lys Cys Asn Thr Ala Thr Cys Ala Thr Gln Arg Leu Ala Asn Phe Leu
1               5                   10                  15

Val Arg Ser Ser Asn Asn Leu Gly Pro Lys Leu Pro Pro Thr Asn Val
            20                  25                  30

Gly Ser Asn Thr Tyr
        35

<210> SEQ ID NO 151
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 151

Cys Asn Thr Ala Thr Cys Ala Thr Gln Arg Leu Ala Asn Phe Leu Val
1               5                   10                  15

Arg Ser Ser Asn Asn Leu Gly Pro Lys Leu Pro Pro Thr Asn Val Gly
            20                  25                  30

Ser Asn Thr Tyr
```

```
                        35

<210> SEQ ID NO 152
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 152

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Lys Val
            20                  25                  30

Gly Ser Asn Thr Tyr
        35

<210> SEQ ID NO 153
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 153

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Lys Val Gly
            20                  25                  30

Ser Asn Thr Tyr
        35

<210> SEQ ID NO 154
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(Y-shaped-mPEG40KD)
<220> FEATURE:
<221> NAME/KEY: MOD_RES
<222> LOCATION: (37)..(37)
<223> OTHER INFORMATION: AMIDATION

<400> SEQUENCE: 154

Lys Cys Asn Thr Ala Thr Cys Ala Thr Gln Arg Leu Ala Asn Phe Leu
1               5                   10                  15
```

```
Val Arg Ser Ser Asn Asn Leu Gly Pro Lys Leu Pro Pro Thr Asn Val
            20                  25                  30

Gly Ser Asn Thr Tyr
        35

<210> SEQ ID NO 155
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 155

Cys Asn Thr Ala Thr Cys Ala Thr Gln Arg Leu Ala Asn Phe Leu Val
1               5                   10                  15

His Ser Ser Lys Asn Phe Gly Pro Ile Leu Pro Pro Thr Asn Val Gly
            20                  25                  30

Ser Asn Thr Tyr
        35

<210> SEQ ID NO 156
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 156

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 157
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION
```

<400> SEQUENCE: 157

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Lys Val Gly
            20                  25                  30

Ser Asn Thr Tyr
        35

<210> SEQ ID NO 158
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(Y-shaped-mPEG40KD)
<220> FEATURE:
<221> NAME/KEY: MOD_RES
<222> LOCATION: (36)..(36)
<223> OTHER INFORMATION: AMIDATION

<400> SEQUENCE: 158

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 159
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 159

Cys Asn Thr Ala Thr Cys Ala Thr Gln Arg Leu Ala Asn Phe Leu Val
1               5                   10                  15

His Ser Ser Asn Asn Phe Lys Pro Ile Leu Pro Pro Thr Asn Val Gly
            20                  25                  30

Ser Asn Thr Tyr
        35

<210> SEQ ID NO 160
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)

<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 160

Cys Asn Thr Ala Thr Cys Ala Thr Gln Arg Leu Ala Asn Phe Leu Val
1               5                   10                  15

His Ser Ser Asn Asn Phe Gly Lys Ile Leu Pro Pro Thr Asn Val Gly
            20                  25                  30

Ser Asn Thr Tyr
        35

<210> SEQ ID NO 161
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 161

Cys Asn Thr Ala Thr Cys Ala Thr Gln Arg Leu Ala Asn Phe Leu Val
1               5                   10                  15

His Ser Ser Asn Asn Phe Gly Pro Ile Lys Pro Pro Thr Asn Val Gly
            20                  25                  30

Ser Asn Thr Tyr
        35

<210> SEQ ID NO 162
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 162

Cys Asn Thr Ala Thr Cys Ala Thr Gln Arg Leu Ala Asn Phe Leu Val
1               5                   10                  15

His Ser Ser Asn Asn Phe Gly Pro Ile Leu Lys Pro Pro Thr Asn Val Gly
            20                  25                  30

Ser Asn Thr Tyr
        35

<210> SEQ ID NO 163
<211> LENGTH: 36
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 163

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Lys Thr Asn Val Gly
            20                  25                  30

Ser Asn Thr Tyr
        35

<210> SEQ ID NO 164
<211> LENGTH: 6
<212> TYPE: PRT
<213> ORGANISM: Unknown
<220> FEATURE:
<223> OTHER INFORMATION: Description of Unknown: Leptin conserved motif
      peptide

<400> SEQUENCE: 164

Gly Leu Asp Phe Ile Pro
1               5
```

CHIMERIC LEPTIN POLYPEPTIDE AND METHOD OF USING THE SAME

CROSS-REFERENCES TO RELATED APPLICATIONS

This application is a continuation of U.S. patent application Ser. No. 13/852,521 filed Mar. 28, 2013, which is a continuation of International Patent Application No. PCT/US2011/053774, filed Sep. 28, 2011, which claims priority to U.S. Provisional Patent Application No. 61/387,402 filed Sep. 28, 2010, and U.S. Provisional Patent Application No. 61/422,091 filed Dec. 10, 2010, the disclosure of each of which are incorporated by reference herein.

SEQUENCE LISTING

The instant application contains a Sequence Listing which has been submitted in ASCII format via EFS-Web and is hereby incorporated by reference in its entirety. Said ASCII copy, created on Oct. 27, 2011, is named 92494-867805_ST25.TXT and is 161,202 bytes in size.

BACKGROUND OF THE INVENTION

The invention provides novel compounds that have demonstrated biological activity. The compounds also demonstrate surprising and significant improvement in physical properties, such as solubility and stability.

The compounds of the invention are based on leptin sequences disclosed in U.S. Application No. 61/387,402 and U.S. Application No. 61/422,091. The compounds are surprisingly highly soluble and do not demonstrate the propensity to aggregate, unlike the naturally occurring leptins. The physical properties of the compounds facilitate the preparation of soluble, pharmaceutically acceptable formulations and compositions, also provided by the invention. Diseases amenable to such treatment include lipodystrophy, dyslipidemia, hyperlipidemia, overweight, obesity, hypothalamic amenorrhea, Alzheimer's disease, leptin deficiency, fatty liver disease, diabetes (including type I and type II), non-alcoholic steatohepatitis (NASH), nonalcoholic fatty liver disease (NAFLD), metabolic syndrome X, and Huntington's Disease, or combinations thereof.

There remains a need to develop polypeptides useful in the above described metabolic diseases, conditions and disorders. Accordingly, it is an object of the present invention to provide novel polypeptides useful to treat the above conditions and methods for producing and using them.

Each patent, patent application, and publication cited herein is hereby incorporated herein by reference in its entirety and for all purposes.

BRIEF SUMMARY OF THE INVENTION

There are provided chimeric polypeptide compounds having leptin biological activity, in addition to enhanced physical properties. The compounds are chimeric polypeptides which are based on a wild type seal leptin polypeptide wherein at least one contiguous region of 1-30 amino acids of a wild type seal leptin sequence has been replaced with a contiguous region of 1-30 amino acids of a mature human leptin sequence.

In a first aspect, there is provided a chimeric polypeptide as described herein.

In another aspect, there is provided a method for treating a disease or disorder in a subject in need of treatment. The method includes administering a chimeric polypeptide as described herein to the subject.

In yet another aspect, there is provided a pharmaceutical composition which includes a chimeric polypeptide described herein in combination with a pharmaceutically acceptable excipient.

In yet another aspect are polynucleotides encoding the chimeric polypeptide and their intermediates, expression vectors bearing such polynucleotides, host cells expressing such polynucleotides, and means for their expression, synthesis, post-translational modification and isolation.

BRIEF DESCRIPTION OF THE DRAWINGS

FIG. 1A: food intake. FIG. 1B: change in body weight (% vehicle-corrected). FIG. 1C: dose response curve.

FIG. 2A: food intake. FIG. 2B: change in body weight (% vehicle-corrected). FIG. 2C: dose response curve.

DETAILED DESCRIPTION OF THE INVENTION

I. Definitions

Figure 1A:
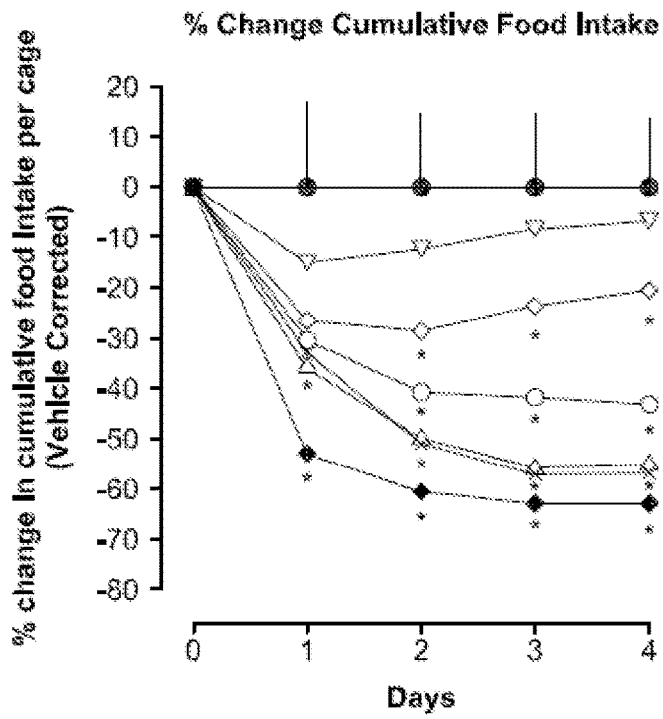
FIGS. 1A-1C depict the effects of a daily administration of the indicated chimeric polypeptides described herein on food intake and change in body weight (% vehicle-corrected) upon administration to C57/B6 female mice as described in Example 4.

"Obesity" and "overweight" refer to mammals having a weight greater than normally expected, and may be determined by, e.g., physical appearance, body mass index (BMI) as known in the art, waist-to-hip circumference ratios, skinfold thickness, waist circumference, and the like. The Centers for Disease Control and Prevention (CDC) define overweight as an adult human having a BMI of 25 to 29.9; and define obese as an adult human having a BMI of 30 or higher. Additional metrics for the determination of obesity exist. For example, the CDC states that a person with a waist-to-hip ratio greater than 1.0 is overweight.

"Lean body mass" refers to the fat-free mass of the body, i.e., total body weight minus body fat weight is lean body mass. Lean body mass can be measured by methods such as hydrostatic weighing, computerized chambers, dual-energy X-ray absorptiometry, skin calipers, magnetic resonance imaging (MRI) and bioelectric impedance analysis (BIA) as known in the art.

"Mammal" refers to warm-blooded animals that generally have fur or hair, that give live birth to their progeny, and that feed their progeny with milk. Mammals include humans; companion animals (e.g., dogs, cats); farm animals (e.g., cows, horses, sheep, pigs, goats); wild animals; and the like. In one embodiment, the mammal is a female. In one embodiment, the mammal is a female human. In one embodiment, the mammal is a cat or dog. In one embodiment, the mammal is a diabetic mammal, e.g., a human having type 2 diabetes. In one embodiment, the mammal is an obese diabetic mammal, e.g., an obese mammal having type 2 diabetes. The term "subject" in the context of methods described herein refers to a mammal.

"Fragment" in the context of polypeptides refers herein in the customary chemical sense to a portion of a polypeptide.

For example, a fragment can result from N-terminal deletion or C-terminal deletion of one or more residues of a parent polypeptide, and/or a fragment can result from internal deletion of one or more residues of a parent polypeptide. "Fragment" in the context of an antibody refers to a portion of an antibody which can be linked to a biologically active molecule to modulate solubility, distribution within a subject, and the like. For example, leptin A200 described herein is a conjugate of an Fc antibody fragment with a leptin, as known in the art. See e.g. WO 98/28427 and US2007/002084. The term "parent" in the context of polypeptides refers, in the customary sense, to a polypeptide which serves as a reference structure prior to modification, e.g., insertion, deletion and/or substitution.

"Analog" as used herein in the context of polypeptides refers to a compound that has insertions, deletions and/or substitutions of amino acids relative to a parent compound. An analog may have superior stability, solubility, efficacy, half-life, and the like. In some embodiments, an analog is a compound having at least 50%, for example 50%, 55%, 60%, 65%, 70%, 75%, 80%, 85%, 90%, 95%, 98%, or even higher, sequence identity to the parent compound.

"Identity," "sequence identity" and the like in the context of comparing two or more nucleic acids or polypeptide sequences, refer to two or more sequences or subsequences that are the same or have a specified percentage of amino acid residues or nucleotides that are the same (i.e., about 50% identity, preferably 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a sequence comparison algorithms as known in the art, for example BLAST or BLAST 2.0. This definition includes sequences that have deletions and/or additions, as well as those that have substitutions, as well as naturally occurring, e.g., polymorphic or allelic variants, and man-made variants. In preferred algorithms, account is made for gaps and the like, as known in the art. For sequence comparison, typically one sequence acts as a reference sequence, to which test sequences are compared. When using a sequence comparison algorithm, test and reference sequences are entered into a computer, subsequent coordinates are designated if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. See e.g., *Current Protocols in Molecular Biology* (Ausubel et al., eds. 1995 supplement)). Preferred examples of algorithms that are suitable for determining percent sequence identity and sequence similarity include the BLAST and BLAST 2.0 algorithms, which are described in Altschul et al., 1977, *Nucl. Acids Res.* 25:3389-3402 and Altschul et al., 1990, *J. Mol. Biol.* 215:403-410. BLAST and BLAST 2.0 are used, as known in the art, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Id.). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA* 89:10915) alignments (B) of 50, expectation (E) of 10, M=5, N=-4, and a comparison of both strands.

The term "about" in the context of a numeric value refers to +/- 10% of the numeric value, unless expressly indicated otherwise.

The terms "peptide" and "polypeptide" in the context of the compounds described herein are synonymous.

Leptins. "Leptins" and "a leptin" means: leptins, leptin active fragments, leptin analogs, and leptin derivatives; and a leptin, a leptin active fragment, a leptin analog, and a leptin derivative; respectively. Accordingly, unless otherwise noted, reference to "leptins" is meant to encompass leptins, leptin active fragments, leptin analogs, and leptin derivatives, as disclosed herein. Similarly, unless otherwise noted, reference to "a leptin" is meant to encompass a leptin, a leptin active fragment, a leptin analog, and a leptin derivative, as disclosed herein. Exemplary leptins which may be employed in the design, preparation, and use of the chimeric polypeptides disclosed herein include those which elicit one or more biological responses known in the art to be elicited when leptins are administered to subjects (see, e.g., published U.S. Patent application Nos. US 2007/0020284 and US 2008/0207512, U.S. Pat. No. 6,309,853, and U.S. Pat. No. 7,183,254, and PCT Published Application Nos. WO 96/005309, WO 98/28427, and WO 2009/064298), such as: reduction of food intake, reduction of body weight, reduction of body weight gain, induction of satiety, reduction of caloric availability, reduction of caloric efficiency, reduction of metabolic plateau, increase in insulin sensitivity, reduction of hyperlipidemia, correction of dyslipidemia, reduction of hypertriglyceridemia, amelioration of obesity, amelioration of overweight, amelioration of diabetes mellitus (including type I diabetes, type II diabetes, and gestational diabetes), amelioration of insulin resistance, amelioration of lipodystrophy conditions associated therewith, as well as other biological responses known in the art to be elicited upon administration of a leptin (see, e.g., published U.S. Patent Application Nos. US 2007/0020284 and US 2008/0207512, U.S. Pat. No. 6,309,853, and U.S. Pat. No. 7,183,254, and PCT Published Application Nos. WO 96/005309, WO 98/28427, and WO 2009/064298).

Leptins include, but are not limited to, the compounds described in U.S. Pat. No. 5,594,101, U.S. Pat. No. 5,851,995, U.S. Pat. No. 5,691,309, U.S. Pat. No. 5,580,954, U.S. Pat. No. 5,554,727, U.S. Pat. No. 5,552,523, U.S. Pat. No. 5,559,208, U.S. Pat. No. 5,756,461, U.S. Pat. No. 6,309,853, published U.S. Patent application No. US 2007/0020284, and PCT Published Application Nos. WO 96/23517, WO 96/005309, WO 98/28427, WO 2004/039832, WO 98/55139, WO 98/12224, and WO 97/02004, each of which is incorporated herein in its entirety and for all purposes. Methods to assay for leptin activities and biological responses in vitro and in vivo, including satiety, food intake inhibition activity and weight loss activity, are known in the art and are described herein and also in the above references and other references recited herein.

Representative leptins, leptin analogs, leptin active fragments, and leptin derivatives include the following:

Mature Murine leptins:

```
                                                (SEQ ID NO: 1)
VPIQKVQDDTKTLIKTIVTRINDISHT-Xaa-SVSSKQKVTGLDFIPGLH

PILTLSKMDQTLAVYQQILTSMPSRNVIQISNDLENLRDLLHVLAFSKSC

HLPQASGLETLESLGGVLEASGYSTEVVALSRLQGSLQDMLQQLDLSPG

C,
wherein Xaa at position 28 is Q or absent.
```

Mature Murine leptin form 1:

```
                                                (SEQ ID NO: 2)
VPIQKVQDDTKTLIKTIVTRINDISHTQSVSAKQRVTGLDFIPGLHPILS

LSKMDQTLAVYQQVLTSLPSQNVLQIANDLENLRDLLHLLAFSKSCSLPQ

TSGLQKPESLDGVLEASLYSTEVVALSRLQGSLQDILQQLDVSPEC.
```

Mature Murine leptin form 2:

```
                                                (SEQ ID NO: 3)
VPIQKVQDDTKTLIKTIVTRINDISHTSVSAKQRVTGLDFIPGLHPILSL

SKMDQTLAVYQQVLTSLPSQNVLQIANDLENLRDLLHLLAFSKSCSLPQT

SGLQKPESLDGVLEASLYSTEVVALSRLQGSLQDILQQLDVSPEC.
```

Mature Murine leptins with N-terminal methionine:

```
                                                (SEQ ID NO: 4)
MVPIQKVQDDTKTLIKTIVTRINDISHT-Xaa-SVSSKQKVTGLDFIPGL

HPILTLSKMDQTLAVYQQILTSMPSRNVIQISNDLENLRDLLHVLAFSKS

CHLPQASGLETLESLGGVLEASGYSTEVVALSRLQGSLQDMLQQLDLSPG

C,
wherein Xaa at position 29 is Q or absent.
```

Mature Murine leptin form 1 with N-terminal methionine:

```
                                                (SEQ ID NO: 5)
MVPIQKVQDDTKTLIKTIVTRINDISHTQSVSAKQRVTGLDFIPGLHPIL

SLSKMDQTLAVYQQVLTSLPSQNVLQIANDLENLRDLLHLLAFSKSCSLP

QTSGLQKPESLDGVLEASLYSTEVVALSRLQGSLQDILQQLDVSPEC.
```

Mature Murine leptin form 2 with N-terminal methionine:

```
                                                (SEQ ID NO: 6)
MVPIQKVQDDTKTLIKTIVTRINDISHTSVSAKQRVTGLDFIPGLHPILS

LSKMDQTLAVYQQVLTSLPSQNVLQIANDLENLRDLLHLLAFSKSCSLPQ

TSGLQKPESLDGVLEASLYSTEVVALSRLQGSLQDILQQLDVSPEC.
```

Mature Porcine leptin:

```
                                                (SEQ ID NO: 7)
VPIWRVQDDTKTLIKTIVTRISDISHMQSVSSKQRVTGLDFIPGLHPVLS

LSKMDQTLAIYQQILTSLPSRNVIQISNDLENLRDLLHLLASSKSCPLPQ

ARALETLESLGGVLEASLYSTEVVALSRLQGALQDMLRQLDLSPGC.
```

Mature Porcine leptin with N-terminal methionine:

```
                                                (SEQ ID NO: 8)
MVPIWRVQDDTKTLIKTIVTRISDISHMQSVSSKQRVTGLDFIPGLHPVL

SLSKMDQTLAIYQQILTSLPSRNVIQISNDLENLRDLLHLLASSKSCPLP

QARALETLESLGGVLEASLYSTEVVALSRLQGALQDMLRQLDLSPGC.
```

Mature Bovine leptins:

```
                                                (SEQ ID NO: 9)
VPICKVQDDTKTLIKTIVTRINDISHT-Xaa-SVSSKQRVTGLDFIPGLH

PLLSLSKMDQTLAIYQQILTSLPSRNVVQISNDLENLRDLLHLLAASKSC

PLPQVRALESLESLGVVLEASLYSTEVVALSRLQGSLQDMLRQLDLSPG

C,
wherein Xaa at position 28 is Q or absent.
```

Mature Bovine leptins with N-terminal methionine:

```
                                                (SEQ ID NO: 10)
MVPICKVQDDTKTLIKTIVTRINDISHT-Xaa-SVSSKQRVTGLDFIPGL

HPLLSLSKMDQTLAIYQQILTSLPSRNVVQISNDLENLRDLLHLLAASKS

CPLPQVRALESLESLGVVLEASLYSTEVVALSRLQGSLQDMLRQLDLSPG

C,
wherein Xaa at position 29 is Q or absent.
```

Unprocessed Full-length Human Leptin (i.e., includes 21-residue N-terminal signal sequence):

```
                                                (SEQ ID NO: 11)
MHWGTLCGFLWLWPYLFYVQAVPIQKVQDDTKTLIKTIVTRINDISHTQS

VSSKQKVTGLDFIPGLHPILTLSKMDQTLAVYQQILTSMPSRNVIQISND

LENLRDLLHVLAFSKSCHLPWASGLETLDSLGGVLEASGYSTEVVALSRL

QGSLQDMLWQLDLSPGC
```

Mature Human leptins (with N-terminal 21 amino acid signal sequence removed):

(SEQ ID NO: 12)
VPIQKVQDDTKTLIKTIVTRINDISH-Xaa-Xaa-SVSSKQKVTGLDFIP
GLHPILTLSKMDQTLAVYQQILTSMPSRNVIQISNDLENLRDLLHVLAFS
KSCHLPWASGLETLDSLGGVLEASGYSTEVVALSRLQGSLQDMLWQLDLS
PGC,
wherein: Xaa at position 27 is T or A; and Xaa at position 28 is Q or absent.

Mature Human leptins with N-terminal methionine:

(SEQ ID NO: 13)
MVPIQKVQDDTKTLIKTIVTRINDISH-Xaa-Xaa-SVSSKQKVTGLDFI
PGLHPILTLSKMDQTLAVYQQILTSMPSRNVIQISNDLENLRDLLHVLAF
SKSCHLPWASGLETLDSLGGVLEASGYSTEVVALSRLQGSLQDMLWQLDL
SPGC,
wherein: Xaa at position 28 is T or A; and Xaa at position 29 is Q or absent.

Mature Rhesus Leptin:

(SEQ ID NO: 14)
VPIQKVQSDTKTLIKTIVTRINDISHTQSVSSKQRVTGLDFIPGLHPVLT
LSQMDQTLAIYQQILINLPSRNVIQISNDLENLRDLLHLLAFSKSCHLPL
ASGLETLESLGDVLEASLYSTEVVALSRLQGSLQDMLWQLDLSPGC.

Mature Rhesus Leptin with N-terminal methionine:

(SEQ ID NO: 15)
MVPIQKVQSDTKTLIKTIVTRINDISHTQSVSSKQRVTGLDFIPGLHPVL
TLSQMDQTLAIYQQILINLPSRNVIQISNDLENLRDLLHLLAFSKSCHLP
LASGLETLESLGDVLEASLYSTEVVALSRLQGSLQDMLWQLDLSPGC.

Mature Rat leptin:

(SEQ ID NO: 16)
VPIHKVQDDTKTLIKTIVTRINDISHTQSVSARQRVTGLDFIPGLHPILS
LSKMDQTLAVYQQILTSLPSQNVLQIAHDLENLRDLLHLLAFSKSCSLPQ
TRGLQKPESLDGVLEASLYSTEVVALSRLQGSLQDILQQLDLSPEC.

Mature Rat leptin with N-terminal methionine:

(SEQ ID NO: 17)
MVPIHKVQDDTKTLIKTIVTRINDISHTQSVSARQRVTGLDFIPGLHPIL
SLSKMDQTLAVYQQILTSLPSQNVLQIAHDLENLRDLLHLLAFSKSCSLP
QTRGLQKPESLDGVLEASLYSTEVVALSRLQGSLQDILQQLDLSPEC.

Mature Platypus leptin: The mature platypus leptin sequence follows:

(SEQ ID NO: 18)
ISIEKIQADTKTLTKTIITRIIQLSTQNGVSTDQRVSGLDFIPGNQQFQN
LADMDQTLAVYQQILSSLPMPDRTQISNDLENLRSLFALLATLKNCPFTR
SDGLDTMEIWGGIVEESLYSTEVVTLDRLRKSLKNIEKQLDHIQG.

Unprocessed Full-length Platypus leptin (i.e., includes 21-residue N-terminal signal sequence): A full length sequence of platypus leptin, including a 21-residue N-terminal signal sequence follows:

(SEQ ID NO: 19)
MRCILLYGFLCVWQHLYYSHPISIEKIQADTKTLTKTIITRIIQLSTQNG
VSTDQRVSGLDFIPGNQQFQNLADMDQTLAVYQQILSSLPMPDRTQISND
LENLRSLFALLATLKNCPFTRSDGLDTMEIWGGIVEESLYSTEVVTLDRL
RKSLKNIEKQLDHIQG.

Mature Human Leptin form 1:

(SEQ ID NO: 20)
VPIQKVQDDTKTLIKTIVTRINDISHTQSVSSKQKVTGLDFIPGLHPILT
LSKMDQTLAVYQQILTSMPSRNVIQISNDLENLRDLLHVLAFSKSCHLPW
ASGLETLDSLGGVLEASGYSTEVVALSRLQGSLQDMLWQLDLSPGC.

Mature Human Leptin form 2:

(SEQ ID NO: 21)
VPIQKVQDDTKTLIKTIVTRINDISHAQSVSSKQKVTGLDFIPGLHPILT
LSKMDQTLAVYQQILTSMPSRNVIQISNDLENLRDLLHVLAFSKSCHLPW
ASGLETLDSLGGVLEASGYSTEVVALSRLQGSLQDMLWQLDLSPGC.

Mature Human Leptin form 3:

(SEQ ID NO: 22)
VPIQKVQDDTKTLIKTIVTRINDISHTSVSSKQKVTGLDFIPGLHPILTL
SKMDQTLAVYQQILTSMPSRNVIQISNDLENLRDLLHVLAFSKSCHLPWA
SGLETLDSLGGVLEASGYSTEVVALSRLQGSLQDMLWQLDLSPGC.

Mature Human Leptin form 4:

(SEQ ID NO: 23)
VPIQKVQDDTKTLIKTIVTRINDISHASVSSKQKVTGLDFIPGLHPILTL
SKMDQTLAVYQQILTSMPSRNVIQISNDLENLRDLLHVLAFSKSCHLPWA
SGLETLDSLGGVLEASGYSTEVVALSRLQGSLQDMLWQLDLSPGC.

Mature Human Leptin form 1 with N-terminal methionine (also known as Metreleptin, or A100):

(SEQ ID NO: 24)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
WASGLETLDSLGGVLEASGYSTEVVALSRLQGSLQDMLWQLDLSPGC.

Mature Human Leptin form 2 with N-terminal methionine:

(SEQ ID NO: 25)
MVPIQKVQDDTKTLIKTIVTRINDISHAQSVSSKQKVTGLDFIPGLHPIL

TLSKMDQTLAVYQQILTSMPSRNVIQISNDLENLRDLLHVLAFSKSCHLP

WASGLETLDSLGGVLEASGYSTEVVALSRLQGSLQDMLWQLDLSPGC.

Mature Human Leptin form 3 with N-terminal methionine:

(SEQ ID NO: 26)
MVPIQKVQDDTKTLIKTIVTRINDISHTSVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Mature Human Leptin form 4 with N-terminal methionine:

(SEQ ID NO: 27)
MVPIQKVQDDTKTLIKTIVTRINDISHASVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Seal leptin:

(SEQ ID NO: 28)
PIQRVQDDTKTLIKTIITRINDISPPQGVCSRPRVAGLDFIPRVQSVRTL

SGMDQILATYQQILTSLQSRSVVQIANDLANLRALLRLLASAKSCPVPRA

RGSDTIKGLGNVLRASVHSTEVVALSRLKAALQDMLRQLDRNPGC.

Seal leptin with amino acids 71-92 replaced with amino acids 73-94 (helix 3) of metreleptin, respectively:

(SEQ ID NO: 29)
PIQRVQDDTKTLIKTIITRINDISPPQGVCSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC.

Seal leptin with amino acids 30 and 71-92 replaced with amino acids 32 and 73-94 (helix 3) of metreleptin, respectively:

(SEQ ID NO: 30)
PIQRVQDDTKTLIKTIITRINDISPPQGVSSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC.

Seal leptin with N-terminal methionine:

(SEQ ID NO: 31)
MPIQRVQDDTKTLIKTIITRINDISPPQGVCSRPRVAGLDFIPRVQSVRT

LSGMDQILATYQQILTSLQSRSVVQIANDLANLRALLRLLASAKSCPVPR

ARGSDTIKGLGNVLRASVHSTEVVALSRLKAALQDMLRQLDRNPGC.

Seal leptin with N-terminal methionine, and with amino acids 71-92 replaced with amino acids 73-94 (helix 3) of metreleptin, respectively:

(SEQ ID NO: 32)
MPIQRVQDDTKTLIKTIITRINDISPPQGVCSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC.

Seal leptin with N-terminal methionine, and with amino acids 30 and 71-92 replaced with amino acids 32 and 73-94 (helix 3) of metreleptin, respectively:

(SEQ ID NO: 33)
MPIQRVQDDTKTLIKTIITRINDISPPQGVSSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC.

Leptin A200: Leptin A200 is an Fc antibody fragment condensation product with leptin, as known in the art. See e.g., Lo et al., 2005, *Protein Eng. Design & Selection,* 18:1-10. The amino acid sequence of A200 is as follows:

(SEQ ID NO: 34)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGKVPIQKVQDDTKTLIKTIVTRIN

DISHTQSVSSKQKVTGLDFIPGLHPILTLSKMDQTLAVYQQILTSMPSRN

VIQISNDLENLRDLLHVLAFSKSCHLPWASGLETLDSLGGVLEASGYSTE

VVALSRLQGSLQDMLWQLDLSPGC

Leptin A300: Leptin A300 is metreleptin with substitutions W101Q and W139Q (N-terminal [1]Met counted as residue 1):

(SEQ ID NO: 35)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCHLP

QASGLETLDSLGGVLEASGYSTEVVALSRLQGSLQDMLQQLDLSPGC.

Leptin A400: Leptin A400 is metreleptin with the serine residue at position 78 replaced with a cysteine residue, as set forth following:

(SEQ ID NO: 36)
MVPIQKVQDDTKTLIKTIVTRINDISHTQSVSSKQKVTGLDFIPGLHPIL

TLSKMDQTLAVYQQILTSMPSRNVIQICNDLENLRDLLHVLAFSKSCHLP

WASGLETLDSLGGVLEASGYSTEVVALSRLQGSLQDMLWQLDLSPGC;

to which a 20 kilodalton (kDa) PEG moiety has been attached via the cysteine residue at position 78.

Leptin A500: Research by a number of investigators including the inventors has focused on the effects on aggregation of residue substitution in leptin. See e.g., Ricci et al., 2006. "Mutational approach to improve physical stability of protein therapeutics susceptible to aggregation: Role of altered conformation in irreversible precipitation," Book Chapter. In: MISBEHAVING PROTEINS: PROTEIN (MIS)FOLDING, AGGREGATION, AND STABILITY, Murphy R M, Tsai A M, Eds., New York. Springer. pp. 331-350, which is incorporated herein by reference and for all purposes. Accordingly, leptin A500 with sequence following has been used in certain compounds and methods described herein:

(SEQ ID NO: 37)
MVPIQKVQDDTKTLIKTIVTRINDISHTQSVSSKQKVTGLEFIPGLHP

ILTLSKMDQTLAVYQQILTSMPSRNVIQISNDLENLRDLLHVLAFSKS

CHLPQASGLETLESLGGVLEASGYSTEVVALSRLQGSLQDMLQQLDLS

PGC.

Leptin A100 Variants: Variants of Leptin A100 with the following amino acid substitutions follow:

D41E, H98S, W101Q, D109E, G113E, M137I, W139Q and G146E:
(SEQ ID NO: 38)
MVPIQKVQDDTKTLIKTIVTRINDISHTQSVSSKQKVTGLEFIPGLHPI

LTLSKMDQTLAVYQQILTSMPSRNVIQISNDLENLRDLLHVLAFSKSCS

LPQASGLETLESLGEVLEASGYSTEVVALSRLQGSLQDILQQLDLSPEC.

H98S, W101Q, A102T, G113E, M137I, W139Q, and G146E:
(SEQ ID NO: 39)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQASGLETLDSLGGVLEASGYSTEVVALSRLQGSLQDILQQLDLSPEC.

H98S, W101Q, G113E, M137I, W139Q, and G146E:
(SEQ ID NO: 40)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQASGLETLDSLGEVLEASGYSTEVVALSRLQGSLQDILQQLDLSPEC.

W101Q, G113E, M137I, W139Q, and G146E:
(SEQ ID NO: 41)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGEVLEASGYSTEVVALSRLQGSLQDILQQLDLSPEC.

H98S, W101Q, M137I, W139Q, and G146E:
(SEQ ID NO: 42)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQASGLETLDSLGGVLEASGYSTEVVALSRLQGSLQDILQQLDLSPEC.

W101Q, G113E, M137I, W139Q, L143V, and G146E:
(SEQ ID NO: 43)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGEVLEASGYSTEVVALSRLQGSLQDILQQLDVSPEC.

H98S, W101Q, A102T, M137I, W139Q, and G146E:
(SEQ ID NO: 44)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQTSGLETLDSLGGVLEASGYSTEVVALSRLQGSLQDILQQLDLSPEC.

H98S, W101Q, D109E, G113E, and G146E:
(SEQ ID NO: 45)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQASGLETLESLGEVLEASGYSTEVVALSRLQGSLQDMLWQLDLSPEC.

W101Q, M137I, W139Q, and G146E:
(SEQ ID NO: 46)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGGVLEASGYSTEVVALSRLQGSLQDILQQLDLSPEC.

W101Q, M137I, W139Q, L143V, and G146E:
(SEQ ID NO: 47)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGGVLEASGYSTEVVALSRLQGSLQDILQQLDVSPEC.

H98S, W101Q, A102T, M137I, W139Q, L143V, and G146E:
(SEQ ID NO: 48)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQTSGLETLDSLGGVLEASGYSTEVVALSRLQGSLQDILQQLDVSPEC.

H98S, W101Q, A102T, G113E, and G146E:
(SEQ ID NO: 49)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCS

LPQTSGLETLDSLGEVLEASGYSTEVVALSRLQGSLQDMLWQLDLSPEC.

W101Q, G113E, and W139Q:
(SEQ ID NO: 50)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGEVLEASGYSTEVVALSRLQGSLQDMLQQLDLSPGC.

W101Q, G113E, W139Q, and G146E:
(SEQ ID NO: 51)
MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPQASGLETLDSLGEVLEASGYSTEVVALSRLQGSLQDMLQQLDLSPEC.

II. Chimeric Polypeptides

In one aspect of the present disclosure, a series of chimeric polypeptides are described. These chimeric polypeptides are based on a wild type seal leptin polypeptide wherein at least one contiguous region of 1-30 amino acids of a wild type seal leptin sequence has been replaced with a contiguous region of 1-30 amino acids of a mature human leptin sequence. A wild type seal leptin sequence includes the sequence of wild type seal leptin (SEQ ID NO:28) and the sequence of wild type seal leptin with an N-terminal methionine (SEQ ID NO:31). A mature human leptin sequence, useful for chimerizing wild type seal leptin as provided herein, includes the following sequences described above: mature human leptins (SEQ ID NO:12), mature human leptins with N-terminal methionine (SEQ ID NO:13), mature human leptin form 1 (SEQ ID NO:20), mature human leptin form 2 (SEQ ID NO:21), mature human leptin form 3 (SEQ ID NO:22), mature human leptin form 4 (SEQ ID NO:23), mature human leptin form 1 with N-terminal methionine (Metreleptin, or A100, SEQ ID NO:24), mature human leptin form 2 with N-terminal methionine (SEQ ID NO:25), mature human leptin form 3 with N-terminal methionine (SEQ ID NO:26), mature human leptin form 4 with N-terminal methionine (SEQ ID NO:27), A200 (SEQ ID NO:34), A300 (SEQ ID NO:35), A400 (SEQ ID NO:36), A500 (SEQ ID NO:37), and A100 variants (SEQ ID NO:38-51). In some embodiments, a series of chimeric polypeptides are described wherein at least one contiguous region of 1-30 amino acids of a wild type seal leptin sequence (SEQ ID NO. 28 or SEQ ID NO:31) has been replaced with a contiguous region of 1-30 amino acids of A100 (SEQ ID NO. 24).

In any of the disclosed chimeric polypeptides, a contiguous region of 1-30 amino acids can comprise any naturally or non-naturally occurring amino acid. Any combination of amino acids can be employed without restriction. That is, two or more amino acids in a contiguous region can be replaced with a naturally occurring amino acid, a non-naturally occurring amino acid, a conservative substitution, a non-conservative substitution or any combination thereof.

The chimeric polypeptides described herein have demonstrated biological activity, in addition to enhanced physical properties. For example, the seal-human chimeric polypeptides show leptin activity in vitro and in vivo. The chimeric polypeptides also show enhanced stability and solubility compared to the mature human leptin polypeptides which are used to derive the sequences, as shown by the Examples.

The term "leptin activity" includes leptin binding activity and leptin functional activity. The skilled artisan will recognize leptin analog compounds with leptin activity using suitable assays for measuring leptin binding or leptin functional activity. Leptin analog compounds can have an $IC_{50}$ of about 200 nM or less, about 100 nM or less, or about 50 nM or less, or about 5 nM or less, or about 1 nM or less, in a leptin binding assay, such as that described herein. The term "$IC_{50}$" refers in the customary sense to the half maximal inhibitory concentration of a compound inhibiting a biological or biochemical function. Accordingly, in the context of receptor binding studies, $IC_{50}$ refers to the concentration of a test compound which competes half of a known ligand from a specified receptor. Leptin analog compounds can have an $EC_{50}$ of about 20 nM or less, about 10 nM or less, about 5 nM or less, about 1 nM or less, or about 0.1 nM or less, in a leptin functional assay, such as that described herein. The term "$EC_{50}$" refers in the customary sense to the effective concentration of a compound which induces a response halfway between a baseline response and maximum response, as known in the art.

A. Chimeric Polypeptides Incorporating Human Helix 1

The Helix 1 region of a mature human leptin polypeptide spans a contiguous region of 20 amino acids. Helix 1 and Helix 3 are antiparallel helices that form part of Binding Site II of leptin to its receptor. This site interacts with the cytokine receptor homology domain (CRH) of the leptin receptor and is thought to be a major receptor binding site, but not involved in receptor activation. See, for example, Peelman et al., 2004, J. Biol. Chem. 279: 41038.

In one aspect, the present disclosure relates to chimeric polypeptides that are based on wild type seal leptin with an incorporated helix 1 sequence from mature human leptin. In some embodiments, a chimeric polypeptide comprises the amino acid sequence of a wild type seal leptin polypeptide (SEQ ID NO:28), wherein the contiguous region spanning the amino acids at positions 3-22 of SEQ ID NO:28 has been replaced with a contiguous region spanning the amino acids at positions 5-24 of A100 (SEQ ID NO:24). In some embodiments, a chimeric polypeptide comprises the sequence described in SEQ ID NO:52:

Seal leptin with amino acids 3-22 replaced with amino acids 5-24 (helix 1) of metreleptin, respectively:

```
                                      (SEQ ID NO: 52)
PIQKVQDDTKTLIKTIVTRINDISPPQGVCSRPRVAGLDFIPRVQSVRT

LSGMDQILATYQQILTSLQSRSVVQIANDLANLRALLRLLASAKSCPVP

RARGSDTIKGLGNVLRASVHSTEVVALSRLKAALQDMLRQLDRNPGC.
```

In some embodiments, a chimeric polypeptide comprises the amino acid sequence of a wild type seal leptin polypeptide with an N-terminal methionine (SEQ ID NO:31), wherein the contiguous region spanning the amino acids at positions 3-22 of SEQ ID NO:31 has been replaced with a contiguous region spanning the amino acids at positions 5-24 of A100 (SEQ ID NO:24). In some embodiments, a chimeric polypeptide comprises the sequence described in SEQ ID NO:53:

Seal leptin with N-terminal methionine, and with amino acids 3-22 replaced with amino acids 5-24 (helix 1) of metreleptin, respectively:

```
                                      (SEQ ID NO: 53)
MPIQKVQDDTKTLIKTIVTRINDISPPQGVCSRPRVAGLDFIPRVQSVR

TLSGMDQILATYQQILTSLQSRSVVQIANDLANLRALLRLLASAKSCPV

PRARGSDTIKGLGNVLRASVHSTEVVALSRLKAALQDMLRQLDRNPGC.
```

B. Chimeric Polypeptides Incorporating Human Helix 2

The Helix 2 region of a mature human leptin polypeptide spans a region of 16 contiguous amino acids. This helix is buried in the 4-helix bundle as described in the original crystal structure paper by Zhang et al. (Nature 1997 387: 206).

In one aspect, the present disclosure relates to chimeric polypeptides that are based on wild type seal leptin with an incorporated helix 2 sequence from mature human leptin. In some embodiments, a chimeric polypeptide comprises the amino acid sequence of a wild type seal leptin polypeptide (SEQ ID NO:28), wherein the contiguous region spanning the amino acids at positions 50-65 of SEQ ID NO:28 has been replaced with a contiguous region spanning the amino acids at positions 52-67 of A100 (SEQ ID NO:24). In some embodiments, a chimeric polypeptide comprises the sequence described in SEQ ID NO:54:

Seal leptin with amino acids 50-65 replaced with amino acids 52-67 (helix 2) of metreleptin, respectively:

```
                                      (SEQ ID NO: 54)
PIQRVQDDTKTLIKTIITRINDISPPQGVCSRPRVAGLDFIPRVQSVRT

LSKMDQTLAVYQQILTSLQSRSVVQIANDLANLRALLRLLASAKSCPVP

RARGSDTIKGLGNVLRASVHSTEVVALSRLKAALQDMLRQLDRNPGC.
```

In some embodiments, a chimeric polypeptide comprises the amino acid sequence of a wild type seal leptin polypeptide with an N-terminal methionine (SEQ ID NO:31), wherein the contiguous region spanning the amino acids at positions 50-65 of SEQ ID NO:31 has been replaced with a contiguous region spanning the amino acids at positions 52-67 of A100 (SEQ ID NO:24). In some embodiments, a chimeric polypeptide comprises the sequence described in SEQ ID NO:55:

Seal leptin with N-terminal methionine, and with amino acids 50-65 replaced with amino acids 52-67 (helix 2) of metreleptin, respectively:

(SEQ ID NO: 55)
MPIQRVQDDTKTLIKTIITRINDISPPQGVCSRPRVAGLDFIPRVQSVR

TLSKMDQTLAVYQQILTSLQSRSVVQIANDLANLRALLRLLASAKSCPV

PRARGSDTIKGLGNVLRASVHSTEVVALSRLKAALQDMLRQLDRNPGC.

C. Chimeric Polypeptides Incorporating Human Helix 3

The Helix 3 region of a mature human leptin polypeptide spans a contiguous region of 22 amino acids. Helix 3 and Helix 1 are antiparallel helices that form part of Binding Site II of leptin to its receptor. This site interacts with the cytokine receptor homology domain (CRH) of the leptin receptor and is thought to be a major receptor binding site, but not involved in receptor activation. See, for example, Peelman et al., 2004, J. Biol. Chem. 279: 41038.

In one aspect, the present disclosure relates to chimeric polypeptides that are based on wild type seal leptin with an incorporated helix 3 sequence from mature human leptin. In some embodiments, a chimeric polypeptide comprises the amino acid sequence of a wild type seal leptin polypeptide (SEQ ID NO:28), wherein the contiguous region spanning the amino acids at positions 71-92 of SEQ ID NO:28 has been replaced with a contiguous region spanning the amino acids at positions 73-94 of A100 (SEQ ID NO:24). In some embodiments, a chimeric polypeptide comprises the sequence described in SEQ ID NO:29:

Seal leptin with amino acids 71-92 replaced with amino acids 73-94 (helix 3) of metreleptin, respectively:

(SEQ ID NO: 29)
PIQRVQDDTKTLIKTIITRINDISPPQGVCSRPRVAGLDFIPRVQSVRT

LSGMDQILATYQQILTSLQSRNVIQISNDLENLRDLLHVLAFSKSCPVP

RARGSDTIKGLGNVLRASVHSTEVVALSRLKAALQDMLRQLDRNPGC.

In some embodiments, a chimeric polypeptide comprises the amino acid sequence of a wild type seal leptin polypeptide with an N-terminal methionine (SEQ ID NO:31), wherein the contiguous region spanning the amino acids at positions 71-92 of SEQ ID NO:31 has been replaced with a contiguous region spanning the amino acids at positions 73-94 of A100 (SEQ ID NO:24). In some embodiments, a chimeric polypeptide comprises the sequence described in SEQ ID NO:32:

Seal leptin with N-terminal methionine, and with amino acids 71-92 replaced with amino acids 73-94 (helix 3) of metreleptin, respectively:

(SEQ ID NO: 32)
MPIQRVQDDTKTLIKTIITRINDISPPQGVCSRPRVAGLDFIPRVQSVR

TLSGMDQILATYQQILTSLQSRNVIQISNDLENLRDLLHVLAFSKSCPV

PRARGSDTIKGLGNVLRASVHSTEVVALSRLKAALQDMLRQLDRNPGC.

D. Chimeric Polypeptides Incorporating Human Helix 4

The Helix 4 region of a mature human leptin polypeptide spans a contiguous region of 22 amino acids. Helix 4 is thought to form parts of Binding Site I and Binding Site III of leptin, both of which are important for receptor activation. See, for example, Peelman et al., 2004, J. Biol. Chem. 279: 41038.

In one aspect, the present disclosure relates to chimeric polypeptides that are based on wild type seal leptin with an incorporated helix 4 sequence from mature human leptin. In some embodiments, a chimeric polypeptide comprises the amino acid sequence of a wild type seal leptin polypeptide (SEQ ID NO:28), wherein the contiguous region spanning the amino acids at positions 120-141 of SEQ ID NO:28 has been replaced with a contiguous region spanning the amino acids at positions 122-143 of A100 (SEQ ID NO:24). In some embodiments, a chimeric polypeptide comprises the sequence described in SEQ ID NO:56:

Seal leptin with amino acids 120-141 replaced with amino acids 122-143 (helix 4) of metreleptin, respectively:

(SEQ ID NO: 56)
PIQRVQDDTKTLIKTIITRINDISPPQGVCSRPRVAGLDFIPRVQSVRT

LSGMDQILATYQQILTSLQSRSVVQIANDLANLRALLRLLASAKSCPVP

RARGSDTIKGLGNVLRASVHSTEVVALSRLQGSLQDMLWQLDLNPGC.

In some embodiments, a chimeric polypeptide comprises the amino acid sequence of a wild type seal leptin polypeptide with an N-terminal methionine (SEQ ID NO:31), wherein the contiguous region spanning the amino acids at positions 120-141 of SEQ ID NO:31 has been replaced with a contiguous region spanning the amino acids at positions 122-143 of A100 (SEQ ID NO:24). In some embodiments, a chimeric polypeptide comprises the sequence described in SEQ ID NO:57:

Seal leptin with N-terminal methionine, and with amino acids 120-141 replaced with amino acids 122-143 (helix 4) of metreleptin, respectively:

(SEQ ID NO: 57)
MPIQRVQDDTKTLIKTIITRINDISPPQGVCSRPRVAGLDFIPRVQSVR

TLSGMDQILATYQQILTSLQSRSVVQIANDLANLRALLRLLASAKSCPV

PRARGSDTIKGLGNVLRASVHSTEVVALSRLQGSLQDMLWQLDLNPGC.

E. Chimeric Polypeptides Incorporating Human AB Loop

The AB Loop region of a mature human leptin polypeptide spans a contiguous region of 27 amino acids. The AB Loop is thought to form part of Binding Site III as well as a small portion of Binding Site I of leptin. See, for example, Peelman et al., 2004, J. Biol. Chem. 279: 41038. This region also contains the absolutely conserved motif GLDFIP (SEQ ID NO: 164).

In one aspect, the present disclosure relates to chimeric polypeptides that are based on wild type seal leptin with an incorporated AB Loop sequence from mature human leptin. In some embodiments, a chimeric polypeptide comprises the amino acid sequence of a wild type seal leptin polypeptide (SEQ ID NO:28), wherein the contiguous region spanning the amino acids at positions 23-49 of SEQ ID NO:28 has been replaced with a contiguous region spanning the amino acids at positions 25-51 of A100 (SEQ ID NO:24). In some embodiments, a chimeric polypeptide comprises the sequence described in SEQ ID NO:58:

Seal leptin with amino acids 23-49 replaced with amino acids 25-51 (AB loop) of metreleptin, respectively:

(SEQ ID NO: 58)
PIQRVQDDTKTLIKTIITRINDISHTQSVSSKQKVTGLDFIPGLHPILT

LSGMDQILATYQQILTSLQSRSVVQIANDLANLRALLRLLASAKSCPVP

RARGSDTIKGLGNVLRASVHSTEVVALSRLKAALQDMLRQLDRNPGC.

In some embodiments, a chimeric polypeptide comprises the amino acid sequence of a wild type seal leptin polypeptide with an N-terminal methionine (SEQ ID NO:31), wherein the contiguous region spanning the amino acids at positions 23-49 of SEQ ID NO:31 has been replaced with a contiguous region spanning the amino acids at positions 25-51 of A100 (SEQ ID NO:24). In some embodiments, a chimeric polypeptide comprises the sequence described in SEQ ID NO:59:

Seal leptin with N-terminal methionine, and with amino acids 23-49 replaced with amino acids 25-51 (AB loop) of metreleptin, respectively:

(SEQ ID NO: 59)
MPIQRVQDDTKTLIKTIITRINDISHTQSVSSKQKVTGLDFIPGLHPIL

TLSGMDQILATYQQILTSLQSRSVVQIANDLANLRALLRLLASAKSCPV

PRARGSDTIKGLGNVLRASVHSTEVVALSRLKAALQDMLRQLDRNPGC.

F. Chimeric Polypeptides Incorporating Human Loop 3-4

The Loop 3-4 region of a mature human leptin polypeptide spans a contiguous region of 27 amino acids. Loop 3-4 is thought to contain a part of Binding Site III of leptin to its receptor. See, for example, Peelman et al., 2004, J. Biol. Chem. 279: 41038.

In one aspect, the present disclosure relates to chimeric polypeptides that are based on wild type seal leptin with an incorporated Loop 3-4 sequence from mature human leptin. In some embodiments, a chimeric polypeptide comprises the amino acid sequence of a wild type seal leptin polypeptide (SEQ ID NO:28), wherein the contiguous region spanning the amino acids at positions 93-119 of SEQ ID NO:28 has been replaced with a contiguous region spanning the amino acids at positions 95-121 of A100 (SEQ ID NO:24). In some embodiments, a chimeric polypeptide comprises the sequence described in SEQ ID NO:60:

Seal leptin with amino acids 93-119 replaced with amino acids 95-121 (loop 3-4) of metreleptin, respectively:

(SEQ ID NO: 60)
PIQRVQDDTKTLIKTIITRINDISPPQGVCSRPRVAGLDFIPRVQSVRT

LSGMDQILATYQQILTSLQSRSVVQIANDLANLRALLRLLASAKSCHLP

WASGLETLDSLGGVLEASGYSTEVVALSRLKAALQDMLRQLDRNPGC.

In some embodiments, a chimeric polypeptide comprises the amino acid sequence of a wild type seal leptin polypeptide with an N-terminal methionine (SEQ ID NO:31), wherein the contiguous region spanning the amino acids at positions 93-119 of SEQ ID NO:31 has been replaced with a contiguous region spanning the amino acids at positions 95-121 of A100 (SEQ ID NO:24). In some embodiments, a chimeric polypeptide comprises the sequence described in SEQ ID NO:61:

Seal leptin with N-terminal methionine, and with amino acids 93-119 replaced with amino acids 95-121 (loop 3-4) of metreleptin, respectively:

(SEQ ID NO: 61)
MPIQRVQDDTKTLIKTIITRINDISPPQGVCSRPRVAGLDFIPRVQSVR

TLSGMDQILATYQQILTSLQSRSVVQIANDLANLRALLRLLASAKSCHL

PWASGLETLDSLGGVLEASGYSTEVVALSRLKAALQDMLRQLDRNPGC.

G. Chimeric Combination Polypeptides

In another aspect of the present disclosure, a series of chimeric combination polypeptides are described. These chimeric combination polypeptides are based on a wild type seal leptin polypeptide wherein two or more contiguous regions of 1-30 amino acids of a wild type seal leptin sequence (for example, SEQ ID NO:28 or SEQ ID NO:31) have been replaced at each region with a contiguous region of 1-30 amino acids of a mature human leptin sequence. Chimeric combination polypeptides can be engineered to demonstrate enhanced physical properties compared to the mature human leptin polypeptides which are used to derive the sequences, while retaining the biological activity of human leptin.

In some embodiments, the present disclosure relates to chimeric polypeptides that are based on wild type seal leptin with an incorporated helix 1 sequence and an incorporated helix 3 sequence from mature human leptin. In some embodiments, a chimeric polypeptide comprises the amino acid sequence of a wild type seal leptin polypeptide (SEQ ID NO:28), wherein the contiguous region spanning the amino acids at positions 3-22 of SEQ ID NO:28 has been replaced with a contiguous region spanning the amino acids at positions 5-24 of A100 (SEQ ID NO:24), and the contiguous region spanning the amino acids at positions 71-92 of SEQ ID NO:28 has been replaced with a contiguous region spanning the amino acids at positions 73-94 of A100 (SEQ ID NO:24). In some embodiments, a chimeric polypeptide comprises the sequence described in SEQ ID NO:62:

Seal leptin with amino acids 3-22 replaced with amino acids 5-24 (helix 1) of metreleptin, and amino acids 71-92 replaced with amino acids 73-94 (helix 3) of metreleptin, respectively:

(SEQ ID NO: 62)
PIQKVQDDTKTLIKTIVTRINDISPPQGVCSRPRVAGLDFIPRVQSVRT

LSGMDQILATYQQILTSLQSRNVIQISNDLENLRDLLHVLAFSKSCPVP

RARGSDTIKGLGNVLRASVHSTEVVALSRLKAALQDMLRQLDRNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 3-22 of SEQ ID NO:31 has been replaced with a contiguous region spanning the amino acids at positions 5-24 of A100 (SEQ ID NO:24), and the contiguous region spanning the amino acids at positions 71-92 of SEQ ID NO:31 has been replaced with a contiguous region spanning the amino acids at positions 73-94 of A100 (SEQ ID NO:24). In some embodiments, a chimeric polypeptide comprises the sequence described in SEQ ID NO:63:

Seal leptin with N-terminal methionine, and with amino acids 3-22 replaced with amino acids 5-24 (helix 1) of metreleptin, and amino acids 72-93 replaced with amino acids 73-94 (helix 3) of metreleptin, respectively:

(SEQ ID NO: 63)
MPIQKVQDDTKTLIKTIVTRINDISPPQGVCSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC

In some embodiments, the present disclosure relates to chimeric polypeptides that are based on wild type seal leptin with an incorporated helix 3 sequence and an incorporated AB Loop sequence from mature human leptin. In some embodiments, a chimeric polypeptide comprises the amino acid sequence of a wild type seal leptin polypeptide (SEQ ID NO:28), wherein the contiguous region spanning the amino acids at positions 71-92 of SEQ ID NO:28 has been replaced with a contiguous region spanning the amino acids at positions 73-94 of A100 (SEQ ID NO:24), and the contiguous region spanning the amino acids at positions 23-49 of SEQ ID NO:28 has been replaced with a contiguous region spanning the amino acids at positions 25-51 of A100 (SEQ ID NO:24). In some embodiments, a chimeric polypeptide comprises the sequence described in SEQ ID NO:64:

Seal leptin with amino acids 71-92 replaced with amino acids 73-94 (helix 3) of metreleptin, and with amino acids 23-49 replaced with amino acids 25-51 (AB loop) of metreleptin, respectively:

(SEQ ID NO: 64)

PIQRVQDDTKTLIKTIITRINDISHTQSVSSKQKVTGLDFIPGLHPILTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 71-92 of SEQ ID NO:31 has been replaced with a contiguous region spanning the amino acids at positions 73-94 of A100 (SEQ ID NO:24), and the contiguous region spanning the amino acids at positions 23-49 of SEQ ID NO:31 has been replaced with a contiguous region spanning the amino acids at positions 25-51 of A100 (SEQ ID NO:24). In some embodiments, a chimeric polypeptide comprises the sequence described in SEQ ID NO:65:

Seal leptin with N-terminal methionine, and with amino acids 71-92 replaced with amino acids 73-94 (helix 3) of metreleptin, and with amino acids 23-49 replaced with amino acids 25-51 (AB loop) of metreleptin, respectively:

(SEQ ID NO: 65)

MPIQRVQDDTKTLIKTIITRINDISHTQSVSSKQKVTGLDFIPGLHPILT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC

In some embodiments, the present disclosure relates to chimeric polypeptides that are based on wild type seal leptin with an incorporated helix 3 sequence and an incorporated Loop 3-4 sequence from mature human leptin. In some embodiments, a chimeric polypeptide comprises the amino acid sequence of a wild type seal leptin polypeptide (SEQ ID NO:28), wherein the contiguous region spanning the amino acids at positions 71-92 of SEQ ID NO:28 has been replaced with a contiguous region spanning the amino acids at positions 73-94 of A100 (SEQ ID NO:24), and the contiguous region spanning the amino acids at positions 93-119 of SEQ ID NO:28 has been replaced with a contiguous region spanning the amino acids at positions 95-121 of A100 (SEQ ID NO:24). In some embodiments, a chimeric polypeptide comprises the sequence described in SEQ ID NO:66:

Seal leptin with amino acids 71-92 replaced with amino acids 73-94 (helix 3) of metreleptin, and with amino acids 93-119 replaced with amino acids 95-121 (loop 3-4) of metreleptin, respectively:

(SEQ ID NO: 66)

PIQRVQDDTKTLIKTIITRINDISPPQGVCSRPRVAGLDFIPRVQSVRTL

SGMDQILATYQQILTSLQSRNVIQISNDLENLRDLLHVLAFSKSCHLPWA

SGLETLDSLGGVLEASGYSTEVVALSRLKAALQDMLRQLDRNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 71-92 of SEQ ID NO:31 has been replaced with a contiguous region spanning the amino acids at positions 73-94 of A100 (SEQ ID NO:24), and the contiguous region spanning the amino acids at positions 93-119 of SEQ ID NO:31 has been replaced with a contiguous region spanning the amino acids at positions 95-121 of A100 (SEQ ID NO:24). In some embodiments, a chimeric polypeptide comprises the sequence described in SEQ ID NO:67:

Seal leptin with N-terminal methionine, with amino acids 71-92 replaced with amino acids 73-94 (helix 3) of metreleptin, and with amino acids 93-119 replaced with amino acids 95-121 (loop 3-4) of metreleptin, respectively:

(SEQ ID NO: 67)

MPIQRVQDDTKTLIKTIITRINDISPPQGVCSRPRVAGLDFIPRVQSVRT

LSGMDQILATYQQILTSLQSRNVIQISNDLENLRDLLHVLAFSKSCHLPW

ASGLETLDSLGGVLEASGYSTEVVALSRLKAALQDMLRQLDRNPGC

In some embodiments, the present disclosure relates to chimeric polypeptides that are based on wild type seal leptin with an incorporated AB Loop sequence and an incorporated helix 4 sequence from mature human leptin. In some embodiments, a chimeric polypeptide comprises the amino acid sequence of a wild type seal leptin polypeptide (SEQ ID NO:28), wherein the contiguous region spanning the amino acids at positions 23-49 of SEQ ID NO:28 has been replaced with a contiguous region spanning the amino acids at positions 25-51 of A100 (SEQ ID NO:24), and the contiguous region spanning the amino acids at positions 120-141 of SEQ ID NO:28 has been replaced with a contiguous region spanning the amino acids at positions 122-143 of A100 (SEQ ID NO:24). In some embodiments, a chimeric polypeptide comprises the sequence described in SEQ ID NO:68:

Seal leptin with amino acids 23-49 replaced with amino acids 25-51 (AB loop) of metreleptin, and with amino acids 120-141 replaced with amino acids 122-143 (helix 4) of metreleptin, respectively:

(SEQ ID NO: 68)
PIQRVQDDTKTLIKTIITRINDISHTQSVSSKQKVTGLDFIPGLHPILTL

SGMDQILATYQQILTSLQSRSVVQIANDLANLRALLRLLASAKSCPVPRA

RGSDTIKGLGNVLRASVHSTEVVALSRLQGSLQDMLWQLDLNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 23-49 of SEQ ID NO:31 has been replaced with a contiguous region spanning the amino acids at positions 25-51 of A100 (SEQ ID NO:24), and the contiguous region spanning the amino acids at positions 120-141 of SEQ ID NO:31 has been replaced with a contiguous region spanning the amino acids at positions 122-143 of A100 (SEQ ID NO:24). In some embodiments, a chimeric polypeptide comprises the sequence described in SEQ ID NO:69:

Seal leptin with N-terminal methionine, with amino acids 23-49 replaced with amino acids 25-51 (AB loop) of metreleptin, and with amino acids 120-141 replaced with amino acids 122-143 (helix 4) of metreleptin, respectively:

(SEQ ID NO: 69)
MPIQRVQDDTKTLIKTIITRINDISHTQSVSSKQKVTGLDFIPGLHPILT

LSGMDQILATYQQILTSLQSRSVVQIANDLANLRALLRLLASAKSCPVPR

ARGSDTIKGLGNVLRASVHSTEVVALSRLQGSLQDMLWQLDLNPGC

In some embodiments, the present disclosure relates to chimeric polypeptides that are based on wild type seal leptin with an incorporated AB Loop sequence and an incorporated Loop 3-4 sequence from mature human leptin. In some embodiments, a chimeric polypeptide comprises the amino acid sequence of a wild type seal leptin polypeptide (SEQ ID NO:28), wherein the contiguous region spanning the amino acids at positions 23-49 of SEQ ID NO:28 has been replaced with a contiguous region spanning the amino acids at positions 25-51 of A100 (SEQ ID NO:24), and the contiguous region spanning the amino acids at positions 93-119 of SEQ ID NO:28 has been replaced with a contiguous region spanning the amino acids at positions 95-121 of A100 (SEQ ID NO:24). In some embodiments, a chimeric polypeptide comprises the sequence described in SEQ ID NO:70:

Seal leptin with amino acids 23-49 replaced with amino acids 25-51 (AB loop) of metreleptin, and with amino acids 93-119 replaced with amino acids 95-121 (loop 3-4) of metreleptin, respectively:

(SEQ ID NO: 70)
PIQRVQDDTKTLIKTIITRINDISHTQSVSSKQKVTGLDFIPGLHPILTL

SGMDQILATYQQILTSLQSRSVVQIANDLANLRALLRLLASAKSCHLPWA

SGLETLDSLGGVLEASGYSTEVVALSRLKAALQDMLRQLDRNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 23-49 of SEQ ID NO:31 has been replaced with a contiguous region spanning the amino acids at positions 25-51 of A100 (SEQ ID NO:24), and the contiguous region spanning the amino acids at positions 93-119 of SEQ ID NO:31 has been replaced with a contiguous region spanning the amino acids at positions 95-121 of A100 (SEQ ID NO:24). In some embodiments, a chimeric polypeptide comprises the sequence described in SEQ ID NO:71:

Seal leptin with N-terminal methionine, with amino acids 23-49 replaced with amino acids 25-51 (AB loop) of metreleptin, and with amino acids 93-119 replaced with amino acids 95-121 (loop 3-4) of metreleptin, respectively:

(SEQ ID NO: 71)
MPIQRVQDDTKTLIKTIITRINDISHTQSVSSKQKVTGLDFIPGLHPILT

LSGMDQILATYQQILTSLQSRSVVQIANDLANLRALLRLLASAKSCHLPW

ASGLETLDSLGGVLEASGYSTEVVALSRLKAALQDMLRQLDRNPGC.

In some embodiments, the present disclosure relates to chimeric polypeptides that are based on wild type seal leptin with an incorporated AB Loop sequence, an incorporated Loop 3-4 sequence, and an incorporated helix 3 sequence from mature human leptin. In some embodiments, a chimeric polypeptide comprises the amino acid sequence of a wild type seal leptin polypeptide (SEQ ID NO:28), wherein the contiguous region spanning the amino acids at positions 23-49 of SEQ ID NO:28 has been replaced with a contiguous region spanning the amino acids at positions 25-51 of A100 (SEQ ID NO:24), the contiguous region spanning the amino acids at positions 93-119 of SEQ ID NO:28 has been replaced with a contiguous region spanning the amino acids at positions 95-121 of A100 (SEQ ID NO:24), and the contiguous region spanning the amino acids at positions 71-92 of SEQ ID NO:28 has been replaced with a contiguous region spanning the amino acids at positions 73-94 of A100 (SEQ ID NO:24). In some embodiments, a chimeric polypeptide comprises the sequence described in SEQ ID NO:72:

Seal leptin with amino acids 23-49 replaced with amino acids 25-51 (AB loop) of metreleptin, with amino acids 93-119 replaced with amino acids 95-121 (loop 3-4) of metreleptin, and with amino acids 71-92 replaced with amino acids 73-94 (helix 3) of metreleptin, respectively:

(SEQ ID NO: 72)
PIQRVQDDTKTLIKTIITRINDISHTQSVSSKQKVTGLDFIPGLHPILTL

SGMDQILATYQQILTSLQSRNVIQISNDLENLRDLLHVLAFSKSCHLPWA

SGLETLDSLGGVLEASGYSTEVVALSRLKAALQDMLRQLDRNPGC

In some embodiments, a chimeric polypeptide comprises the amino acid sequence of a wild type seal leptin polypeptide with an N-terminal methionine (SEQ ID NO:31), wherein the contiguous region spanning the amino acids at positions 23-49 of SEQ ID NO:31 has been replaced with a contiguous region spanning the amino acids at positions 25-51 of A100 (SEQ ID NO:24), the contiguous region spanning the amino acids at positions 93-119 of SEQ ID NO:31 has been replaced with a contiguous region spanning the amino acids at positions 95-121 of A100 (SEQ ID NO:24), and the contiguous region spanning the amino acids at positions 71-92 of SEQ ID NO:28 has been replaced with a contiguous region spanning the amino acids at positions 73-94 of A100 (SEQ ID NO:24). In some embodiments, a chimeric polypeptide comprises the sequence described in SEQ ID NO:73:

Seal leptin with N-terminal methionine, with amino acids 23-49 replaced with amino acids 25-51 (AB loop) of metreleptin, with amino acids 93-119 replaced with amino acids 95-121 (loop 3-4) of metreleptin, and with amino acids 71-92 replaced with amino acids 73-94 (helix 3) of metreleptin, respectively:

(SEQ ID NO: 73)
MPIQRVQDDTKTLIKTIITRINDISHTQSVSSKQKVTGLDFIPGLHPILT

LSGMDQILATYQQILTSLQSRNVIQISNDLENLRDLLHVLAFSKSCHLPW

ASGLETLDSLGGVLEASGYSTEVVALSRLKAALQDMLRQLDRNPGC.

In some embodiments, the chimeric polypeptides provided by the invention contain a Cys to Ser amino acid substitution at position 30 of the wild type seal polypeptide sequence. According to some embodiments, the following chimeric polypeptides are provided:

Seal leptin with amino acids 30 and 3-22 replaced with amino acids 32 and 5-24 (helix 1) of metreleptin, respectively:

(SEQ ID NO: 74)
PIQKVQDDTKTLIKTIVTRINDISPPQGVSSRPRVAGLDFIPRVQSVRTL

SGMDQILATYQQILTSLQSRSVVQIANDLANLRALLRLLASAKSCPVPRA

RGSDTIKGLGNVLRASVHSTEVVALSRLKAALQDMLRQLDRNPGC.

Seal leptin with N-terminal methionine, and with amino acids 30 and 3-22 replaced with amino acids 32 and 5-24 (helix 1) of metreleptin, respectively:

(SEQ ID NO: 75)
MPIQKVQDDTKTLIKTIVTRINDISPPQGVSSRPRVAGLDFIPRVQSVRT

LSGMDQILATYQQILTSLQSRSVVQIANDLANLRALLRLLASAKSCPVPR

ARGSDTIKGLGNVLRASVHSTEVVALSRLKAALQDMLRQLDRNPGC.

Seal leptin with amino acids 30 and 50-65 replaced with amino acids 32 and 52-67 (helix 2) of metreleptin, respectively:

(SEQ ID NO: 76)
PIQRVQDDTKTLIKTIITRINDISPPQGVSSRPRVAGLDFIPRVQSVRTL

SKMDQTLAVYQQILTSLQSRSVVQIANDLANLRALLRLLASAKSCPVPRA

RGSDTIKGLGNVLRASVHSTEVVALSRLKAALQDMLRQLDRNPGC.

Seal leptin with N-terminal methionine, and with amino acids 30 and 50-65 replaced with amino acids 32 and 52-67 (helix 2) of metreleptin, respectively:

(SEQ ID NO: 77)
MPIQRVQDDTKTLIKTIITRINDISPPQGVSSRPRVAGLDFIPRVQSVRT

LSKMDQTLAVYQQILTSLQSRSVVQIANDLANLRALLRLLASAKSCPVPR

ARGSDTIKGLGNVLRASVHSTEVVALSRLKAALQDMLRQLDRNPGC.

Seal leptin with amino acids 30 and 71-92 replaced with amino acids 32 and 73-94 (helix 3) of metreleptin, respectively:

(SEQ ID NO: 30)
PIQRVQDDTKTLIKTIITRINDISPPQGVSSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC.

Seal leptin with N-terminal methionine, and with amino acids 30 and 71-92 replaced with amino acids 32 and 73-94 (helix 3) of metreleptin, respectively:

(SEQ ID NO: 33)
MPIQRVQDDTKTLIKTIITRINDISPPQGVSSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC.

Seal leptin with amino acids 30 and 120-141 replaced with amino acids 32 and 122-143 (helix 4) of metreleptin, respectively:

(SEQ ID NO: 78)
PIQRVQDDTKTLIKTIITRINDISPPQGVSSRPRVAGLDFIPRVQSVRTL

SGMDQILATYQQILTSLQSRSVVQIANDLANLRALLRLLASAKSCPVPRA

RGSDTIKGLGNVLRASVHSTEVVALSRLQGSLQDMLWQLDLNPGC.

Seal leptin with N-terminal methionine, and with amino acids 30 and 120-141 replaced with amino acids 32 and 122-143 (helix 4) of metreleptin, respectively:

(SEQ ID NO: 79)
MPIQRVQDDTKTLIKTIITRINDISPPQGVSSRPRVAGLDFIPRVQSVRT

LSGMDQILATYQQILTSLQSRSVVQIANDLANLRALLRLLASAKSCPVPR

ARGSDTIKGLGNVLRASVHSTEVVALSRLQGSLQDMLWQLDLNPGC.

Seal leptin with amino acids 30 and 93-119 replaced with amino acids 32 and 95-121 (loop 3-4) of metreleptin, respectively:

(SEQ ID NO: 80)
PIQRVQDDTKTLIKTIITRINDISPPQGVSSRPRVAGLDFIPRVQSVRTL

SGMDQILATYQQILTSLQSRSVVQIANDLANLRALLRLLASAKSCHLPWA

SGLETLDSLGGVLEASGYSTEVVALSRLKAALQDMLRQLDRNPGC.

Seal leptin with N-terminal methionine, and with amino acids 30 and 93-119 replaced with amino acids 32 and 95-121 (loop 3-4) of metreleptin, respectively:

(SEQ ID NO: 81)
MPIQRVQDDTKTLIKTIITRINDISPPQGVSSRPRVAGLDFIPRVQSVRT

LSGMDQILATYQQILTSLQSRSVVQIANDLANLRALLRLLASAKSCHLPW

ASGLETLDSLGGVLEASGYSTEVVALSRLKAALQDMLRQLDRNPGC.

Seal leptin with amino acid 30 replaced with amino acid 32, amino acids 3-22 replaced with amino acids 5-24 (helix 1) of metreleptin, and amino acids 71-92 replaced with amino acids 73-94 (helix 3) of metreleptin, respectively:

(SEQ ID NO: 82)
PIQKVQDDTKTLIKTIVTRINDISPPQGVSSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC

Seal leptin with N-terminal methionine, and with amino acid 30 replaced with amino acid 32, amino acids 3-22 replaced with amino acids 5-24 (helix 1) of metreleptin, and amino acids 72-93 replaced with amino acids 73-94 (helix 3) of metreleptin, respectively:

(SEQ ID NO: 83)
MPIQKVQDDTKTLIKTIVTRINDISPPQGVSSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC

Seal leptin with amino acid 30 replaced with amino acid 32, amino acids 71-92 replaced with amino acids 73-94 (helix 3) of metreleptin, and with amino acids 93-119 replaced with amino acids 95-121 (loop 3-4) of metreleptin, respectively:

(SEQ ID NO: 84)
PIQRVQDDTKTLIKTIITRINDISPPQGVSSRPRVAGLDFIPRVQSVRTL

SGMDQILATYQQILTSLQSRNVIQISNDLENLRDLLHVLAFSKSCHLPWA

SGLETLDSLGGVLEASGYSTEVVALSRLKAALQDMLRQLDRNPGC

Seal leptin with N-terminal methionine, with amino acid 30 replaced with amino acid 32, amino acids 71-92 replaced with amino acids 73-94 (helix 3) of metreleptin, and with amino acids 93-119 replaced with amino acids 95-121 (loop 3-4) of metreleptin, respectively:

(SEQ ID NO: 85)
MPIQRVQDDTKTLIKTIITRINDISPPQGVSSRPRVAGLDFIPRVQSVRT

LSGMDQILATYQQILTSLQSRNVIQISNDLENLRDLLHVLAFSKSCHLPW

ASGLETLDSLGGVLEASGYSTEVVALSRLKAALQDMLRQLDRNPGC.

Further Embodiments

It is understood that each of the polypeptides disclosed herein are also contemplated to include (optionally) a methionine at the N-terminus in frame with the naturally-occurring first amino acid thereof. For example, metreleptin (leptin A100) consists of mature human leptin to which has been added an N-terminal methionine, as disclosed in SEQ ID NO:24. Similarly, a methionine residue may be included at the N-terminus of any of the amino acid sequences and Formulae disclosed herein throughout.

In some embodiments, chimeric polypeptide analogs are provided. A chimeric polypeptide analog can have at least 80%, for example 80%, 85%, 90%, 95%, 98% or even higher, sequence identity relative to a parent chimeric polypeptide. In some embodiments, the parent chimeric polypeptide is a polypeptide set out in SEQ ID NO:29, SEQ ID NO:30, SEQ ID NO:32, SEQ ID NO:33, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, ID NO:81, SEQ ID NO:82, SEQ ID NO:83, SEQ ID NO:84, or SEQ ID NO:85. Accordingly, in some embodiments, a chimeric polypeptide analog may have at least 80%, for example 80%, 85%, 90%, 95%, 98% or even higher, sequence identity relative to any chimeric polypeptide selected from the group consisting of SEQ ID NO:29, SEQ ID NO:30, SEQ ID NO:32, and SEQ ID NO:33. In some embodiments, a chimeric polypeptide analog may have at least 80%, for example 80%, 85%, 90%, 95%, 98% or even higher, sequence identity relative to the chimeric polypeptide set forth in SEQ ID NO:33. In some embodiments, a chimeric polypeptide analog may have at least 90% sequence identity relative to the a chimeric polypeptide set forth in SEQ ID NO:29, SEQ ID NO:30, SEQ ID NO:32, or SEQ ID NO:33. In some embodiments, a chimeric polypeptide analog may have at least 90% sequence identity relative to the chimeric polypeptide set forth in SEQ ID NO:33.

Additionally, chimeric polypeptide analogs may be designed, prepared, and used in accordance with the invention in which 1, 2, 3, 4, 5, 6, 7, 8, 9, 10, 11, 12, 13, 14, 15, 16, 17, 18, 19, 20 or even 21 amino acids of a chimeric polypeptide selected from the group consisting of: SEQ ID NO:29, SEQ ID NO:30, SEQ ID NO:32, SEQ ID NO:33, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, ID NO:81, SEQ ID NO:82, SEQ ID NO:83, SEQ ID NO:84, and SEQ ID NO:85; is/are substituted with another amino acid, such as a conservative amino acid or a non-conservative amino acid, or is/are otherwise altered. As customary in the art, the term "conservative" in the context of amino acid substitutions refers to substitution which maintains properties of charge type (e.g., anionic, cationic, neutral, polar and the like), hydrophobicity or hydrophilicity, bulk (e.g., van der Waals contacts and the like), and/or functionality (e.g., hydroxy, amine, sulfhydryl and the like). The term "non-conservative" refers to an amino acid substitution which is not conservative.

In another aspect, the invention provides chimeric polypeptide analogs comprising at least one contiguous region of 1-30 amino acids from a mature human leptin analog sequence that contains at least one amino acid substitution at a position where divergence is observed in a corresponding position in a leptin from another species.

As is understood in the art, for example, murine leptins, rat leptins, bovine leptins, porcine leptins, and rhesus monkey leptins, such as those disclosed herein, are each substantially homologous to human leptins; in particular, the mature forms of these leptins are substantially homologous to mature leptins, and further, particularly near the N-terminal portion of the protein. One may prepare analogs of such leptins, such as mature human leptin form 1 (SEQ ID NO:20) and metreleptin (SEQ ID NO:24), such as by substituting or otherwise altering amino acid residues at one or more positions in such sequences where divergence is observed in a corresponding mature mouse, rat, bovine, porcine, or rhesus monkey leptin. For example, mature human leptins (e.g., SEQ ID NO:20) elicits biological responses in, for example, mice, rat, and monkey). See, e.g., WO 98/28427, WO 2009/064298, US2007/0020284, US2008/0207512, and Murakami et al., 1995, *Biochem. Biophys. Res. Comm.* 209: 944-952. Because human mature leptins have biological activity in, e.g., such species, leptin analogs may be designed and prepared in which one or more amino acids at positions which are divergent at the corresponding position(s) in a leptin from one or more of such species are substituted with the amino acid(s) at such corresponding divergent positions.

For example, using a human mature leptin protein according to SEQ ID NO:20 wherein the first amino acid is valine and the amino acid at position 146 is cysteine, one may substitute with another amino acid one or more of the amino acids at positions 32, 35, 50, 64, 68, 71, 74, 77, 89, 97, 100, 101, 105, 106, 107, 108, 111, 112, 118, 136, 138, 142, and 145 with the corresponding amino acid(s) found at the corresponding position(s) in SEQ ID NO:2 in order to design and prepare leptin analogs comprised by the chimeric polypeptides in accordance with the invention. Additionally, one may also substitute another amino acid, such as a conservative amino acid or a non-conservative amino acid, into one or more of positions 32, 35, 50, 64, 68, 71, 74, 77, 89, 97, 100, 101, 105, 106, 107, 108, 111, 112, 118, 136, 138, 142, and 145 of, for example, SEQ ID NO:20 in order to design and prepare leptin analogs comprised by the chimeric polypeptides in accordance with the invention.

One may further prepare additional leptin analogs based on the mature rat leptin protein sequence (SEQ ID NO:16). See, e.g., WO 98/28427, US2007/0020284, and Murakami et al., 1995, Id., herein incorporated by reference in their entireties and for all purposes. Mature rat leptin differs from mature human leptin form 1 (SEQ ID NO:20) at the following positions: 4, 32, 33, 35, 50, 68, 71, 74, 77, 78, 89, 97, 100, 101, 102, 105, 106, 107, 108, 111, 112, 118, 136, 138 and 145. Accordingly, at one or more of such positions in SEQ ID NO:20, one may substitute the amino acid found at the corresponding position(s) found in mature rat leptin (SEQ ID NO:16) in order to design and prepare leptin analogs comprised by the chimeric polypeptides in accordance with the invention. Additionally, one may also substitute another amino acid, such as a conservative amino acid or a non-conservative amino acid, into one or more of positions 4, 32, 33, 35, 50, 68, 71, 74, 77, 78, 89, 97, 100, 101, 102, 105, 106, 107, 108, 111, 112, 118, 136, 138 and 145 of, for example, SEQ ID NO:20, in order to design and prepare leptin analogs comprised by the chimeric polypeptides in accordance with the invention.

The positions from both mature rat leptin (SEQ ID NO:16) and mature murine leptin form 1 (SEQ ID NO:2) which diverge from the mature human leptin form 1 (SEQ ID NO:20) are: 4, 32, 33, 35, 50, 64, 68, 71, 74, 77, 78, 89, 97, 100, 102, 105, 106, 107, 108, 111, 112, 118, 136, 138, 142, and 145. Accordingly, at one or more of such positions in SEQ ID NO:20, one may substitute the amino acid found at the corresponding position(s) found in mature rat leptin sequence (SEQ ID NO:16) or mature murine form 1 sequence (SEQ ID NO:2) in order to design and prepare leptin analogs comprised by the chimeric polypeptides in accordance with the invention. Additionally, one may also substitute another amino acid, such as a conservative amino acid or a non-conservative amino acid, into one or more of positions 4, 32, 33, 35, 50, 64, 68, 71, 74, 77, 78, 89, 97, 100, 102, 105, 106, 107, 108, 111, 112, 118, 136, 138, 142, and 145 in order to design and prepare leptin analogs comprised by the chimeric polypeptides in accordance with the invention.

In addition, the amino acids found in rhesus monkey mature leptin (SEQ ID NO:14) which diverge from mature human leptin form 1 (SEQ ID NO:20) are (with amino acid residues noted in parentheses in one letter amino acid abbreviation): 8 (S), 35 (R), 48(V), 53(Q), 60(I), 66(I), 67(N), 68((L), 89(L), 100(L), 108(E), 112 (D), and 118 (L). Since human mature leptins elicit a biological response in monkeys, a leptin, such as mature human leptin form 1 (SEQ ID NO:20) having one or more of the rhesus monkey divergent amino acids replaced with another amino acid, such as the amino acids in parentheses, may be employed in designing and preparing leptin analogs comprised by the chimeric polypeptides in accordance with the invention. It should be noted that certain rhesus divergent amino acids are also those found in, for example, the above mature murine leptin form 1 (positions 35, 68, 89, 100 and 112). Thus, one may prepare leptin analogs in which one or more amino acids at positions 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145 of, e.g., mature human leptin form 1 (SEQ ID NO:20) are replaced by the corresponding amino acid(s) at such position(s) in murine or rhesus monkey leptins (e.g., SEQ ID NO:2 and/or SEQ ID NO:14).

In accordance with the invention, chimeric polypeptide analogs may be designed and prepared to comprise contiguous regions of amino acids from human leptin analogs. In some embodiments, the invention provides chimeric polypeptide analogs based on a wild type seal leptin polypeptide wherein at least one contiguous region of 1-30 amino acids of a wild type seal leptin sequence has been replaced with a contiguous region of 1-30 amino acids of a mature human leptin analog sequence, and wherein the mature human leptin analog sequence contains at least one amino acid substitution at a position where divergence is observed in a corresponding position in a leptin from another species. Chimeric polypeptide analogs comprising two or more contiguous regions of 1-30 amino acids of a mature human leptin analog sequence are also provided.

Chimeric polypeptides to which a chemical moiety is attached are polypeptide derivatives. Derivatization of chimeric polypeptides by attachment of one or more chemical moieties has been found to provide some advantage under certain circumstances, such as increasing the stability and circulation time of the therapeutic protein and decreasing immunogenicity and propensity for, for example, generation of neutralizing antibodies and/or incidence of injection site reactions. See, e.g., WO 98/28427, US2007/0020284, U.S. Pat. No. 4,179,337, Davis et al., issued Dec. 18, 1979. For a review, see Abuchowski et al., in ENZYMES AS DRUGS. (J. S. Holcerberg and J. Roberts, eds. pp. 367-383 (1981)); Francis et al., Id.

Polypeptide derivatives may constitute polypeptides to which a chemical modification has been made of one or more of its amino acid side groups, α-carbon atoms, terminal amino group, or terminal carboxylic acid group. A chemical modification includes, but is not limited to, attaching one or more chemical moieties, creating new bonds, and removing one or more chemical moieties. Modifications at amino acid side groups include, without limitation, alkylation, acylation, ester formation, amide formation, maleimide coupling, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkylacyls, branched alkylacyls, alkylaryl-acyls. Modifications of the terminal carboxy group include, without limitation, the amide, lower alkyl amide, dialkyl amide, arylamide, alkylarylamide and lower alkyl ester modifications. Lower alkyl is $C_1$-$C_4$ alkyl. Furthermore, one or more side groups, or terminal groups, may be protected by protective groups known to the ordinarily-skilled synthetic chemist. The α-carbon of an amino acid may be mono- or dimethylated.

Such derivatives include polypeptides conjugated to one or more water soluble polymer molecules, such as polyethylene glycol ("PEG") or fatty acid chains of various lengths (e.g., stearyl, palmitoyl, octanoyl), by the addition of polyamino acids, such as poly-his, poly-arg, poly-lys, and poly-ala, or by addition of small molecule substituents include short alkyls and constrained alkyls (e.g., branched, cyclic, fused, adamantyl), and aromatic groups. In some embodiments, the water soluble polymer molecules will have a molecular weight ranging from about 500 Daltons to about 60,000 Daltons.

Such polymer-conjugations may occur singularly at the N- or C-terminus or at the side chains of amino acid residues within the sequence of a chimeric polypeptide as disclosed herein. Alternatively, there may be multiple sites of derivatization along the amino acid sequence of such a chimeric polypeptide. Substitution of one or more amino acids with lysine, aspartic acid, glutamic acid, or cysteine may provide additional sites for derivatization. See, e.g., U.S. Pat. Nos. 5,824,784 and 5,824,778. In some embodiments, a chimeric polypeptide may be conjugated to one, two, or three polymer molecules.

In some embodiments, the water soluble polymer molecules are linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In some embodiments, a chimeric polypeptide is conjugated to one, two, or three PEG molecules through an epsilon amino group on a lysine amino acid.

Polypeptide derivatives also include polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of a leptin. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group ("isocap"), an octanyl group, an octyl glycine group (denoted as "G(Oct)" or "octylGly"), an 8-aminooctanic acid group, a dansyl, and/or a Fmoc group. In some embodiments, cyclization can be through the formation of disulfide bridges. Alternatively, there may be multiple sites of chemical alteration along the polypeptide amino acid sequence.

In certain embodiments, chimeric polypeptides are chemically altered to include a Bolton-Hunter group. Bolton-Hunter reagents are known in the art ("Radioimmunoassay and related methods," A. E. Bolton and W. M. Hunter, Chapter 26 of HANDBOOK OF EXPERIMENTAL IMMUNOLOGY, VOLUME I, IMMUNOCHEMISTRY, edited by D. M. Weir, Blackwell Scientific Publications, 1986), and may be used to introduce tyrosine-like moieties with a neutral linkage, through amino-terminal α-amino groups or ε-amino groups of lysine. In some embodiments, the N-terminal end of a polypeptide is modified with a Bolton-Hunter group. In some embodiments, an internal lysine residue is modified with a Bolton-Hunter group. In some embodiments, there may be multiple sites of Bolton-Hunter modification along the polypeptide amino acid sequence. Bolton-Hunter reagents used for polypeptide modification are commercially available, and may include, but are not limited to, water-soluble Bolton-Hunter reagent, Sulfosuccinimidyl-3-[4-hydrophenyl]propionate (Pierce Biotechnology, Inc., Rockford, Ill.) and Bolton-Hunter reagent-2, N-Succinimidyl 3-(4-hydroxy-3-iodophenyl) Priopionate (Wako Pure Chemical Industries, Ltd., Japan, catalog #199-09341). An exemplary Bolton-Hunter group conjugated through an amide linkage to a polypeptide is illustrated below, wherein the dashed line passes through the amide bond:

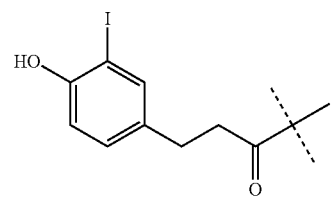

Polypeptides may be iodinated (such as radiolabeled with $^{125}$I) before or after Bolton-Hunter modification.

Polypeptide derivatives may include one or more modifications of a "non-essential" amino acid residue. In the context of the invention, a "non-essential" amino acid residue is a residue that can be altered, e.g., derivatized, without abolishing or substantially reducing the activity (e.g., the agonist activity) of the chimeric polypeptide. The chimeric polypeptides of the invention may include derivatizations of 1, 2, 3, 4, 5, 6, 7, 8, 9, 10 or more amino acid residues; of these, one or more amino acid residues may be non-essential amino acid residues. Additionally, the polypeptides of the invention may be derivatized such that they include additions of at least 1, 2, 3, 4, 5, 6, 7, 8, 9, 10 or more amino acids without abolishing or substantially reducing the activity of the polypeptide. Additionally, such non-essential amino acid residues may be substituted with an amino acid residue that is amenable to derivatization as described throughout.

As used throughout, "amino acid," "amino acid residue" and the like refer to natural amino acids, unnatural amino acids, and modified amino acids. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3- diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine Additional residues that can be incorporated are described in Sandberg et al., *J. Med. Chem.* 41: 2481-91, 1998.

As mentioned above, chemical moieties suitable for such derivatization of the chimeric polypeptides include, for example, various water soluble polymers. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the chimeric polypeptides, the effectiveness of the derivatization may be ascertained by administering the derivatized polypeptide, in the desired form (i.e., by osmotic pump, or, more preferably, by injection or infusion, or, further formulated for oral, pulmonary or nasal delivery, for example), and observing biological effects and biological responses as described herein.

Such a water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1, 3-dioxolane, poly-1,3,6-trioxane, ethylene/maleic anhydride copolymer, polyaminoacids (either homopolymers or random copolymers), and dextran or poly(n-vinyl pyrolidone)polyethylene glycol, propylene glycol homopolymers, polypropylene oxide/ethylene oxide co-polymers, polyoxyethylated polyols and polyvinyl alcohol. Polyethylene glycol propionaldehyde may have advantages in manufacturing due to its stability in water. Also, succinate, styrene, and hydroxyethyl starch may also be used.

Derivatives of chimeric polypeptides in accordance with the invention may be prepared by attaching polyaminoacids or branch point amino acids. For example, the polyaminoacid may be an additional carrier protein, such as an Fc moiety, which can serve to also increase the circulation half life of the chimeric polypeptide. Additionally, such polyaminoacids may be selected from the group consisting of serum albumin (such as human serum albumin), an additional antibody or portion thereof (e.g. the Fc region), or other polyaminoacids, e.g. polylysines. As indicated below, the location of attachment of the polyaminoacid may be at the N-terminus of polypeptide, or C-terminus, or other places in between, and also may be connected by a chemical "linker" moiety to the polypeptide, such as a peptidic linker or a non-peptidic linker.

The polymer may be of any molecular weight, and may be branched or unbranched. For polyethylene glycol, the preferred molecular weight is between about 2 kilodaltons (kDa) and about 100 kDa (the term "about" indicating that in preparations of polyethylene glycol, some molecules will weigh more, some less, than the stated molecular weight) for ease in handling and manufacturing. In certain embodiments, the polyethylene glycol is between about 2 kDa and about 60 kDa. In certain embodiments, the polyethylene glycol is between about 2 kDa and about 40 kDa. In certain embodiments, the polyethylene glycol is between about 5 kDa and about 40 kDa. In certain embodiments, the polyethylene glycol is between about 10 kDa and about 40 kDa. In certain embodiments, the polyethylene glycol is between about 5 kDa and about 30 kDa. In certain embodiments, the polyethylene glycol is between about 5 kDa and about 20 kDa. In certain embodiments, the polyethylene glycol is between about 10 kDa and about 20 kDa. Other sizes may be used, depending on the desired therapeutic profile (e.g., the duration of sustained release desired, solubility characteristics, the effects, if any, on biological activity, the ease in handling, the degree or lack of antigenicity and other known effects of the polyethylene glycol attached to a leptin and/or to a chimeric polypeptide of the invention). Additional considerations that may influence the selection of a PEG of a particular molecular weight which may be attached to a chimeric polypeptide to generate a chimeric derivative in accordance with the invention include the extent to which such a molecular weight PEG may: mitigate aggregation and/or increase the solubility of the chimeric polypeptide, when present in a pharmaceutically acceptable composition or formulation, or when exposed to physiological fluids or tissues upon administration to a subject (such as by injection); mitigate the incidence of injection site reactions caused by administration of the chimeric polypeptide upon administration to a subject by injection; mitigate the generation of neutralizing antibodies that may be raised against the chimeric polypeptide as a result of administration of such a chimeric polypeptide to a subject; and the like.

The number of polymer molecules so attached may vary, and one skilled in the art will be able to ascertain the resultant effect on function. One may mono-derivatize, or may provide for a di-, tri-, tetra- or some combination of derivatization, with the same or different chemical moieties (e.g., polymers, such as different weights of polyethylene glycols). The proportion of polymer molecules to chimeric polypeptide molecules to be derivatized will vary, as will their concentrations in the reaction mixture. In general, the optimum ratio, in terms of efficiency of reaction in that there is no excess unreacted chimeric polypeptide or polymer, will be determined by factors such as the desired degree of derivatization (e.g., mono, di-, tri-, etc.), the molecular weight of the polymer selected, whether the polymer is branched or unbranched, and the reaction conditions.

The chemical moieties should be attached to the chimeric polypeptide with consideration of the effects on functional or antigenic domains of the chimeric polypeptide. There are a number of attachment methods available to those skilled in the art. E.g., EP 0 401 384 herein incorporated by reference (coupling PEG to G-CSF), see also Malik et al., 1992, *Exp. Hematol.* 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

One may specifically desire to design and prepare N-terminally chemically modified chimeric polypeptides of the invention. Using polyethylene glycol as an illustration of the present compositions, one may select from a variety of polyethylene glycol molecules (by molecular weight, branching, etc.), the proportion of polyethylene glycol molecules to chimeric polypeptide molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

III. Methods of Design and Production

Design of constructs. The chimeric polypeptides described herein can be designed at the amino acid level. These sequences can then be back translated using a variety of software products known in the art such that the nucleotide sequence is optimized for the desired expression host, e.g. based protein expression, codon optimization, restriction site content. For example, the nucleotide sequence can be optimized for *E. coli* based protein expression and for restriction site content. Based on the nucleotide sequence of interest, overlapping oligonucleotides can be provided for multistep PCR, as known in the art. These oligonucleotides can be used in multiple PCR reactions under conditions well known in the art to build the cDNA encoding the protein of interest. For one example is 1× Amplitaq Buffer, 1.3 mM $MgCl_2$, 200 uM dNTPs, 4 U Amplitaq Gold, 0.2 uM of each primer (AmpliTaq Gold, ABI), with cycling parameters: (94 C:30 s, 58 C:1 min, 72 C:1 min), 35 cycles.

Restriction sites can be added to the ends of the PCR products for use in vector ligation as known in the art. Specific sites can include Nde1 and Xho1, such that the cDNA can then be in the proper reading frame in a pET45b expression vector (Novagen). By using these sites, any N-terminal His Tags that are in this vector can be removed as the translation start site would then be downstream of the tag. Once expression constructs are completed, verification can be conduct by sequencing using e.g., T7 promoter primer, T7 terminator primer and standard ABI BigDye Term v3.1 protocols as known in the art. Sequence information can be obtained from e.g., an ABI 3730 DNA Analyzer and can be analyzed using Vector NTI v.10 software (Invitrogen). Expression constructs can be designed in a modular manner such that linker sequences can be easily cut out and changed, as known in the art.

Protease recognition sites, known in the art or described herein, can be incorporated into constructs useful for the design, construction, manipulation and production of recombinant chimeric polypeptides described herein.

General methods of production. The chimeric polypeptides described herein may be prepared using biological, chemical, and/or recombinant DNA techniques that are known in the art. Exemplary methods are described herein and in U.S. Pat. No. 6,872,700; WO 2007/139941; WO 2007/140284; WO 2008/082274; WO 2009/011544; and US Publication No. 2007/0238669, the disclosures of which are incorporated herein by reference in their entireties and for all purposes. Other methods for preparing the compounds are set forth herein.

The chimeric polypeptides described herein may be prepared using standard solid-phase peptide synthesis techniques, such as an automated or semiautomated peptide synthesizer. The chimeric polypeptides may be produced by non-biological peptide synthesis using amino acids and/or amino acid derivatives having reactive side-chains protected, the non-biological peptide synthesis comprising stepwise coupling of the amino acids and/or the amino acid derivatives to form a polypeptide according to the first aspect having reactive side-chains protected, removing the protecting groups from the reactive side-chains of the polypeptide, and folding of the polypeptide in aqueous solution. Thus, normal amino acids (e.g. glycine, alanine, phenylalanine, isoleucine, leucine and valine) and pre-protected amino acid derivatives are used to sequentially build a polypeptide sequence, in solution or on a solid support in an organic solvent. When a complete polypeptide sequence is built, the protecting groups are removed and the polypeptide is allowed to fold in an aqueous solution.

Typically, using such techniques, an alpha-N-carbamoyl protected amino acid and an amino acid attached to the growing peptide chain on a resin are coupled at RT in an inert solvent (e.g., dimethylformamide, N-methylpyrrolidinone, methylene chloride, and the like) in the presence of coupling agents (e.g., dicyclohexylcarbodiimide, 1-hydroxybenzo-triazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from Applied Biosystems Inc. (Foster City, Calif.).

For chemical synthesis solid phase peptide synthesis can be used for the chimeric polypeptides, since in general solid phase synthesis is a straightforward approach with excellent scalability to commercial scale. Solid phase peptide synthesis may be carried out with an automatic peptide synthesizer (Model 430A, Applied Biosystems Inc., Foster City, Calif.)

using the NMP/HOBt (Option 1) system and tBoc or Fmoc chemistry (See Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may also be assembled using an Advanced Chem Tech Synthesizer (Model MPS 350, Louisville, Ky.).

The compounds described herein may also be prepared using recombinant DNA techniques using methods known in the art, such as Sambrook et al., 1989, MOLECULAR CLONING: A LABORATORY MANUAL, 2d Ed., Cold Spring Harbor. Non-peptide compounds may be prepared by art-known methods. For example, phosphate-containing amino acids and peptides containing such amino acids, may be prepared using methods known in the art, such as described in Bartlett et al, 1986, *Biorg. Chem.* 14:356-377.

The chimeric polypeptides may alternatively be produced by recombinant techniques well known in the art. See, e.g., Sambrook et al., 1989 (Id.). These chimeric polypeptides produced by recombinant technologies may be expressed from a polynucleotide. One skilled in the art will appreciate that the polynucleotides, including DNA and RNA, that encode such chimeric polypeptides may be obtained from the wild-type cDNA, e.g. human leptin, taking into consideration the degeneracy of codon usage, and may further be engineered as desired to incorporate the indicated substitutions. These polynucleotide sequences may incorporate codons facilitating transcription and translation of mRNA in microbial hosts. Such manufacturing sequences may readily be constructed according to the methods well known in the art. See, e.g., WO 83/04053, incorporated herein by reference in its entirety and for all purposes. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, 1986, *Bioorg. Chem.* 14: 356-77.

A variety of expression vector/host systems may be utilized to contain and express a chimeric polypeptide coding sequence. These include, but are not limited to, microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include, but are not limited to, VERO cells, HeLa cells, Chinese hamster ovary (CHO) cell lines, COS cells (such as COS-7), WI 38, BHK, HepG2, 3T3, RIN, MDCK, A549, PCl2, K562 and 293 cells. Exemplary protocols for the recombinant expression of the protein are described herein and/or are known in the art.

As such, polynucleotide sequences are useful in generating new and useful viral and plasmid DNA vectors, new and useful transformed and transfected prokaryotic and eukaryotic host cells (including bacterial, yeast, and mammalian cells grown in culture), and new and useful methods for cultured growth of such host cells capable of expression of the present chimeric polypeptides. The polynucleotide sequences encoding chimeric polypeptides herein may be useful for gene therapy in instances where underproduction of chimeric polypeptides would be alleviated, or the need for increased levels of such would be met.

The present invention also provides for processes for recombinant DNA production of the present chimeric polypeptides. Provided is a process for producing the chimeric polypeptides from a host cell containing nucleic acids encoding the chimeric polypeptide comprising: (a) culturing the host cell containing polynucleotides encoding the chimeric polypeptide under conditions facilitating the expression of the DNA molecule; and (b) obtaining the chimeric polypeptide.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, W138, and the like, have specific cellular machinery and characteristic mechanisms for such post-translational activities, and may be chosen to ensure the correct modification and processing of the introduced foreign protein.

Alternatively, a yeast system may be employed to generate the chimeric polypeptides of the present invention. The coding region of the chimeric polypeptides DNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, 1982, *Cell*, 30:933-43). The pre-pro-alpha leader coding sequence and chimeric polypeptide coding sequence fragments are ligated into a plasmid containing the yeast alcohol dehydrogenase (ADH2) promoter, such that the promoter directs expression of a fusion protein consisting of the pre-pro-alpha factor fused to the mature chimeric polypeptide. As taught by Rose and Broach, *Meth. Enz.* 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., 1990, *Meth. Enz.* 185: 280-297). The ADH2 promoter is induced upon exhaustion of glucose in the growth media (Price et al., 1987, *Gene* 55:287). The pre-pro-alpha sequence effects secretion of the fusion protein from the cells. Concomitantly, the yeast KEX2 protein cleaves the pre-pro sequence from the mature chimeric polypeptides (Bitter et al., 1984, *Proc. Natl. Acad. Sci. USA* 81:5330-5334).

Chimeric polypeptides of the invention may also be recombinantly expressed in yeast, e.g., *Pichia*, using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted chimeric polypeptide is purified from the yeast growth medium by, e.g., the methods used to purify said chimeric polypeptide from bacterial and mammalian cell supernatants.

Alternatively, the DNA encoding a chimeric polypeptide may be cloned into a baculovirus expression vector, e.g. pVL1393 (PharMingen, San Diego, Calif.). This chimeric-polypeptide-encoding vector is then used according to the manufacturer's directions (PharMingen) or known techniques to infect *Spodoptera frugiperda* cells, grown for example in sF9 protein-free media, and to produce recombinant protein. The protein is purified and concentrated from the media using methods known in the art, e.g. a heparin-Sepharose column (Pharmacia, Piscataway, N.J.) and sequential molecular sizing columns (Amicon, Beverly, Mass.), and resuspended in appropriate solution, e.g. PBS. SDS-PAGE analysis can be used to characterize the protein, for example by showing a single band that confirms the size of the desired chimeric polypeptide, as can full amino acid amino acid sequence analysis, e.g. Edman sequencing on a Proton 2090 Peptide Sequencer, or confirmation of its N-terminal sequence.

For example, the DNA sequence encoding the predicted mature chimeric polypeptide may be cloned into a plasmid containing a desired promoter and, optionally, a leader sequence (see, e.g., Better et al., 1988, *Science* 240:1041-1043). The sequence of this construct may be confirmed by automated sequencing. The plasmid is then transformed into *E. coli*, strain MC1061, using standard procedures employing CACl2 incubation and heat shock treatment of the bacteria (Sambrook et al., Id.). The transformed bacteria are grown in LB medium supplemented with carbenicillin, and production of the expressed protein is induced by growth in a suitable medium. If present, the leader sequence will affect secretion of the mature chimeric polypeptide and be cleaved during secretion. The secreted recombinant chimeric polypeptide is purified from the bacterial culture media by the method described herein.

Alternatively, the chimeric polypeptides may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. The chimeric polypeptide coding sequence is cloned into a nonessential region of the virus, such as the polyhedrin gene, and placed under control of the polyhedrin promoter. Successful insertion of a chimeric polypeptide will render the polyhedrin gene inactive and produce recombinant virus lacking coat protein coat. The recombinant viruses are then used to infect *S. frugiperda* cells or *Trichoplusia* larvae in which a chimeric polypeptide of the present invention is expressed (Smith et al., 1983, *J. Virol.* 46:584; Engelhard et al., 1994, *Proc. Natl. Acad. Sci.* USA 91:3224-3227).

In another example, the DNA sequence encoding the chimeric polypeptides may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3X/chimeric polypeptide construct is transformed into *E. coli* XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl beta-D-thiogalactopyranoside (Sigma Chemical Co., St. Louis, Mo.). Plasmid DNA from individual transformants is purified and partially sequenced using an automated sequencer to confirm the presence of the desired chimeric polypeptide-encoding gene insert in the proper orientation.

The fusion protein, when expected to be produced as an insoluble inclusion body in the bacteria, may be purified as described above or as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at RT. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/chimeric polypeptide fusion protein is produced in bacteria as a soluble protein, it may be purified using the GST Purification Module (Pharmacia Biotech).

The fusion protein may be subjected to digestion to cleave the GST from the mature chimeric polypeptide. The digestion reaction (20-40 μg fusion protein, 20-30 units human thrombin (4000 U/mg (Sigma) in 0.5 mL PBS) is incubated 16-48 hrs. at RT and loaded on a denaturing SDS-PAGE gel to fractionate the reaction products. The gel is soaked in 0.4 M KCl to visualize the protein bands. The identity of the protein band corresponding to the expected molecular weight of the chimeric polypeptide may be confirmed by partial amino acid sequence analysis using an automated sequencer (Applied Biosystems Model 473A, Foster City, Calif.).

In a particularly exemplary method of recombinant expression of the chimeric polypeptides of the present invention, 293 cells may be co-transfected with plasmids containing the chimeric polypeptides cDNA in the pCMV vector (5' CMV promoter, 3' HGH poly A sequence) and pSV2neo (containing the neo resistance gene) by the calcium phosphate method. In one embodiment, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for chimeric polypeptides expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk−, hgprt− or aprt− cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

The chimeric polypeptides of the present invention may be produced using a combination of both automated peptide synthesis and recombinant techniques. For example, a chimeric polypeptide of the present invention may contain a combination of modifications including deletion, substitution, insertion and derivatization by PEGylation (or other moiety, e.g. polymer, fatty acyl chain, C-terminal amidation). Such a chimeric polypeptide may be produced in stages. In the first stage, an intermediate chimeric polypeptide containing the modifications of deletion, substitution, insertion, and any combination thereof, may be produced by recombinant techniques as described. Then after an optional purification step as described herein, the intermediate chimeric polypeptide is PEGylated (or subjected to other chemical derivatization, e.g., acylation, C-terminal amidation) through chemical modification with an appropriate PEGylating reagent (e.g., from NeKtar Transforming Therapeutics, San Carlos, Calif.) to yield the desired chimeric polypeptide derivative. One skilled in the art will appreciate that the above-described procedure may be generalized to apply to a chimeric polypeptide containing a combination of modifications selected from deletion, substitution, insertion, derivation, and other means of modification well known in the art and contemplated by the present invention.

Peptides may be purified by any number of methods known in the art, including as described herein In one method peptides are purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen et al, THE PICO TAG METHOD: A MANUAL OF ADVANCED TECHNIQUES FOR AMINO ACID ANALYSIS, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Chimeric polypeptide expression assay. Methods are available for assaying the level of protein expression by a host cell. Procedures useful for assaying the level of protein expression by a host cell are exemplified in the following typical protocol. About 25 μl BL21 E. coli cells are transformed with 2 ul plasmid DNA (expression vector for the chimeric polynucleotide). Cells can be plated and incubated overnight at 37 degrees C. or at room temperature (RT) over a 48-hr period. A single colony can be selected and used to grow starter culture in 4 ml LB media with appropriate antibiotic for ~6 hrs. Glycerol stocks can be prepared by adding 100 ul 180% sterile glycerol to 900 ul stock, which can then be mixed gently and stored at −80 C. A 250 μl sample can be removed for TCP uninduced sample. An aliquot, for example, 2 ml of Magic media containing appropriate antibiotic can be inoculated with 5 μl starter culture, which can then be incubated overnight (up to 24 hrs) at 37 C, 300 rpm. As known in the art, Magic Media is autoinducing. Alternatively, 60 ml Magic Media containing appropriate antibiotic can be inoculated with 60 μl starter culture in a 250 ml or 125 ml Thompson flask, which can then be incubated overnight (up to 24 hrs) at 30 C, 300 rpm. After incubation, 250 μl culture can be removed from each tube and the cells pelleted. The cell can be resuspended in 1 ml 50 mM Tris pH 8, 150 mM NaCl, to which can be added 0.1 volumes (100 ul) POP culture reagent and 1 μl r-lysozyme (1:750 dilution in r-lysozyme buffer). The mixture can be mixed well and incubated at least 10 min at RT. The preparation can then be centrifuged 10 min at 14000×G. The supernatant (soluble fraction) can be removed and retained, and samples can be prepared for gel analysis (15 μl+5 μl LDS). The remaining inclusion body pellet can be resuspended in 1 ml 1% SDS with sonication. The sample can be prepared for gel analysis (15 ul+5 μl LDS). For uninduced samples, 1.0 volumes POP culture reagent and 1 μl r-lysozyme (1:750 dilution in r-lysozyme buffer) can be added. The mixture can be mixed well and incubated at least 10 min at RT. These samples may not need to be centrifuged. The sample can then be prepared for gel analysis (15 μl+5 μl LDS). NU-PAGE gels (4-12%) non-reduced in 1×MES buffer can be run and stained with SimplyBlue microwave protocol. Destaining can be conducted overnight, as known in the art. A gel image can be retained, and analyzed to determine protein expression levels.

Inclusion Body preparation. For chimeric polypeptides that are found in the inclusion body fraction, the following procedure can be beneficial. The cell pellet can be resuspended in a minimum of 100 ml Lysis buffer for each 50 ml culture. Upon the addition of 30 ml, a 10 ml pipette can be used to resuspend, then the tube can be washed out with an additional 70 ml. The resuspended cell solution can be multiply run, e.g., 4 passes, through a microfluidizer at 100 PSI (min) taking care to keep chamber in ice water through the entire process. The fluidized slurry can be centrifuged at 14000×g, 20 min (e.g., JLA 10.5, 10,000 rpm, using 250 ml Nalgene® bottles). The inclusion body pellet can be resuspended on ice in chilled lysis buffer with stir bar and stir plate for 1 hour at 4 C after disruption with pipette tip. The pellet can be resuspended a second time in distilled $H_2O$ with stir bar and stir plate for 1 hour at 4 C after disruption with pipette tip, followed by centrifugation at 14000×g, 15 min. The supernatant can be removed and discarded. The resultant can be stored at −80 C.

Protein purification. As described herein, numerous methods are known for isolation of expressed polypeptides. The following is one example. Inclusion body pellets can be solubilized in appropriate volume of solubilization buffer (8M urea or 8M guanidine, 50 mM Tris, 10 mM DTT, pH 7.75) for 1 hour at RT. The solubilized pellets can be centrifuged for 20 min at 27 000 g. Filtered (e.g., 0.4 um) supernatant can be transferred drop by drop into appropriate volume of refolding buffer (50 mM Tris-HCl, 1 M urea, 0.8 M arginine, 4 mM cysteine, 1 mM cystamine; pH 8) at RT. The result can then be placed at 4° C. overnight or longer with gentle mixing. Samples can be concentrated and run on a gel filtration column (Superdex™ 75 26/60) at 1-2 ml/min in 4 C environment using a GE Healthsciences AKTAFPLC™. Appropriate protein containing fractions can be identified via SDS-PAGE, pooled and run through a second gel filtration column. Pooled protein can then be concentrated in Amicon filter to appropriate concentration and assayed for endotoxin levels using, e.g., Endosafe® PTS Reader (Charles River), as known in the art. Once a protein sample has passed the endotoxin criteria, it can be sterile filtered, dispensed into aliquots and run through quality control assays. Quality control assays can include analytical HPLC-SEC, non reducing SDS PAGE and RP HPLC—MS to obtain approximate mass. Proteins can be obtained in 1×PBS (137 mM sodium chloride, 2.7 mM potassium chloride, 4.3 mM disodium phosphate, 1.4 mM monopotassium phosphate, pH7.2), distributed into aliquots and flash frozen for storage at −70 to −80° C.

IV. Methods of Use and Treating Disease

Indications. A variety of diseases and disorders are contemplated to be beneficially treated by the polypeptide compounds and methods described herein.

Obesity and overweight. Obesity and its associated disorders including overweight are common and serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. See, e.g., Kopelman, 2000, *Nature* 404:635-43.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease. See e.g., Rissanen et al, 1990, *Br. Med. J.,* 301:835-7. Obesity is also a risk factor for the group of conditions called insulin resistance syndrome, or "Syndrome X" and metabolic syndrome. The worldwide medical cost of obesity and associated disorders is enormous.

The pathogenesis of obesity is believed to be multifactoral. A problem is that, in obese subjects, nutrient availability and energy expenditure do not come into balance until there is excess adipose tissue. The central nervous system (CNS) controls energy balance and coordinates a variety of behavioral, autonomic and endocrine activities appropriate to the metabolic status of the animal. The mechanisms or systems that control these activities are broadly distributed across the forebrain (e.g., hypothalamus), hindbrain (e.g., brainstem), and spinal cord. Ultimately, metabolic (i.e., fuel availability) and cognitive (i.e., learned preferences) information from these systems is integrated and the decision to engage in appetitive (food seeking) and consummatory (ingestion) behaviors is either turned on (meal procurement and initiation) or turned off (meal termination). The hypothalamus is thought to be principally responsible for integrating these signals and then issuing commands to the brainstem. Brainstem nuclei that control the elements of the consummatory motor control system (e.g., muscles responsible for chewing and swallowing). As such, these CNS nuclei have literally been referred to as constituting the "final common pathway" for ingestive behavior.

Neuroanatomical and pharmacological evidence support that signals of energy and nutritional homeostasis integrate in forebrain nuclei and that the consummatory motor control system resides in brainstem nuclei, probably in regions surrounding the trigeminal motor nucleus. There are extensive reciprocal connection between the hypothalamus and brainstem. A variety of CNS-directed anti-obesity therapeutics (e.g., small molecules and peptides) focus predominantly upon forebrain substrates residing in the hypothalamus and/or upon hindbrain substrates residing in the brainstem.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health. Methods and therapies employing the chimeric peptides disclosed herein, either alone or in combination with other anti-obesity agents (see, e.g., WO 2009064298 and US 20080207512) may provide such beneficial effects.

Leptin deficiency. Leptin deficiency has been shown to result in obesity. One form of leptin deficiency is congenital leptin deficiency, a rare genetic disorder. See Montague et al., 1997, *Nature* 387: 903-908. Severe leptin deficiency can be a result of uncontrolled insulin-deficient diabetes mellitus that results from destruction of insulin-secreting β-cells. It is theorized that the lack of insulin leads to synthesis and storage of triglycerides in adipose tissue, which prevents weight gain and in turn dramatically reduces plasma leptin levels since leptin is synthesized in adipose tissue. These and other Leptin deficiencies, and disease and disorders that result from such deficiencies, can be treated with leptin replacement therapy, such as via daily leptin or leptin agonist injections. The chimeric polypeptides described herein can provide a more convenient and advantageous therapeutic treatment of such diseases and disorders.

Diabetes and cardiovascular disease. Diabetes mellitus is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

Understanding the high risk nature of diabetic/acute myocardial infarction patients, the American College of Cardiology/American Heart Association ("ACC/AHA") clinical practice guidelines for the management of hospitalized patients with unstable angina or non-ST-elevation myocardial infarction (collectively referred to as "ACS") recently recognized that hospitalized diabetic patients are a special population requiring aggressive management of hyperglycemia. Specifically, the guidelines state that glucose-lowering therapy for hospitalized diabetic/ACS patients should be targeted to achieve preprandial glucose less than 10 mg/dL, a maximum daily target than 180 mg/dL, and a post-discharge hemoglobin A1c less than 7%.

In a nationwide sample of elderly ACS patients, it was demonstrated that an increase in 30-day mortality in diabetic patients corresponded with the patients having higher glucose values upon admission to the hospital. See "Diabetic Coronary Artery Disease & Intervention," *Coronary Therapeutics* 2002, Oak Brook, Ill., Sep. 20, 2002. There is increasing evidence that sustained hyperglycemia rather than transient elevated glucose upon hospital admission is related to serious adverse events. Although the ideal metric for hyperglycemia and vascular risk in patients is not readily known, it appears that the mean glucose value during hospitalization is most predictive of mortality. In a separate study of ACS patients form over forty hospitals in the United States, it was found that persistent hyperglycemia, as opposed to random glucose values upon admission to the hospital, was more predictive of in-hospital mortality. See *Acute Coronary Syndrome Summit: A State of the Art Approach*, Kansas City, Mo., Sep. 21, 2002. Compared with glucose values upon admission, a logistic regression model of glucose control over the entire hospitalization was most predictive of mortality. There was nearly a two-fold increased risk of mortality during hospitalization for each 10 mg/dL increase in glucose over 120 mg/dL. In a smaller cohort of consecutive diabetic/ACS patients, there was a graded increase in mortality at one year with increasing glucose levels upon hospital admission. In the hospital setting, the ACC/AHA guidelines suggest initiation of aggressive insulin therapy to achieve lower blood glucose during hospitalization.

It has been reported that leptin can have direct benefit to treating diabetes, particularly in type I diabetes and type II diabetes, with or without the presence of obesity, and more particularly in conditions of low serum leptin. It has been reported that leptin replenishment reduced or prevented hyperinsulinemia, insulin resistance and hyperglycemia in various animal models of diabetes type 1 and 2 with or without attendant obesity. For example, high leptin plasma levels generated either by pharmacological administration of leptin or with adenoviral gene therapy reduced hyperglycemia and associated increases of plasma glucagon levels in STZ-induced diabetes, despite persistently low insulin levels.

Lipid regulation diseases. As known in the art, lipodystrophy is characterized by abnormal or degenerative conditions of the body's adipose tissue. Dyslipidemia is a disruption in the normal lipid component in the blood. It is believed that prolonged elevation of insulin levels can lead to dyslipidemia. Hyperlipidemia is the presence of raised or abnormal levels of lipids and/or lipoproteins in the blood. Hypothalamic amenorrhea is a condition in which menstruation stops for several months due to a problem involving the hypothalamus. It has been found that leptin replacement therapy in women with hypothalamic amenorrhea improves reproductive, thyroid, and growth hormone axes and markers of bone formation without causing adverse effects. See e.g., Oral et al., *N Engl J Med.* 2004, 351: 959-962, 987-997. Fatty liver disease, e.g., nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). It is believed that leptin is one of the key regulators for inflammation and progression of fibrosis in various chronic liver diseases including NASH. See e.g., Ikejima et al., *Hepatology Res.* 33:151-154.

Additionally, without wishing to be bound by any theory, it is believed that relative insulin deficiency in type 2 diabetes, glucose toxicity, and increased hepatic free fatty acid burden through elevated delivery from intra-abdominal adipose tissue via the portal vein, are implicated as possible causes in fatty liver disorders. Indeed, it has been hypothesized that eating behavior is the key factor driving the metabolic syndrome of obesity with its many corollaries, including NASH. Accordingly, treatments aimed at decreasing food intake and increasing the number of small meals, as has already been demonstrated in type 2 diabetes, may effectively treat and prevent NASH. Drugs that promote insulin secretion and weight loss, and delay gastric emptying are also effective at improving glucose tolerance and thus may improve fatty liver with its attendant hyperinsulinemia. Thus, use of a chimeric leptin polypeptide can be well suited as a treatment modality for this condition. Accordingly, chimeric polypeptides described herein can be useful in the treatment of fatty liver disorders.

Alzheimer's disease. Alzheimer's disease (AD), as known in the art, is associated with plaques and tangles in the brain which include dysregulation of the A-beta protein. It is believed that brain lipids are intricately involved in A-beta-related pathogenic pathways, and that an important modulator of lipid homeostasis is leptin. Accordingly, leptin can modulate bidirectional A-beta kinesis, reducing its levels extracellularly. Indeed, it has been demonstrated that chronic administration of leptin to AD-transgenic animals reduced the brain A-beta load, underlying its therapeutic potential. See Fewlass et al., 2004, *FASEB J.*, 18:1870-1878. Additionally, type 2 diabetes mellitus and AD share epidemiological and biochemical features in that both are characterized by insoluble protein aggregates with a fibrillar conformation—amylin in type 2 DM pancreatic islets, and Aβ in AD brain. Without wishing to be bound by any theory, it is believed that similar toxic mechanisms may characterize type-2 DM and AD. See Lim et al., *FEBS Lett.*, 582:2188-2194.

Metabolic syndrome X. Metabolic Syndrome X is characterized by insulin resistance, dyslipidemia, hypertension, and visceral distribution of adipose tissue, and plays a pivotal role in the pathophysiology of type 2 diabetes. It has also been found to be strongly correlated with NASH, fibrosis, and cirrhosis of the liver. Accordingly, chimeric polypeptides described herein can be useful in the treatment of metabolic syndrome X.

Huntington's Disease. Huntington's Disease is an autosomal dominant, neurogenerative disease. Features of the disease include motor disturbances, dementia, psychiatric problems, and unintended weight loss. Chimeric polypeptides described herein can be useful in the treatment of Huntington's Disease.

Accordingly, in one aspect, there is provided a method for treating a disease or disorder in a subject. The subject is in need of treatment for the disease or disorder. The disease or disorder can be lipodystrophy, dyslipidemia, hyperlipidemia, overweight, obesity, hypothalamic amenorrhea, Alzheimer's disease, leptin deficiency, fatty liver disease or diabetes (including type I and type II). Additional diseases and disorders which can be treated by the compounds and methods described herein include nonalcoholic steatohepatitis (NASH), nonalcoholic fatty liver disease (NAFLD), metabolic syndrome X and Huntington's Disease. The method of treatment includes administration to the subject of a chimeric polypeptide as described herein in an amount effective to treatment the disease or disorder.

V. Assays

Methods for production and assay of chimeric polypeptides described herein are generally available to the skilled artisan. Further, specific methods are described herein as well as in the patent publications and other references cited herein, which are incorporated by reference for this additional purpose.

Food intake. Without wishing to be bound by any theory, it is believed that food intake is useful in the assessment of the utility of a compound as described herein. For example, it is known that a number of metabolic pathologies are related to food intake (e.g., diabetes, obesity). Accordingly, an initial screening can be conducted to determine the extent to which food intake is modulated by administration of compounds described herein, and a positive initial screening can be useful in subsequent development of a compound.

In vitro assays. Without wishing to be bound by any theory or mechanism of action, it is believed that correlations exist between the results of in vitro (e.g., receptor) assays, and the utility of agents for the treatment of metabolic diseases and disorders. Accordingly, in vitro assays (e.g., cell based assays) are useful as a screening strategy for potential metabolic agents, such as described herein. A variety of in vitro assays are known in the art, including those described as follows.

Leptin binding assay. Leptin binding can be measured by the potency of a test compound in displacing $^{125}$I-recombinant-Leptin (murine) from the surface membrane expressing chimeric Leptin (Hu)—EPO (Mu) receptor presented by the 32D OBECA cell line (*J Biol Chem* 1998; 273(29): 18365-18373). Purified cell membranes can be prepared by homogenization from harvested confluent cell cultures of 32D OBECA cells. Membranes can be incubated with $^{125}$I-rec-Murine-Leptin and increasing concentrations of test compound for 3 hours at ambient temperature in 96-well polystyrene plates. Bound and unbound ligand fractions can then be separated by rapid filtration onto 96-well GF/B plates pre-blocked for at least 60' in 0.5% PEI (polyethyleneimine). Glass fiber plates can then be dried, scintillant added, and CPM determined by reading on a multiwell scintillation counter capable of reading radiolabeled iodine.

Leptin functional assay. Increased levels of phosphorylated STAT5 (Signal Transducer and Activator of Transcription 5) can be measured following treatment of 32D-Keptin cells ectopically expressing chimeric Hu-Leptin/Mu-EPO receptor with a test compound. The 32D-Keptin cells (identical to 32D-OBECA cells but maintained in culture with leptin) can be leptin weaned overnight and then treated with test compounds in 96-well plates for 30 minutes at 37° C. followed by cell extraction. The pSTAT5 levels in the cell lysates can be determined using the Perkin Elmer AlphaScreen® SureFire® pSTAT5 assay kit in a 384-well format (PROXIPLATE™ 384 Plus). The efficacy of test compounds can be determined relative to the maximal signal in cell lysates from cells treated with Human leptin.

VI. Pharmaceutical Compositions

In one aspect, there are provided pharmaceutical compositions comprising compounds described herein in combination with a pharmaceutically acceptable excipient (e.g., carrier). The term "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

A. Methods

The chimeric polypeptides described herein can be administered alone or can be co-administered to a subject. Co-administration is meant to include simultaneous or sequential administration of the compounds individually or in combination (more than one compound). For example, it has been found that obesity can be beneficially treated with a combination therapy including a leptin (e.g., metreleptin) and certain other anti-obesity compounds. See e.g., U.S. Published Appl. No. 2008/0207512. Accordingly, a chimeric polypeptide described herein could be useful for treatment of obesity.

In some embodiments, the formulations and methods described herein further provide that the chimeric polypeptide is co-administered with one or more anti-diabetic agents, such as anti-hyperglycemia agents, e.g. insulin, amylins, pramlintide, metformin.

In some embodiments, the formulations and methods described herein further provide that the chimeric polypeptide is co-administered with one or more cholesterol and/or triglyceride lowering agents. Exemplary agents include HMG CoA reductase inhibitors (e.g., atorvastatin, fluvastatin, lovastatin, pravastatin, rosuvastatin, simvastatin); bile ace sequestrants (e.g., colesevelam, cholestyramine, colestipol); fibrates (e.g., fenofibrate, clofibrate, gemfibrozil); ezetimibe, nicotinic acid, probucol, a lovastatin/niacin combination; an atorvastatin/amlodipine combination; and a simvastatin/ezetimibe combination.

Alternatively, the individual chimeric polypeptides can be co-administered with other anti-obesity agents, such as exenatide or liraglutide.

The present disclosure provides the composition for use as a medicament, i.e. for use in therapy, since the leptin compound is a therapeutically active compound. Compositions comprising a chimeric polypeptide, either liquid or dry form, and optionally at least one pharmaceutically acceptable carrier and/or excipient are also specifically contemplated and are exemplified herein.

Co-administration can be achieved by separately administering the chimeric polypeptide with the second agent, or by administering a single pharmaceutical formulation comprising the chimeric polypeptide and the second agent. Appropriate dosage regimens for the second agents are generally known in the art.

The preparations can also be co-administered, when desired, with other active substances (e.g. to reduce metabolic degradation) as known in the art or other therapeutically active agents.

Amylins. Amylin is a peptide hormone synthesized by pancreatic β-cells that is co-secreted with insulin in response to nutrient intake. The sequence of amylin is highly preserved across mammalian species, with structural similarities to calcitonin gene-related peptide (CGRP), the calcitonins, the intermedins, and adrenomedullin, as known in the art. The glucoregulatory actions of amylin complement those of insulin by regulating the rate of glucose appearance in the circulation via suppression of nutrient-stimulated glucagon secretion and slowing gastric emptying. In insulin-treated patients with diabetes, pramlintide, a synthetic and equipotent analogue of human amylin, reduces postprandial glucose excursions by suppressing inappropriately elevated postprandial glucagon secretion and slowing gastric emptying. The sequences of rat amylin, human amylin and pramlintide follow:

```
rat amylin:
                                (SEQ ID NO: 86)
KCNTATCATQRLANFLVRSSNNLGPVLPPTNVGSNTY;

human amylin:
                                (SEQ ID NO: 87)
KCNTATCATQRLANFLVHSSNNFGAILSSTNVGSNTY;

Pramlintide:
                                (SEQ ID NO: 88)
KCNTATCATQRLANFLVHSSNNFGPILPPTNVGSNTY.
```

Davalintide. Davalintide, also known as "AC-2307" is a potent amylin agonist useful in the treatment of a variety of disease indications. See WO 2006/083254 and WO 2007/114838, each of which is incorporated by reference herein in its entirety and for all purposes. Davalintide is a chimeric peptide, having an N-terminal loop region of amylin or calcitonin and analogs thereof, an alpha-helical region of at least a portion of an alpha-helical region of calcitonin or analogs thereof or an alpha-helical region having a portion of an amylin alpha-helical region and a calcitonin alpha-helical region or analog thereof, and a C-terminal tail region of amylin or calcitonin. The sequences of human calcitonin, salmon calcitonin and davalintide follow:

```
human calcitonin:
                                (SEQ ID NO: 89)
CGNLSTCMLGTYTQDFNKFHTFPQTAIGVGAP;

salmon calcitonin:
                                (SEQ ID NO: 90)
CSNLSTCVLGKLSQELHKLQTYPRTNTGSGTP;

davalintide:
                                (SEQ ID NO: 91)
KCNTATCVLGRLSQELHRLQTYPRTNTGSNTY.
```

Without wishing to be bound by any theory, it is believed that amylins and davalintide, and fragments and analogs thereof, can require C-terminal amidation to elicit a full biological response. It is understood that amylin compounds such as those described herein which include amylins and/or davalintide, and fragment and analogs thereof, can be amidated at the C-terminal.

"Amylin agonist compounds" include native amylin peptides, amylin analog peptides, and other compounds (e.g., small molecules) that have amylin agonist activity. The "amylin agonist compounds" can be derived from natural sources, can be synthetic, or can be derived from recombinant DNA techniques. Amylin agonist compounds have amylin agonist receptor binding activity and may comprise amino acids (e.g., natural, unnatural, or a combination thereof), peptide mimetics, chemical moieties, and the like. The skilled artisan will recognize amylin agonist compounds using amylin receptor binding assays or by measuring amylin agonist activity in soleus muscle assays. In one embodiment, amylin agonist compounds will have an $IC_{50}$ of about 200 nM or less, about 100 nM or less, or about 50 nM or less, in an amylin receptor binding assay, such as that described herein, in U.S. Pat. No. 5,686,411, and US Publication No. 2008/0176804, the disclosures of which are incorporated by reference herein in their entireties and for all purposes. In one embodiment, amylin agonist compounds will have an $EC_{50}$ of about 20 nM or less, about 15 nM or less, about 10 nM or less, or about 5 nM or less in a soleus muscle assay, such as that described herein and in U.S. Pat. No. 5,686,411. In one embodiment, the amylin agonist compound has at least 90% or 100% sequence identity to $^{25,28,29}$Pro-human-amylin. In one embodiment, the amylin agonist compound is a peptide chimera of amylin (e.g., human amylin, rat amylin, and the like) and calcitonin (e.g., human calcitonin, salmon calcitonin, and the like). Suitable and exemplary amylin agonist compounds are also described in US Publication No. 2008/0274952, the disclosure of which is incorporated by reference herein in its entirety and for all purposes.

By "amylin analog" as used herein is meant an amylin agonist that has at least 50% sequence identity, preferably at least 70% sequence identity, to a naturally-occurring form of amylin, either rat or human or from any other species, and is derived from them by modifications including insertions, substitutions, extensions, and/or deletions of the reference amino acid sequence.

The amylin analog sequence can have at least 50%, 55%, 60%, 65%, 70%, 75%, 80%, 90%, or 95% amino acid sequence identity with the reference amylin. In one aspect the analog has 0, 1, 2, 3, 4, 5, 6, 7, 8, 9, 10, 11, 12, 13, 14, 15 or even 16 amino acid substitutions, insertions, extensions, and/or deletions relative to the reference compound. In one embodiment, the amylin analog may comprise conservative or non-conservative amino acid substitutions (including non-natural amino acids and L and D forms). These analogs are preferably peptides, peptide derivatives or peptide mimics. Typical amylin analogs will be peptides, especially of 32-37 amino acids, e.g. 27 to 45, especially 28 to 38, and even 31-36.

Amylin analogs with identity to rat and human amylin include $^{25,28,29}$Pro-h-amylin (pramlintide) (SEQ ID NO: 88); des-$^{1}$Lys-h-amylin (SEQ ID NO: 111); $^{25}$Pro, $^{26}$Val,$^{28,29}$Pro-h-amylin (SEQ ID NO: 112); $^{18}$Arg,$^{25,28}$Pro-h-amylin (SEQ ID NO: 113); des-$^{1}$Lys,$^{18}$Arg,$^{25,28}$Pro-h-amylin (SEQ ID NO: 114); $^{18}$Arg,$^{25,28,29}$Pro-h-amylin (SEQ ID NO: 115); des-$^{1}$Lys,$^{18}$Arg,$^{25,28,29}$Pro-h-amylin (SEQ ID NO: 116); des-$^{1}$,Lys$^{25,28,29}$Pro-h-amylin (SEQ ID NO: 117); $^{25}$Pro,$^{26}$Val,$^{28,29}$Pro-h-amylin (SEQ ID NO: 118); $^{28}$Pro-h-amylin, 2,7-Cyclo-[$^{2}$Asp,$^{7}$Lys]-h-amylin (SEQ ID NO: 119); $^{2-37}$h-amylin (SEQ ID NO: 120); $^{1}$Ala-h-amylin (SEQ ID NO: 121); ²Ala-h-amylin (SEQ ID NO: 122); $^{2,7}$Ala-h-amylin (SEQ ID NO: 123); ¹Ser-h-amylin (SEQ ID NO: 124); ²⁹Pro-h-amylin (SEQ ID NO: 125); $^{25,28}$Pro-h-amylin (SEQ ID NO: 126); des-¹Lys,$^{25,28}$Pro-h-amylin (SEQ ID NO: 127); ²³Leu,²⁵Pro,²⁶Val,$^{28,29}$Pro-h-amylin (SEQ ID NO: 128); ²³Leu²⁵Pro²⁶Val²⁸Pro-h-amylin (SEQ ID NO: 129); des-¹Lys,²³Leu,²⁵Pro,²⁶Val,²⁸Pro-h-amylin (SEQ ID NO: 130); ¹⁸Arg,²³Leu,²⁵Pro,²⁶Val,²⁸Pro-h-amylin (SEQ ID NO: 131); ¹⁸Arg,²³Leu,$^{25,28,29}$Pro-h-amylin (SEQ ID NO: 132); ¹⁸Arg²³Leu,$^{25,28}$Pro-h-amylin (SEQ ID NO: 133); ¹⁷Ile,²³Leu,$^{25,28,29}$Pro-h-amylin (SEQ ID NO: 134); ¹⁷Ile,$^{25,28,29}$Pro-h-amylin (SEQ ID NO: 135); des-¹Lys,¹⁷Ile,²³Leu,$^{25,28,29}$Pro-h-amylin (SEQ ID NO: 136); ¹⁷Ile,¹⁸Arg,²³Leu-h-amylin (SEQ ID NO: 137); ¹⁷Ile,¹⁸Arg,²³Leu,²⁶Val,²⁹Pro-h-amylin (SEQ ID NO: 138); ¹⁷Ile,¹⁸Arg,²³Leu,²⁵Pro,²⁶Val,$^{28,29}$Pro-h-amylin (SEQ ID NO: 139); ¹³Thr,²¹His,²³Leu,²⁶Ala,²⁸Leu,²⁹Pro,³¹Asp-h-amylin (SEQ ID NO: 140); ¹³Thr,²¹His,²³Leu,²⁶Ala,²⁹Pro,³¹Asp-h-amylin (SEQ ID NO: 141); des-¹Lys,¹³Thr,²¹His,²³Leu,²⁶Ala,²⁸Pro,³¹Asp-h-amylin (SEQ ID NO: 142); ¹³Thr,¹⁸Arg,²¹His,²³Leu,²⁶Ala,²⁹Pro,³¹Asp-h-amylin (SEQ ID NO: 143); ¹³Thr,¹⁸Arg,²¹His,²³Leu,$^{28,29}$Pro,³¹Asp-h-amylin (SEQ ID NO: 144); and ¹³Thr,¹⁸Arg,²¹His,²³Leu,²⁵Pro,²⁶Ala,$^{28,29}$Pro,³¹Asp-h-amylin (SEQ ID NO: 145).

Amylin analogs include amino acid sequences of residues 1-37 of Formula (I) following, wherein up to 25% of the amino acids set forth in Formula (I) may be deleted or substituted with a different amino acid:

(I)

(SEQ ID NO: 92)
X'-Xaa¹-Cys²-Asn³-Thr⁴-Ala⁵-Thr⁶-Cys⁷-Ala⁸-Thr⁹-

Gln¹⁰-Arg¹¹-Leu¹²-Ala¹³-Asn¹⁴-Phe¹⁵-Leu¹⁶-Val¹⁷-

His¹⁸-Ser¹⁹-Ser²⁰-Xaa²¹-Asn²²-Phe²³-Xaa²⁴-Xaa²⁵-

Xaa²⁶-Xaa²⁷-Xaa²⁸-Xaa²⁹-Thr³⁰-Xaa³¹-Val³²-Gly³³-

Ser³⁴-Asn³⁵-Thr³⁶-Tyr³⁷-X.

In Formula (I), X' is hydrogen, an N-terminal capping group, or a linker to a duration enhancing moiety. Xaa¹ is Lys or a bond, Xaa²¹ is Lys, Cys, or Asn, Xaa²⁴ is Lys, Cys, or Gly, Xaa²⁵ is Lys, Cys, or Pro, Xaa²⁶ is Lys, Cys, or Ile, Xaa²⁷ is Lys, Cys, or Leu, Xaa²⁸ is Lys, Cys, or Pro, Xaa²⁹ is Lys, Cys, or Pro and Xaa³¹ is Lys, Cys, or Asn. Further regarding Formula (I), the variable X represents a C-terminal functionality (e.g., a C-terminal cap). X is substituted or unsubstituted amino, substituted or unsubstituted alkylamino, substituted or unsubstituted dialkylamino, substituted or unsubstituted cycloalkylamino, substituted or unsubstituted arylamino, substituted or unsubstituted aralkylamino, substituted or unsubstituted alkyloxy, substituted or unsubstituted aryloxy, substituted or unsubstituted aralkyloxy, or hydroxyl. If the C-terminal of the polypeptide component with the sequence of residues 1-37 of Formula (I) is capped with a functionality X, then X is preferably amine thereby forming a C-terminal amide. In some embodiments, up to 5%, 10%, 15%, 20%, 25%, 30%, 35%, 40%, 45% or even 50% of the amino acids of residues 1-37 of Formula (I) are deleted or substituted in a polypeptide component according to Formula (I). In some embodiments, the amylin analog component has 0, 1, 2, 3, 4, 5, 6, 7, 8, 9, 10, 11, 12, 13, 14, 15 or even 16 amino acid substitutions relative to the amino acid sequence set forth in Formula (I). In some embodiments, the amylin analog has a sequence which has a defined sequence identity with respect to the residues 1-37 of the amino acid sequence according to Formula (I). In some embodiments, the sequence identity between an amylin analog described herein and residues 1-37 of Formula (I) is 50%, 55%, 60%, 65%, 70%, 75%, 80%, 85%, 90%, 95% or even higher. In some embodiments, up to 50%, 45%, 40%, 35%, 30%, 25%, 20%, 15%, 10%, 5% or even less of the amino acids set forth in residues 1-37 of Formula (I) may be deleted or substituted with a different amino acid. In some embodiments, the sequence identity is within the range 75%-100%. In some embodiments, the sequence identity is within the range 75%-90%. In some embodiments, the sequence identity is within the range 80%-90%. In some embodiments, the sequence identity is at least 75%. In some embodiments, the amylin analog has the sequence of residues 1-37 of Formula (I).

In some embodiments, amylin analogs including those of Formula (I), form the basis of a polypeptide component to which one or more duration enhancing moieties are linked, optionally through a linker, to form an amylin polypeptide conjugate. Thus, the polypeptide component serves as a template ("polypeptide template") to which is attached, preferably by covalent attachment, one or more duration enhancing moieties. Linkage of the duration enhancing moiety to the polypeptide component can be through a linker as described herein. Alternatively, linkage of the duration enhancing moiety to the polypeptide component can be via a direct covalent bond. The duration enhancing moiety can be a water soluble polymer as described herein. In some embodiments, a plurality of duration enhancing moieties are attached to the polypeptide component, in which case each linker to each duration enhancing moiety is independently selected from the linkers described herein.

Amylin analogs useful as polypeptide components described herein include, but are not limited to, the compounds set forth in residues 1-37 of Formula (I) provided in Table 1 below. Unless indicated to the contrary, all peptides described herein, including peptides having an expressly provided sequence, are contemplated in both free carboxylate and amidated forms.

TABLE 1

Component polypeptides useful in the compounds described herein.

| Cmpd | Description (sequence) |
|---|---|
| 1 | KCNTATCATQRLANFLVRSSNNLGPVLPPTNVGSNTY-NH$_2$ (SEQ ID NO: 110) |
| 2 | CNTATCATQRLANFLVRSSNNLGPVLPPTNVGSNTY-NH$_2$ (SEQ ID NO: 93) ([desLys¹]-Cmpd 1) |
| 3 | KCNTATCATQRLANFLVRSSKNLGPVLPPTNVGSNTY-NH$_2$ (SEQ ID NO: 94) |
| 4 | CNTATCATQRLANFLVRSSKNLGPVLPPTNVGSNTY-NH$_2$ (SEQ ID NO: 95) ([desLys¹]-Cmpd 3) |
| 5 | KCNTATCATQRLANFLVRSSNNLGPKLPPTNVGSNTY-NH$_2$ (SEQ ID NO: 96) |
| 6 | CNTATCATQRLANFLVRSSNNLGPKLPPTNVGSNTY-NH$_2$ (SEQ ID NO: 97) ([desLys¹]-Cmpd 5) |
| 7 | KCNTATCATQRLANFLVRSSNNLGPVLPPTKVGSNTY-NH$_2$ (SEQ ID NO: 98) |

TABLE 1-continued

Component polypeptides useful in the compounds described herein.

| Cmpd | Description (sequence) |
|---|---|
| 8 | CNTATCATQRLANFLVRSSNNLGPVLPPTKVGSNTY-NH$_2$ (SEQ ID NO: 99) ([desLys$^1$]-Cmpd 7) |
| 9 | KCNTATCATQRLANFLVHSSNNFGPILPPTNVGSNTY-NH$_2$ (SEQ ID NO: 100) |
| 10 | CNTATCATQRLANFLVHSSNNFGPILPPTNVGSNTY-NH$_2$ (SEQ ID NO: 101) ([desLys$^1$]-Cmpd 9) |
| 11 | CNTATCATQRLANFLVHSSKNFGPILPPTNVGSNTY-NH$_2$ (SEQ ID NO: 102) |
| 12 | CNTATCATQRLANFLVHSSNNFGPKLPPTNVGSNTY-NH$_2$ (SEQ ID NO: 103) |
| 13 | CNTATCATQRLANFLVHSSNNFGPILPPTKVGSNTY-NH$_2$ (SEQ ID NO: 104) |
| 14 | CNTATCATQRLANFLVHSSNNFKPILPPTNVGSNTY-NH$_2$ (SEQ ID NO: 105) |
| 15 | CNTATCATQRLANFLVHSSNNFGKILPPTNVGSNTY-NH$_2$ (SEQ ID NO: 106) |
| 16 | CNTATCATQRLANFLVHSSNNFGPIKPPTNVGSNTY-NH$_2$ (SEQ ID NO: 107) |
| 17 | CNTATCATQRLANFLVHSSNNFGPILKPTNVGSNTY-NH$_2$ (SEQ ID NO: 108) |
| 18 | CNTATCATQRLANFLVHSSNNFGPILPKTNVGSNTY-NH$_2$ (SEQ ID NO: 109) |

The terms "linker" and the like, in the context of attachment of duration enhancing moieties to a polypeptide component in an amylin polypeptide conjugate described herein, means a divalent species (-L-) covalently bonded in turn to a polypeptide component having a valency available for bonding and to a duration enhancing moiety having a valency available for bonding. The available bonding site on the polypeptide component is conveniently a side chain residue (e.g., lysine, cysteine, aspartic acid, and homologs thereof). In some embodiments, the available bonding site on the polypeptide component is the side chain of a lysine or a cysteine residue. In some embodiments, the available bonding site on the polypeptide component is the N-terminal amine. In some embodiments, the available bonding site on the polypeptide component is the C-terminal carboxyl. In some embodiments, the available bonding site on the polypeptide component is a backbone atom thereof. As used herein, the term "linking amino acid residue" means an amino acid within residues 1-37 of Formula (I) to which a duration enhancing moiety is attached, optionally through a linker.

In some embodiments, compounds are provided having a linker covalently linking a polypeptide component with a duration enhancing moiety. The linker is optional; i.e., any linker may simply be a bond. In some embodiments, the linker is attached at a side chain of the polypeptide component. In some embodiments, the linker is attached to a backbone atom of the polypeptide component.

In another aspect, there is provided an amylin polypeptide conjugate, which is a derivative of pramlintide with SEQ ID NO:88 or an analog thereof, wherein the amino acid residue in position 1 is absent (i.e., des-Lys$^1$) and an amino acid residue in position 2 to 37 has been substituted with a lysine residue or cysteine residue and wherein said lysine residue or cysteine residue is linked to a polyethylene glycol polymer, optionally via a linker, wherein the amino acid numbering conforms with the amino acid number in SEQ ID NO:88.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in any one of position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 31, 32, 33, 34, 35, 36, or 37 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in any one of position 21, 24-29, or 31 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in position 21 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in position 24 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in position 25 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in position 26 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys$^1$) and wherein an amino acid residue in position 27 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys¹) and wherein an amino acid residue in position 28 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys¹) and wherein an amino acid residue in position 29 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:88 or an analog thereof, wherein the amino acid residue in position 1 is absent (i.e., des-Lys¹) and wherein an amino acid residue in position 31 is substituted with a lysine residue and wherein said lysine residue is linked to a polyethylene glycol polymer, optionally via a linker.

In some embodiments, the duration enhancing moiety is a water-soluble polymer. A "water soluble polymer" means a polymer which is sufficiently soluble in water under physiologic conditions of e.g., temperature, ionic concentration and the like, as known in the art, to be useful for the methods described herein. A water soluble polymer can increase the solubility of a peptide or other biomolecule to which such water soluble polymer is attached. Indeed, such attachment has been proposed as a means for improving the circulating life, water solubility and/or antigenicity of administered proteins, in vivo. See e.g., U.S. Pat. No. 4,179,337; U.S. Published Appl. No. 2008/0032408. Many different water-soluble polymers and attachment chemistries have been used towards this goal, such as polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and the like.

In some embodiments, the linked duration enhancing moiety includes a polyethylene glycol. Polyethylene glycol ("PEG") has been used in efforts to obtain therapeutically usable polypeptides. See e.g., Zalipsky, S., 1995, *Bioconjugate Chemistry*, 6:150-165; Mehvar, R., 2000, *J. Pharm. Pharmaceut. Sci.*, 3:125-136. As appreciated by one of skill in the art, the PEG backbone [(CH$_2$CH$_2$—O—)$_n$, n: number of repeating monomers] is flexible and amphiphilic. Without wishing to be bound by any theory or mechanism of action, the long, chain-like PEG molecule or moiety is believed to be heavily hydrated and in rapid motion when in an aqueous medium. This rapid motion is believed to cause the PEG to sweep out a large volume and prevents the approach and interference of other molecules. As a result, when attached to another chemical entity (such as a peptide), PEG polymer chains can protect such chemical entity from immune response and other clearance mechanisms. As a result, pegylation can lead to improved drug efficacy and safety by optimizing pharmacokinetics, increasing bioavailability, and decreasing immunogenicity and dosing frequency. "Pegylation" refers in the customary sense to conjugation of a PEG moiety with another compound. For example, attachment of PEG has been shown to protect proteins against proteolysis. See e.g., Blomhoff, H. K. et al., 1983, *Biochim Biophys Acta*, 757:202-208. Unless expressly indicated to the contrary, the terms "PEG," "polyethylene glycol polymer" and the like refer to polyethylene glycol polymer and derivatives thereof, including methoxy-PEG (mPEG).

A variety of means have been used to attach polymer moieties such as PEG and related polymers to reactive groups found on the protein. See e.g., U.S. Pat. No. 4,179,337; U.S. Pat. No. 4,002,531; Abuchowski et al., 1981, in "Enzymes as Drugs," J. S. Holcerberg and J. Roberts, (Eds.), pp. 367-383; Zalipsky, S., 1995, *Bioconjugate Chemistry*, 6:150-165. The use of PEG and other polymers to modify proteins has been discussed. See e.g., Cheng, T.-L. et al., 1999m, *Bioconjugate Chem.*, 10:520-528; Belcheva, N. et al., 1999, *Bioconjugate Chem.*, 10:932-937; Bettinger, T. et al., 1998, *Bioconjugate Chem.*, 9:842-846; Huang, S.-Y. et al., 1998, *Bioconjugate Chem.*, 9:612-617; Xu, B. et al. 1998, *Langmuir*, 13:2447-2456; Schwarz, J. B. et al., 1999, *J. Amer. Chem. Soc.*, 121:2662-2673; Reuter, J. D. et al., 1999, *Bioconjugate Chem.*, 10:271-278; Chan, T.-H. et al., 1997, *J. Org. Chem.*, 62:3500-3504. Typical attachment sites in proteins include primary amino groups, such as those on lysine residues or at the N-terminus, thiol groups, such as those on cysteine side-chains, and carboxyl groups, such as those on glutamate or aspartate residues or at the C-terminus. Common sites of attachment are to the sugar residues of glycoproteins, cysteines or to the N-terminus and lysines of the target polypeptide. The terms "pegylated" and the like refer to covalent attachment of polyethylene glycol to a polypeptide or other biomolecule, optionally through a linker as described herein and/or as known in the art.

In some embodiments, a PEG moiety in an amylin polypeptide conjugate described herein has a nominal molecular weight within a specified range. As customary in the art, the size of a PEG moiety is indicated by reference to the nominal molecular weight, typically provided in kilodaltons (kD). The molecular weight is calculated in a variety of ways known in the art, including number, weight, viscosity and "Z" average molecular weight. It is understood that polymers, such as PEG and the like, exist as a distribution of molecule weights about a nominal average value.

Exemplary of the terminology for molecular weight for PEGs, the term "mPEG40KD" refers to a methoxy polyethylene glycol polymer having a nominal molecular weight of 40 kilodaltons. Reference to PEGs of other molecular weights follows this convention. In some embodiments, the PEG moiety has a nominal molecular weight in the range 10-100 KD, 20-80 KD, 20-60 KD, or 20-40 KD. In some embodiments, the PEG moiety has a nominal molecular weight of 10, 15, 20, 25, 30, 35, 40, 45, 50, 55, 60, 65, 70, 75, 80, 85, 90, 95 or even 100 KD. Preferably, the PEG moiety has a molecular weight of 20, 25, 30, 40, 60 or 80 KD.

PEG molecules useful for derivatization of polypeptides are typically classified into linear, branched and Warwick (i.e., PolyPEG®) classes of PEGs, as known in the art. Unless expressly indicated to the contrary, the PEG moieties described herein are linear PEGs. Furthermore, the terms "two arm branched," "Y-shaped" and the like refer to branched PEG moieties, as known in the art. The term "Warwick" in the context of PEGs, also known as "comb" or "comb-type" PEGs, refers to a variety of multi-arm PEGs attached to a backbone, typically poly(methacrylate), as known in the art. Regarding nomenclature including conventions employed in the table provided herein, absent indication to the contrary a PEG moiety is attached to the backbone of the peptide. For example, Cmpd 19 is the result of the conjugation of mPEG40KD to the N-terminal nitrogen of Cmpd 1. Similarly, Cmpd 20 is the result of conjugation of mPEG40KD to the N-terminal nitrogen of Cmpd 2. Standard single letter abbreviations for amino acids can be used, as can standard three-letter abbreviations. For example, Cmpd 24 is an analog of Cmpd 10 wherein the residue at position 26 of Cmpd 9 is substituted for lysine, and the pendant amine functionality of lysine 26 (i.e., $K^{26}$) is conjugated with a PEG40KD moiety. Exemplary compounds are provided in Table 2 below.

TABLE 2

Pegylated compounds

| Cmpd | Description |
| --- | --- |
| 19 | mPEG40KD-Cmpd 1 (SEQ ID NO: 146) |
| 20 | mPEG40KD-Cmpd 2 (SEQ ID NO: 147) |
| 21 | [$K^{21}$(mPEG40KD)]-Cmpd 3 (SEQ ID NO: 148) |
| 22 | [$K^{21}$(mPEG40KD)]-Cmpd 4 (SEQ ID NO: 149) |
| 23 | [$K^{26}$(mPEG40KD)]-Cmpd 5 (SEQ ID NO: 150) |
| 24 | [$K^{26}$(mPEG40KD)]-Cmpd 6 (SEQ ID NO: 151) |
| 25 | [$K^{31}$(mPEG40KD)]-Cmpd 7 (SEQ ID NO: 152) |
| 26 | [$K^{31}$(mPEG40KD)]-Cmpd 8 (SEQ ID NO: 153) |
| 27 | [$K^{26}$(Y-shaped-mPEG40KD)]-Cmpd 5 (SEQ ID NO: 154) |
| 28 | [$K^{21}$(mPEG40KD)]-Cmpd 11 (SEQ ID NO: 155) |
| 29 | [$K^{26}$(mPEG40KD)]-Cmpd 12 (SEQ ID NO: 156) |
| 30 | [$K^{31}$(mPEG40KD)]-Cmpd 13 (SEQ ID NO: 157) |
| 31 | [$K^{26}$(Y-shaped-mPEG40KD)]-Cmpd 12 (SEQ ID NO: 158) |
| 32 | [$K^{24}$(mPEG40KD)]-Cmpd 14 (SEQ ID NO: 159) |
| 33 | [$K^{25}$(mPEG40KD)]-Cmpd 15 (SEQ ID NO: 160) |
| 34 | [$K^{27}$(mPEG40KD)]-Cmpd 16 (SEQ ID NO: 161) |
| 35 | [$K^{28}$(mPEG40KD)]-Cmpd 17 (SEQ ID NO: 162) |
| 36 | [$K^{29}$(mPEG40KD)]-Cmpd 18 (SEQ ID NO: 163) |

B. Formulations

The pharmaceutical compounds of the invention may be formulated with pharmaceutically acceptable carriers or diluents as well as any other known adjuvants and excipients in accordance with conventional techniques such as those disclosed in *Remington's Pharmaceutical Sciences* by E. W. Martin. See also Wang et al. (1988) *J. of Parenteral Sci.* and Tech., Technical Report No. 10, Supp. 42:2 S.

In general, the chimeric polypeptides may be formulated into a stable, safe pharmaceutical composition for administration to a patient. Pharmaceutical formulations contemplated for use in the methods of the invention may comprise approximately 0.01 to 1.0% (w/v), in certain cases 0.05 to 1.0%, of the chimeric polypeptide, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In particular embodiments, a pharmaceutical formulation of the present chimeric polypeptides may contain a range of concentrations of the compound(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the compound. An excipient may be included in the presently described formulations at various concentrations. For example, an excipient may be included in the concentration range from about 0.02% to about 20% w/w, preferably between about 0.02% and 0.5% w/w, about 0.02% to about 10% w/v, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the formulations of chimeric polypeptides, for example, water or an aqueous/organic solvent mixture or suspension.

The stability of a chimeric polypeptide formulation for use as described herein is enhanced by maintaining the pH of the formulation in a range determined by methods known in the art. In certain embodiments, the pH of the formulation is maintained in the range of about 3.5 to 5.0, or about 3.5 to 6.5, in some embodiments from about 3.7 to 4.3, or about 3.8 to 4.2. In some embodiments, pH may be about 4.0, about 5.0, about 6.0, about 7.0, about 8.0, about 9.0, or even higher. In some embodiments, pH may be in the physiological range, pH 6-8, preferably pH 7-7.6.

In certain embodiments, the buffer with the chimeric polypeptide is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). In some embodiments, the buffer is acetate (preferably at a final formulation concentration of from about 5 to about 30 mM).

A stabilizer may be included in the formulations but is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic applications (e.g. treating obesity).

In certain embodiments, if a stabilizer is included, the compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, 8000 and even higher). Mannitol is the preferred polyhydric alcohol in some embodiments. Another useful feature of the lyophilized formulations of the present invention is the maintenance of the tonicity of the lyophilized formulations described herein with the same formulation component that serves to maintain their stability. In some embodiments, mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in *Remington's Pharmaceutical Sciences* (*Id.*)

Chimeric polypeptides may not have a tendency to adsorb onto the glass in a glass container when in a liquid form, therefore, a surfactant may not be required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the chimeric polypeptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio]1-propanesulfonate), Brij® (e.g., Brij® 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type 1-33) or its equivalent (Wheaton Glass Co.). Other vendors of similar borosilicate glass vials and cartridges acceptable for manufacture include Kimbel Glass Co., West Co., Bunder Glas GMBH and Form a Vitrum. The biological and chemical properties of the compound may be stabilized by formulation and lyophilization in a Wheaton Type 1-33 borosilicate serum vial to a final concentration of 0.1 mg/ml and 10 mg/ml of the compound in the presence of 5% mannitol, and 0.02% Tween 80.

For formulations to be delivered by injection, in order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. For formulations comprising peptidic anti-obesity agents, these stoppers are compatible with the peptide as well as the other components of the formulation. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in PHARMACEUTICAL DOSAGE FORMS: PARENTERAL MEDICATIONS, Vol. 1, 2nd ed., Avis et al. Ed., Mercel Dekker, New York, N.Y. 1992, which is incorporated by reference in its entirety herein and for all purposes.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 um and 0.22 um (1 or 2) which may be connected in series. After filtration, the solution is filled into appropriate vials or containers.

In certain embodiments, the chimeric polypeptides described herein are administered peripherally to the subjects. In some embodiments, the liquid pharmaceutical formulations of the present invention are intended for parenteral administration. Suitable routes of administration include intramuscular, intravenous, subcutaneous, intradermal, intraarticular, intrathecal and the like. In some embodiments, the subcutaneous route of administration is preferred. In certain embodiments, mucosal delivery is also preferred. These routes include, but are not limited to, oral, nasal, sublingual, pulmonary and buccal routes which may include administration of the peptide in liquid, semi-solid or solid form. For formulations comprising chimeric polypeptides, administration via these routes can require substantially more compound to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842, each of which is incorporated herein by reference in its entirety and for all purposes.

The compounds may be provided in dosage unit form containing an amount of the chimeric polypeptide that will be effective in one or multiple doses.

As will be recognized by those in the field, an effective amount of the chimeric polypeptide will vary with many factors including the age and weight of the subject, the subject's physical condition, the condition to be treated, and other factors known in the art. An effective amount of the chimeric polypeptides will also vary with the particular combination administered.

As described herein, administration of the chimeric polypeptides in combination may allow for a reduced amount of any of the administered chimeric polypeptides to be an effective amount.

C. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat diabetes, such compositions will contain an amount of active ingredient effective to achieve the desired result (e.g. decreasing fasting blood glucose in a subject). When administered in methods to treat obesity, such compositions will contain an amount of active ingredient effective to achieve the desired result (e.g. decrease the body mass).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to compounds described herein); presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring one or more physiological parameters, including but not limited to blood sugar and body mass, and adjusting the dosage upwards or downwards, as described above and known in the art.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

However, typical doses may contain from a lower limit of about 0.1 mg to an upper limit of about 200 mg of the pharmaceutical compound per day. Also contemplated are other dose ranges such as 1 mg to 100 mg of the compound per dose, and 3 mg to 70 mg per dose. The doses per day may be delivered in discrete unit doses, or provided continuously in a 24 hour period or any portion of that the 24 hours.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

D. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

VII. Examples

Example 1: Chimeric Polypeptide Recovery

Protein sequences were designed and back translated using commercial software to DNA sequence for cloning into an E. coli expression vector. Sequences were either obtained as oligonucleotides and stitched together using standard PCR amplification techniques, or they were digested from existing expression constructs using standard restriction enzymes and then ligated back together. Sequences expressing the protein of interest were placed in pET45 with a T7 promoter for inducible expression. After constructs were verified by sequencing, the vector DNA was purified and transformed into an expression host, typically BL21(DE3). A single colony was selected to grow a starter culture in 4 ml LB media for ~6 hrs. Glycerol stocks were prepared by adding 100 ul 80% glycerol to 900 ul stock and store at −80 C. Optionally, 500 ul uninduced sample was retained for gel analysis. A 60 ml culture (magic media) was inoculated using 60 ul starter culture in a 125 ml Thompson flask and incubated @ 30 C overnight. Remove 250 ul sample for analysis. Spin down and freeze cell pellet for later processing.

Bacterial cells were harvested and subsequently lysed to isolate inclusion bodies. Since the protein was present in the inclusion bodies, these were solubilized and the protein refolded at 4 C. Proteins were then separated using size exclusion chromatography until only a single band remained and endotoxin levels were acceptable for in vivo testing. Analytical HPLC, RP-LC-MS and SDS-PAGE gel were run as quality control measures on the final protein. Protein was distributed to predetermined aliquots and stored at −80 C.

Example 2: Biological and Pharmaceutical Properties

As set forth in Table 3 following, chimeric polypeptides described herein have comparable, and some even superior, properties compared with A100 (Compound 37, SEQ ID NO:24). These properties include biological properties such as leptin binding activity, leptin functional activity, and food intake in mice, and pharmaceutical properties such as solubility in neutral pH.

Exemplary assays for leptin binding activity and leptin functional activity were previously described.

Food intake activity in mice was tested with the following assay: C57BL6 female mice and their food were weighed daily 3 hours prior to lights out. Immediately after weighing, on days 0, 1, 2 and 3 mice were injected SC with leptin compound or mutant in 1×PBS. Points represent mean±sd of n=9 cages (3 mice/cage). The results reported under "Mouse Food Intake" in Table 3 correspond to the vehicle corrected, change in % body weight measured after Day 4.

Solubility was measured with the following assay: proteins were concentrated at 4 C, spun to remove precipitates, then allowed to equilibrate at room temperature overnight. They were filtered to remove precipitates and then the concentration was determined by measuring absorbance at OD280 and using the theoretical molar extinction coefficient.

TABLE 3

Biological and pharmaceutical properties of chimeric polypeptides

| Compound | SEQ ID NO. | IC50 (Obeca cell binding) nM | EC50 (Obeca Stat5 functional assay) nM | Mouse Food Intake | Solubility in neutral pH PBS mg/ml* |
|---|---|---|---|---|---|
| 37 | 24 | 0.2 nM-0.8 nM | 0.02 | 4.053 | 5 |
| 38 | 28 | 1.996 | 0.019 | 6.7 | 35 |
| 39 | 53 | ND | 0.095 | 3.1 | ND |
| 40 | 69 | 2.412 | 0.588 | 0 | 17 |
| 41 | 32 | 0.555 | 0.028 | 10.8 | 21 |
| 42 | 61 | 2.017 | 0.043 | 8.4 | 17 |
| 43 | 55 | 3.082 | 0.054 | 6.5 | 17 |
| 44 | 57 | 3.542 | 0.032 | 6.4 | 20 |
| 45 | 63 | 0.527 | 0.029 | 10.3 | 18 |
| 46 | 59 | 0.479 | 0.042 | ~0-2% | 20 |
| 47 | 71 | 0.788 | 0.0625 | ~4% | 15 |
| 48 | 33 | 0.036 | 0.039 | 4.9 | 14 |
| 49 | 81 | 0.105 | 0.034 | 4 | 13 |
| 50 | 67 | 0.214 | 0.022 | 8.3 | 5 |
| 51 | 65 | 0.119 | 0.038 | 3.8 | 25 |
| 52 | 73 | ND | 0.044 | ND | 19 |

ND = not determined

*These numbers do not necessarily represent the maximum solubility of each compound.

Example 3: Stability of Chimeric Peptides

As set forth in Table 4 following, chimeric polypeptides described herein have comparable, and some even superior, physical stability compared with A100 (Compound 37, SEQ ID NO:24). The compounds were formulated in the following buffer: 10 mM glutamic acid, 2% glycine, 1% sucrose, 0.01% Tween 20, pH 4.25 and stored at 37° C. Samples were pulled at T=0, 2, 5, 7, and 14 days and tested by visual analysis, reverse phase high performance liquid chromatography (HPLC), UV spectrometry, and dynamic light scattering (DLS). As shown in Table 4, the chimeric polypeptides have comparable or superior purity and potency, compared with Compound 37.

TABLE 4

Stability of Chimeric Polypeptides

| Cmpd | | Potency Remaining* | Purity Loss** | Corrected Potency*** | Visual | Size Change (DLS) |
|---|---|---|---|---|---|---|
| 38 | 1 mg/ml | 96.3% | 1.8% | 94.6% | Clear | 1.0 |
| 41 | 1 mg/ml | 92.2% | 1.9% | 90.4% | Clear | 2.0 |

TABLE 4-continued

Stability of Chimeric Polypeptides

| Cmpd | | Potency Remaining* | Purity Loss** | Corrected Potency*** | Visual | Size Change (DLS) |
|---|---|---|---|---|---|---|
| 48 | 1 mg/ml | 88.8% | 2.7% | 86.1% | Clear | 1.7 |
| 42 | 1 mg/ml | 96.3% | 14.9% | 81.4% | Clear | 1.9 |
| 49 | 1 mg/ml | 94.5% | 13.0% | 81.5% | Clear | 1.0 |
| 37 | 1 mg/ml | 98.5% | 10.7% | 87.8% | Clear | 1.0 |

*normalized UV potency relative to T = 0
**normalized RP-HPLC puriy relative to T = 0
***UV potency − LC purity (total soluble − soluble degs)

Figure 1B:
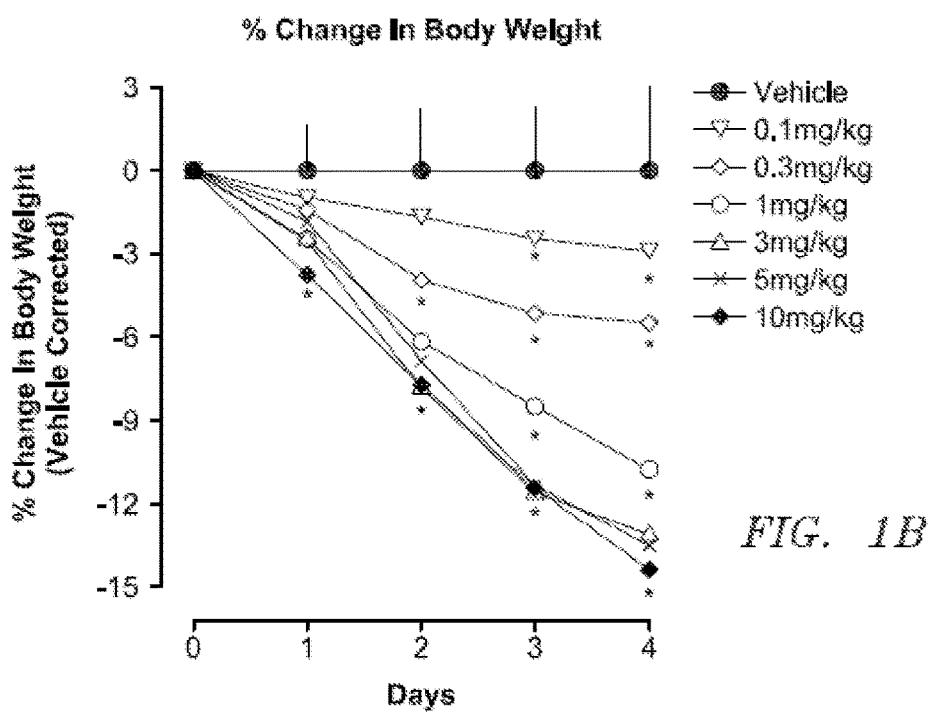

Example 4: Change in Body Weight After Daily Administration of Chimeric Polypeptide Method. C57BL6 female mice and their food were weighed daily 3 hours prior to lights out. Immediately after weighing, on days 0, 1, 2 and 3 mice were injected SC with leptin compound or mutant in 1×PBS. Points represent mean±sd of n=4 cages (3 mice/cage). Each group (n=12/group) was assigned to receive one of the following: vehicle; Cmpd 41 at 0.1 mg/kg; Cmpd 41 at 0.3 mg/kg; Cmpd 41 at 1 mg/kg; Cmpd 41 at 3 mg/kg; Cmpd 41 at 5 mg/kg; Cmpd 41 at 10 mg/kg. Food intake and change in body weight (% vehicle corrected) were monitored for 4 days, and the results recorded as shown (FIGS. 1A and 1B). Points represent mean±sd of n=4 cages (3 mice/cage). Administered compounds: Vehicle (filled circle); Cmpd 41 at 0.1 mg/kg (triangle tip down); Cmpd 41 at 0.3 mg/kg (open diamond); Cmpd 41 at 1 mg/kg (open circle); Cmpd 41 at 3 mg/kg (triangle tip up); Cmpd 41 at 5 mg/kg (star); Cmpd 41 at 10 mg/kg (filled diamond).

Figure 1C:
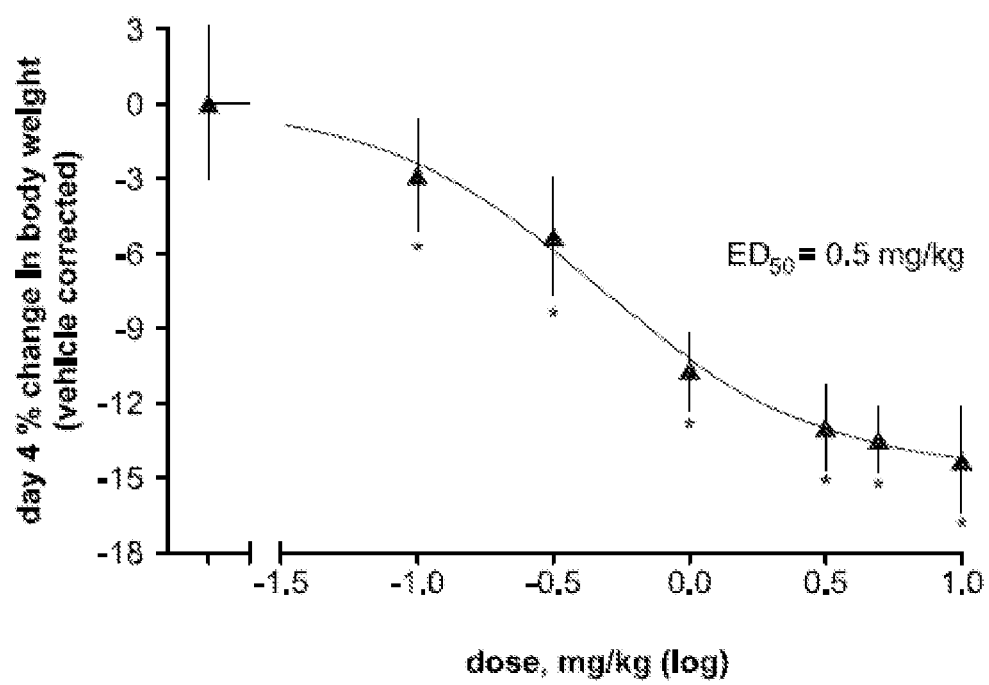

Results. As depicted in FIGS. 1A and 1B, administration of different doses of the chimeric polypeptide resulted in reduced food intake and body weight relative to the group that received vehicle alone. A dose response is observed in FIG. 1C.

Figure 2A:
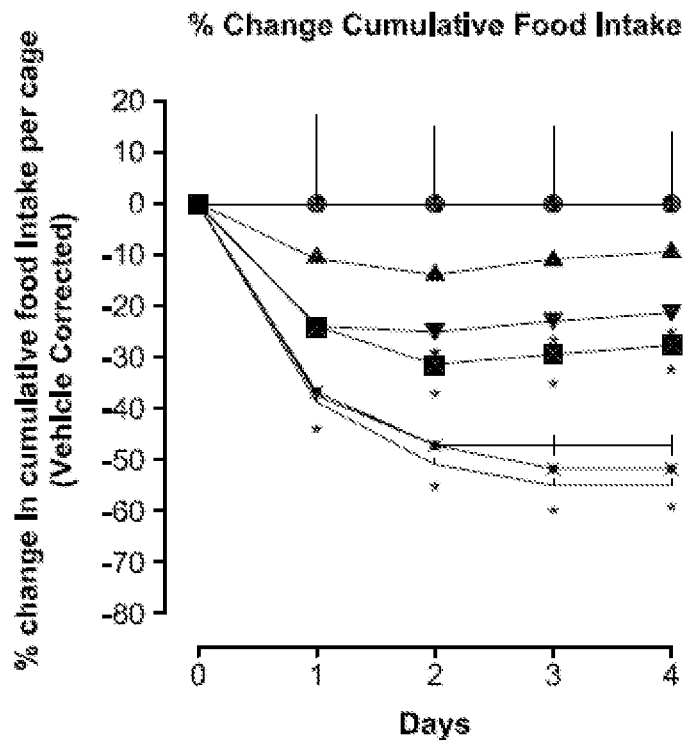
FIGS. 2A-2C depict the effects of a daily administration of the indicated chimeric polypeptides described herein on food intake and change in body weight (% vehicle-corrected) upon administration to C57/B6 female mice as described in Example 5.
Figure 2B:
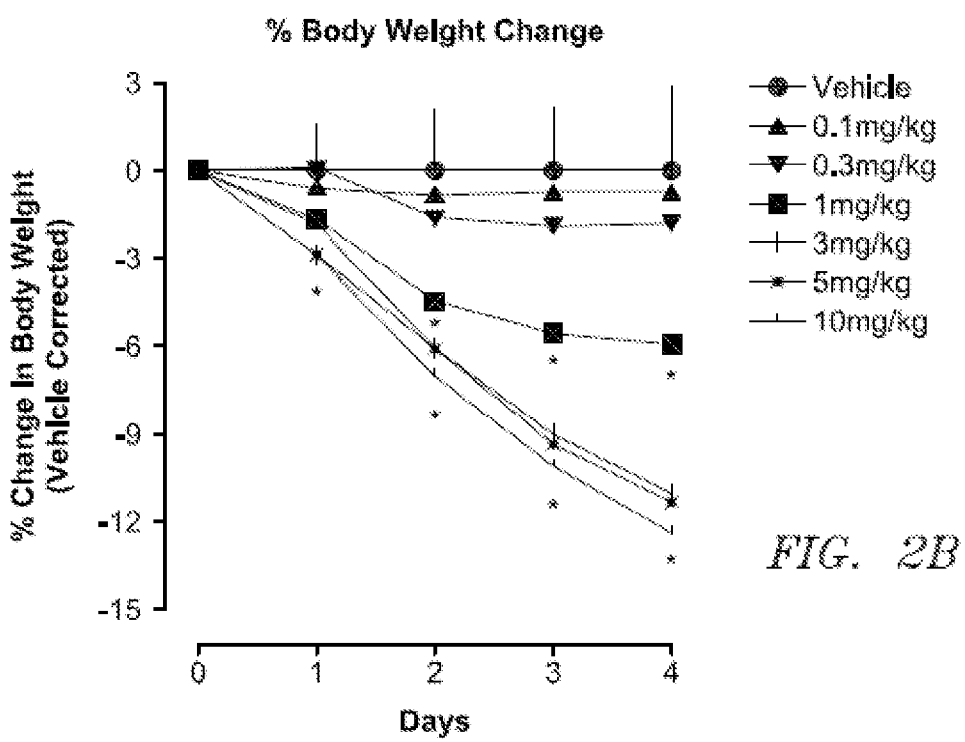

Example 5: Change in Body Weight After Daily Administration of Chimeric Polypeptide Method. C57BL6 female mice and their food were weighed daily 3 hours prior to lights out. Immediately after weighing, on days 0, 1, 2 and 3 mice were injected SC with leptin compound or mutant in 1×PBS. Points represent mean±sd of n=4 cages (3 mice/cage). Each group (n=12/group) was assigned to receive one of the following: vehicle; Cmpd 42 at 0.1 mg/kg; Cmpd 42 at 0.3 mg/kg; Cmpd 42 at 1 mg/kg; Cmpd 42 at 3 mg/kg; Cmpd 42 at 5 mg/kg; Cmpd 42 at 10 mg/kg. Food intake and change in body weight (% vehicle corrected) were monitored for 4 days, and the results recorded as shown (FIGS. 2A and 2B). Points represent mean±sd of n=4 cages (3 mice/cage). Administered compounds: Vehicle (filled circle); Cmpd 42 at 0.1 mg/kg (triangle tip up); Cmpd 42 at 0.3 mg/kg (triangle tip up); Cmpd 42 at 1 mg/kg (filled square); Cmpd 42 at 3 mg/kg (bar above and below point); Cmpd 42 at 5 mg/kg (star); Cmpd 42 at 10 mg/kg (bar above point).

Figure 2C:
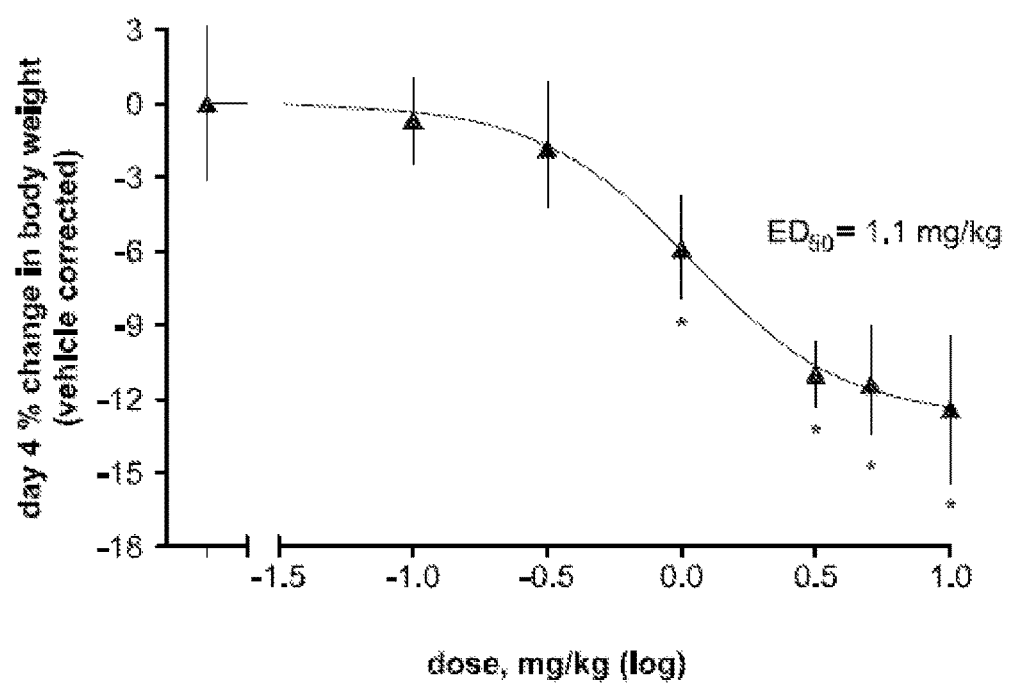

Results. As depicted in FIGS. 2A and 2B, administration of different doses of the chimeric polypeptide resulted in reduced food intake and body weight relative to the group that received vehicle alone. A dose response is observed in FIG. 2C.

As shown in Table 5 below, the dose responses measured for chimeric polypeptides of the invention are comparable to the dose responses measured for the seal leptin (Cmpd 38) and human leptin (Cmpd 37) from which the chimeric polypeptides are derived.

TABLE 5

Dose responses of chimeric polypeptides

| Compound | ED50 |
|---|---|
| 37 | 0.44-0.6 mg/kg |
| 38 | 0.8 mg/kg |
| 41 | 0.5 mg/kg |
| 42 | 1.1 mg/kg |

VIII. Embodiments

Additional embodiments of the chimeric polypeptides, method of use thereof, and pharmaceuticals compositions described herein follow:

Embodiment 1

A chimeric polypeptide comprising a wild type seal leptin polypeptide wherein at least one contiguous region of 1-30 amino acids of a wild type seal leptin sequence has been replaced with a contiguous region of 1-30 amino acids of a mature human leptin sequence.

Embodiment 2

The chimeric polypeptide according to Embodiment 1, wherein two or more contiguous regions of 1-30 amino acids of a wild type seal leptin sequence have been replaced at each region with a contiguous region of 1-30 amino acids of a mature human leptin sequence.

Embodiment 3

The chimeric polypeptide according to Embodiment 1 or 2, wherein a wild type seal leptin sequence comprises the amino acid sequence of SEQ ID NO:28 or SEQ ID NO:31.

Embodiment 4

The chimeric polypeptide according to any one of Embodiments 1-3, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51.

Embodiment 5

The chimeric polypeptide of any one of Embodiments 1-4, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least one amino acid substitution at a position where divergence is observed in a corresponding position in a leptin from another species.

Embodiment 6

The chimeric polypeptide of any one of Embodiments 1-5, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least two amino acid substitutions at positions where divergence is observed in corresponding positions in a leptin from another species.

Embodiment 7

The chimeric polypeptide of any one of Embodiments 1-6, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least three amino acid substitutions at positions where divergence is observed in corresponding positions in a leptin from another species.

Embodiment 8

The chimeric polypeptide of any one of Embodiments 1-7, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least four amino acid substitutions at positions where divergence is observed in corresponding positions in a leptin from another species.

Embodiment 9

The chimeric polypeptide of any one of Embodiments 1-8, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least five amino acid substitutions at positions where divergence is observed in corresponding positions in a leptin from another species.

Embodiment 10

The chimeric polypeptide of any one of Embodiments 1-9, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least six amino acid substitutions at positions where divergence is observed in corresponding positions in a leptin from another species.

Embodiment 11

The chimeric polypeptide of any one of Embodiments 1-10, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least seven amino acid substitutions at positions where divergence is observed in corresponding positions in a leptin from another species.

Embodiment 12

The chimeric polypeptide of any one of Embodiments 1-11, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least eight amino acid substitutions at positions where divergence is observed in corresponding positions in a leptin from another species.

Embodiment 13

The chimeric polypeptide of any one of Embodiments 1-12, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least nine amino acid substitutions at positions where divergence is observed in corresponding positions in a leptin from another species.

Embodiment 14

The chimeric polypeptide of any one of Embodiments 1-13, wherein a mature human leptin sequence comprises an amino acid sequence selected from the group consisting of: SEQ ID NO:12, SEQ ID NO:13, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51, wherein the mature human leptin sequence has at least ten amino acid substitutions at positions where divergence is observed in corresponding positions in a leptin from another species.

Embodiment 15

The chimeric polypeptide of any one of Embodiments 1-14, wherein the mature human leptin sequence comprises the amino acid sequence of SEQ ID NO:24.

Embodiment 16

The chimeric polypeptide of any one of Embodiments 1-15, wherein the chimeric polypeptide comprises an amino acid sequence with at least 80% identity with an amino acid sequence selected from the group consisting of: SEQ ID NO:29, SEQ ID NO:30, SEQ ID NO:32, SEQ ID NO:33, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, ID NO:81, SEQ ID NO:82, SEQ ID NO:83, SEQ ID NO:84, and SEQ ID NO:85.

Embodiment 17

The chimeric polypeptide of any one of Embodiments 1-16, wherein the chimeric polypeptide comprises an amino acid sequence with at least 80% identity with an amino acid sequence selected from the group consisting of: SEQ ID NO:29, SEQ ID NO:30, SEQ ID NO:32, SEQ ID NO:33.

Embodiment 18

The chimeric polypeptide of any one of Embodiments 1-17, wherein the chimeric polypeptide comprises an amino acid sequence with at least 80% identity the amino acid sequence of SEQ ID NO:33.

Embodiment 19

The chimeric polypeptide of any one of Embodiments 1-18, wherein the chimeric polypeptide comprises an amino acid sequence with at least 90% identity the amino acid sequence of SEQ ID NO:33.

Embodiment 20

The chimeric polypeptide of any one of Embodiments 1-19, wherein the chimeric polypeptide comprises an amino acid sequence selected from the group consisting of: SEQ ID NO:29, SEQ ID NO:30, SEQ ID NO:32, SEQ ID NO:33, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, ID NO:81, SEQ ID NO:82, SEQ ID NO:83, SEQ ID NO:84, and SEQ ID NO:85.

Embodiment 21

The chimeric polypeptide of any one of Embodiments 1-20, wherein the chimeric polypeptide comprises an amino acid sequence selected from the group consisting of: SEQ ID NO:29, SEQ ID NO:30, SEQ ID NO:32, SEQ ID NO:33.

Embodiment 22

The chimeric polypeptide of any one of Embodiments 1-21, wherein the chimeric polypeptide comprises the amino acid sequence of SEQ ID NO:29.

Embodiment 23

The chimeric polypeptide of any one of Embodiments 1-21, wherein the chimeric polypeptide comprises the amino acid sequence of SEQ ID NO:30.

Embodiment 24

The chimeric polypeptide of any one of Embodiments 1-21, wherein the chimeric polypeptide comprises the amino acid sequence of SEQ ID NO:32.

Embodiment 25

The chimeric polypeptide of any one of Embodiments 1-21, wherein the chimeric polypeptide comprises the amino acid sequence of SEQ ID NO:33.

Embodiment 26

A method for treating a disease or disorder in a subject, comprising administering a chimeric polypeptide of any one of Embodiments 1 to 25 to a subject in need thereof in an amount effective to treat said disease or disorder.

Embodiment 27

The method according to Embodiment 26, wherein the disease or disorder is disease or disorder is selected from the group consisting of: lipodystrophy, dyslipidemia, hyperlipidemia, overweight, obesity, hypothalamic amenorrhea, Alzheimer's disease, leptin deficiency, fatty liver disease, diabetes (including type I and type II), nonalcoholic steatohepatitis (NASH), nonalcoholic fatty liver disease (NAFLD), metabolic syndrome X and Huntington's Disease.

Embodiment 28

The method of Embodiment 26 or Embodiment 27, wherein the disease or disorder is lipodystrophy, dyslipidemia, hyperlipidemia, overweight, obesity, hypothalamic amenorrhea, Alzheimer's disease, leptin deficiency, fatty liver disease or diabetes.

Embodiment 29

The method of any one of Embodiments 26-28, wherein the disease or disorder is type I diabetes or type II diabetes.

Embodiment 30

The method of any one of Embodiments 26-28, wherein the disease or disorder is obesity

Embodiment 31

The method of any one of Embodiments 26-28, wherein the disease or disorder is lipodystrophy or leptin deficiency.

Embodiment 32

A pharmaceutical composition comprising a chimeric polypeptide according to any one of Embodiments 1-25 and a pharmaceutically acceptable excipient.

IX. Informal Sequence Listing

An informal listing of sequences disclosed herein follows:

```
                                                        (SEQ ID NO: 1)
VPIQKVQDDTKTLIKTIVTRINDISHT-Xaa-SVSSKQKVTGLDFIPGLHPILTLSKMDQTLA

VYQQILTSMPSRNVIQISNDLENLRDLLHVLAFSKSCHLPQASGLETLESLGGVLEAS

GYSTEVVALSRLQGSLQDMLQQLDLSPGC,
wherein Xaa at position 28 is Q or absent.

(SEQ ID NO: 2)
VPIQKVQDDTKTLIKTIVTRINDISHTQSVSAKQRVTGLDFIPGLHPILSLSKMDQTLAVY

QQVLTSLPSQNVLQIANDLENLRDLLHLLAFSKSCSLPQTSGLQKPESLDGVLEASLY

STEVVALSRLQGSLQDILQQLDVSPEC.

(SEQ ID NO: 3)
VPIQKVQDDTKTLIKTIVTRINDISHTSVSAKQRVTGLDFIPGLHPILSLSKMDQTLAVYQ

QVLTSLPSQNVLQIANDLENLRDLLHLLAFSKSCSLPQTSGLQKPESLDGVLEASLYS

TEVVALSRLQGSLQDILQQLDVSPEC.

(SEQ ID NO: 4)
MVPIQKVQDDTKTLIKTIVTRINDISHT-Xaa-SVSSKQKVTGLDFIPGLHPILTLSKMDQTL

AVYQQILTSMPSRNVIQISNDLENLRDLLHVLAFSKSCHLPQASGLETLESLGGVLEA

SGYSTEVVALSRLQGSLQDMLQQLDLSPGC,
wherein Xaa at position 29 is Q or absent.

(SEQ ID NO: 5)
MVPIQKVQDDTKTLIKTIVTRINDISHTQSVSAKQRVTGLDFIPGLHPILSLSKMDQTLAV

YQQVLTSLPSQNVLQIANDLENLRDLLHLLAFSKSCSLPQTSGLQKPESLDGVLEASL

YSTEVVALSRLQGSLQDILQQLDVSPEC.

(SEQ ID NO: 6)
MVPIQKVQDDTKTLIKTIVTRINDISHTSVSAKQRVTGLDFIPGLHPILSLSKMDQTLAVY

QQVLTSLPSQNVLQIANDLENLRDLLHLLAFSKSCSLPQTSGLQKPESLDGVLEASLY

STEVVALSRLQGSLQDILQQLDVSPEC.

(SEQ ID NO: 7)
VPIWRVQDDTKTLIKTIVTRISDISHMQSVSSKQRVTGLDFIPGLHPVLSLSKMDQTLAIY

QQILTSLPSRNVIQISNDLENLRDLLHLLASSKSCPLPQARALETLESLGGVLEASLYS

TEVVALSRLQGALQDMLRQLDLSPGC.
```

```
                                                              (SEQ ID NO: 8)
MVPIWRVQDDTKTLIKTIVTRISDISHMQSVSSKQRVTGLDFIPGLHPVLSLSKMDQTLAI

YQQILTSLPSRNVIQISNDLENLRDLLHLLASSKSCPLPQARALETLESLGGVLEASLY

STEVVALSRLQGALQDMLRQLDLSPGC.

(SEQ ID NO: 9)
VPICKVQDDTKTLIKTIVTRINDISHT-Xaa-SVSSKQRVTGLDFIPGLHPLLSLSKMDQTLAI

YQQILTSLPSRNVVQISNDLENLRDLLHLLAASKSCPLPQVRALESLESLGVVLEASL

YSTEVVALSRLQGSLQDMLRQLDLSPGC,
wherein Xaa at position 28 is Q or absent.

(SEQ ID NO: 10)
MVPICKVQDDTKTLIKTIVTRINDISHT-Xaa-SVSSKQRVTGLDFIPGLHPLLSLSKMDQTL

AIYQQILTSLPSRNVVQISNDLENLRDLLHLLAASKSCPLPQVRALESLESLGVVLEAS

LYSTEVVALSRLQGSLQDMLRQLDLSPGC,
wherein Xaa at position 29 is Q or absent.

(SEQ ID NO: 11)
MHWGTLCGFLWLWPYLFYVQAVPIQKVQDDTKTLIKTIVTRINDISHTQSVSSKQKVTG

LDFIPGLHPILTLSKMDQTLAVYQQILTSMPSRNVIQISNDLENLRDLLHVLAFSKSCH

LPWASGLETLDSLGGVLEASGYSTEVVALSRLQGSLQDMLWQLDLSPGC (SEQ ID NO: 12)
VPIQKVQDDTKTLIKTIVTRINDISH-Xaa-Xaa-SVSSKQKVTGLDFIPGLHPILTLSKMDQT

LAVYQQILTSMPSRNVIQISNDLENLRDLLHVLAFSKSCHLPWASGLETLDSLGGVLE

ASGYSTEVVALSRLQGSLQDMLWQLDLSPGC,
wherein: Xaa at position 27 is T or A;
and Xaa at position 28 is Q or absent.

(SEQ ID NO: 13)
MVPIQKVQDDTKTLIKTIVTRINDISH-Xaa-Xaa-SVSSKQKVTGLDFIPGLHPILTLSKMDQ

TLAVYQQILTSMPSRNVIQISNDLENLRDLLHVLAFSKSCHLPWASGLETLDSLGGVL

EASGYSTEVVALSRLQGSLQDMLWQLDLSPGC,
wherein: Xaa at position 28 is T or A;
and Xaa at position 29 is Q or absent.

(SEQ ID NO: 14)
VPIQKVQSDTKTLIKTIVTRINDISHTQSVSSKQRVTGLDFIPGLHPVLTLSQMDQTLAIYQ

QILINLPSRNVIQISNDLENLRDLLHLLAFSKSCHLPLASGLETLESLGDVLEASLYSTE

VVALSRLQGSLQDMLWQLDLSPGC.

(SEQ ID NO: 15)
MVPIQKVQSDTKTLIKTIVTRINDISHTQSVSSKQRVTGLDFIPGLHPVLTLSQMDQTLAI

YQQILINLPSRNVIQISNDLENLRDLLHLLAFSKSCHLPLASGLETLESLGDVLEASLY

STEVVALSRLQGSLQDMLWQLDLSPGC.

(SEQ ID NO: 16)
VPIHKVQDDTKTLIKTIVTRINDISHTQSVSARQRVTGLDFIPGLHPILSLSKMDQTLAVY

QQILTSLPSQNVLQIAHDLENLRDLLHLLAFSKSCSLPQTRGLQKPESLDGVLEASLY

STEVVALSRLQGSLQDILQQLDLSPEC.

(SEQ ID NO: 17)
MVPIHKVQDDTKTLIKTIVTRINDISHTQSVSARQRVTGLDFIPGLHPILSLSKMDQTLAV

YQQILTSLPSQNVLQIAHDLENLRDLLHLLAFSKSCSLPQTRGLQKPESLDGVLEASL

YSTEVVALSRLQGSLQDILQQLDLSPEC.
```

-continued (SEQ ID NO: 18)
ISIEKIQADTKTLTKTIITRIIQLSTQNGVSTDQRVSGLDFIPGNQQFQNLADMDQTLAVYQ
QILSSLPMPDRTQISNDLENLRSLFALLATLKNCPFTRSDGLDTMEIWGGIVEESLYST
EVVTLDRLRKSLKNIEKQLDHIQG.

(SEQ ID NO: 19)
MRCILLYGFLCVWQHLYYSHPISIEKIQADTKTLTKTIITRIIQLSTQNGVSTDQRVSGLDF
IPGNQQFQNLADMDQTLAVYQQILSSLPMPDRTQISNDLENLRSLFALLATLKNCPFT
RSDGLDTMEIWGGIVEESLYSTEVVTLDRLRKSLKNIEKQLDHIQG.

(SEQ ID NO: 20)
VPIQKVQDDTKTLIKTIVTRINDISHTQSVSSKQKVTGLDFIPGLHPILTLSKMDQTLAVY
QQILTSMPSRNVIQISNDLENLRDLLHVLAFSKSCHLPWASGLETLDSLGGVLEASGY
STEVVALSRLQGSLQDMLWQLDLSPGC.

(SEQ ID NO: 21)
VPIQKVQDDTKTLIKTIVTRINDISHAQSVSSKQKVTGLDFIPGLHPILTLSKMDQTLAVY
QQILTSMPSRNVIQISNDLENLRDLLHVLAFSKSCHLPWASGLETLDSLGGVLEASG
YSTEVVALSRLQGSLQDMLWQLDLSPGC.

(SEQ ID NO: 22)
VPIQKVQDDTKTLIKTIVTRINDISHTSVSSKQKVTGLDFIPGLHPILTLSKMDQTLAVYQ
QILTSMPSRNVIQISNDLENLRDLLHVLAFSKSCHLPWASGLETLDSLGGVLEASGYS
TEVVALSRLQGSLQDMLWQLDLSPGC.

(SEQ ID NO: 23)
VPIQKVQDDTKTLIKTIVTRINDISHASVSSKQKVTGLDFIPGLHPILTLSKMDQTLAVYQ
QILTSMPSRNVIQISNDLENLRDLLHVLAFSKSCHLPWASGLETLDSLGGVLEASGYS
TEVVALSRLQGSLQDMLWQLDLSPGC.

(SEQ ID NO: 24)
MVPIQKVQDDTKTLIKTIVTRINDISHTQSVSSKQKVTGLDFIPGLHPILTLSKMDQTLAV
YQQILTSMPSRNVIQISNDLENLRDLLHVLAFSKSCHLPWASGLETLDSLGGVLEASG
YSTEVVALSRLQGSLQDMLWQLDLSPGC.

(SEQ ID NO: 25)
MVPIQKVQDDTKTLIKTIVTRINDISHAQSVSSKQKVTGLDFIPGLHPILTLSKMDQTLAV
YQQILTSMPSRNVIQISNDLENLRDLLHVLAFSKSCHLPWASGLETLDSLGGVLEASG
YSTEVVALSRLQGSLQDMLWQLDLSPGC.

(SEQ ID NO: 26)
MVPIQKVQDDTKTLIKTIVTRINDISHTSVSSKQKVTGLDFIPGLHPILTLSKMDQTLAVY
QQILTSMPSRNVIQISNDLENLRDLLHVLAFSKSCHLPWASGLETLDSLGGVLEASGY
STEVVALSRLQGSLQDMLWQLDLSPGC.

(SEQ ID NO: 27)
MVPIQKVQDDTKTLIKTIVTRINDISHASVSSKQKVTGLDFIPGLHPILTLSKMDQTLAVY
QQILTSMPSRNVIQISNDLENLRDLLHVLAFSKSCHLPWASGLETLDSLGGVLEASGY
STEVVALSRLQGSLQDMLWQLDLSPGC.

(SEQ ID NO: 28)
PIQRVQDDTKTLIKTIITRINDISPPQGVCSRPRVAGLDFIPRVQSVRTLSGMDQILATYQQ
ILTSLQSRSVVQIANDLANLRALLRLLASAKSCPVPRARGSDTIKGLGNVLRASVHST
EVVALSRLKAALQDMLRQLDRNPGC.

```
                                             (SEQ ID NO: 29)
PIQRVQDDTKTLIKTIITRINDISPPQGVCSRPRVAGLDFIPRVQSVRTLSGMDQILATYQQ

ILTSLQSRNVIQISNDLENLRDLLHVLAFSKSCPVPRARGSDTIKGLGNVLRASVHSTE

VVALSRLKAALQDMLRQLDRNPGC.

(SEQ ID NO: 30)
PIQRVQDDTKTLIKTIITRINDISPPQGVSSRPRVAGLDFIPRVQSVRTLSGMDQILATYQQI

LTSLQSRNVIQISNDLENLRDLLHVLAFSKSCPVPRARGSDTIKGLGNVLRASVHSTE

VVALSRLKAALQDMLRQLDRNPGC.

(SEQ ID NO: 31)
MPIQRVQDDTKTLIKTIITRINDISPPQGVCSRPRVAGLDFIPRVQSVRTLSGMDQILATYQ

QILTSLQSRSVVQIANDLANLRALLRLLASAKSCPVPRARGSDTIKGLGNVLRASVHS

TEVVALSRLKAALQDMLRQLDRNPGC.

(SEQ ID NO: 32)
MPIQRVQDDTKTLIKTIITRINDISPPQGVCSRPRVAGLDFIPRVQSVRTLSGMDQILATYQ

QILTSLQSRNVIQISNDLENLRDLLHVLAFSKSCPVPRARGSDTIKGLGNVLRASVHST

EVVALSRLKAALQDMLRQLDRNPGC.

(SEQ ID NO: 33)
MPIQRVQDDTKTLIKTIITRINDISPPQGVSSRPRVAGLDFIPRVQSVRTLSGMDQILATYQ

QILTSLQSRNVIQISNDLENLRDLLHVLAFSKSCPVPRARGSDTIKGLGNVLRASVHST

EVVALSRLKAALQDMLRQLDRNPGC.

(SEQ ID NO: 34)
MDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG

KVPIQKVQDDTKTLIKTIVTRINDISHTQSVSSKQKVTGLDFIPGLHPILTLSKMDQTL

AVYQQILTSMPSRNVIQISNDLENLRDLLHVLAFSKSCHLPWASGLETLDSLGGVLEA

SGYSTEVVALSRLQGSLQDMLWQLDLSPGC (SEQ ID NO: 35)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGGVLEASG

YSTEVVALSRLQGSLQDMLQQLDLSPGC.

(SEQ ID NO: 36)
MVPIQKVQDDTKTLIKTIVTRINDISHTQSVSSKQKVTGLDFIPGLHPILTLSKMDQTLAV

YQQILTSMPSRNVIQICNDLENLRDLLHVLAFSKSCHLPWASGLETLDSLGGVLEASG

YSTEVVALSRLQGSLQDMLWQLDLSPGC.

(SEQ ID NO: 37)
MVPIQKVQDDTKTLIKTIVTRINDISHTQSVSSKQKVTGLEFIPGLHPILTLSKMDQTLAV

YQQILTSMPSRNVIQISNDLENLRDLLHVLAFSKSCHLPQASGLETLESLGGVLEASG

YSTEVVALSRLQGSLQDMLQQLDLSPGC.

(SEQ ID NO: 38)
MVPIQKVQDDTKTLIKTIVTRINDISHTQSVSSKQKVTGLEFIPGLHPILTLSKMDQTLAV

YQQILTSMPSRNVIQISNDLENLRDLLHVLAFSKSCSLPQASGLETLESLGEVLEASGY

STEVVALSRLQGSLQDILQQLDLSPEC.
```

-continued

```
                                                        (SEQ ID NO: 39)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQASGLETLDSLGGVLEASG

YSTEVVALSRLQGSLQDILQQLDLSPEC.

(SEQ ID NO: 40)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQASGLETLDSLGEVLEASG

YSTEVVALSRLQGSLQDILQQLDLSPEC.

(SEQ ID NO: 41)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGEVLEASG

YSTEVVALSRLQGSLQDILQQLDLSPEC.

(SEQ ID NO: 42)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQASGLETLDSLGGVLEASG

YSTEVVALSRLQGSLQDILQQLDLSPEC.

(SEQ ID NO: 43)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGEVLEASG

YSTEVVALSRLQGSLQDILQQLDVSPEC.

(SEQ ID NO: 44)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQTSGLETLDSLGGVLEASG

YSTEVVALSRLQGSLQDILQQLDLSPEC.

(SEQ ID NO: 45)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQASGLETLESLGEVLEASGY

STEVVALSRLQGSLQDMLWQLDLSPEC.

(SEQ ID NO: 46)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGGVLEASG

YSTEVVALSRLQGSLQDILQQLDLSPEC.

(SEQ ID NO: 47)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGGVLEASG

YSTEVVALSRLQGSLQDILQQLDVSPEC.

(SEQ ID NO: 48)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQTSGLETLDSLGGVLEASG

YSTEVVALSRLQGSLQDILQQLDVSPEC.

(SEQ ID NO: 49)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCSLPQTSGLETLDSLGEVLEASGY

STEVVALSRLQGSLQDMLWQLDLSPEC.
```

```
                                          (SEQ ID NO: 50)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGEVLEASG

YSTEVVALSRLQGSLQDMLQQLDLSPGC.

(SEQ ID NO: 51)
MVPIQKVQDDTKTLIKTIVTRINDISHTQSVSSKQKVTGLDFIPGLHPILTLSKMDQTLAV

YQQILTSMPSRNVIQISNDLENLRDLLHVLAFSKSCHLPQASGLETLDSLGEVLEASG

YSTEVVALSRLQGSLQDMLQQLDLSPEC.

(SEQ ID NO: 52)
PIQKVQDDTKTLIKTIVTRINDISPPQGVCSRPRVAGLDFIPRVQSVRTLSGMDQILATYQ

QILTSLQSRSVVQIANDLANLRALLRLLASAKSCPVPRARGSDTIKGLGNVLRASVHS

TEVVALSRLKAALQDMLRQLDRNPGC.

(SEQ ID NO: 53)
MPIQKVQDDTKTLIKTIVTRINDISPPQGVCSRPRVAGLDFIPRVQSVRTLSGMDQILATY

QQILTSLQSRSVVQIANDLANLRALLRLLASAKSCPVPRARGSDTIKGLGNVLRASV

HSTEVVALSRLKAALQDMLRQLDRNPGC.

(SEQ ID NO: 54)
PIQRVQDDTKTLIKTIITRINDISPPQGVCSRPRVAGLDFIPRVQSVRTLSKMDQTLAVYQ

QILTSLQSRSVVQIANDLANLRALLRLLASAKSCPVPRARGSDTIKGLGNVLRASVHS

TEVVALSRLKAALQDMLRQLDRNPGC.

(SEQ ID NO: 55)
MPIQRVQDDTKTLIKTIITRINDISPPQGVCSRPRVAGLDFIPRVQSVRTLSKMDQTLAVY

QQILTSLQSRSVVQIANDLANLRALLRLLASAKSCPVPRARGSDTIKGLGNVLRASV

HSTEVVALSRLKAALQDMLRQLDRNPGC.

(SEQ ID NO: 56)
PIQRVQDDTKTLIKTIITRINDISPPQGVCSRPRVAGLDFIPRVQSVRTLSGMDQILATYQQ

ILTSLQSRSVVQIANDLANLRALLRLLASAKSCPVPRARGSDTIKGLGNVLRASVHST

EVVALSRLQGSLQDMLWQLDLNPGC.

(SEQ ID NO: 57)
MPIQRVQDDTKTLIKTIITRINDISPPQGVCSRPRVAGLDFIPRVQSVRTLSGMDQILATYQ

QILTSLQSRSVVQIANDLANLRALLRLLASAKSCPVPRARGSDTIKGLGNVLRASVHS

TEVVALSRLQGSLQDMLWQLDLNPGC.

(SEQ ID NO: 58)
PIQRVQDDTKTLIKTIITRINDISHTQSVSSKQKVTGLDFIPGLHPILTLSGMDQILATYQQI

LTSLQSRSVVQIANDLANLRALLRLLASAKSCPVPRARGSDTIKGLGNVLRASVHST

EVVALSRLKAALQDMLRQLDRNPGC.

(SEQ ID NO: 59)
MPIQRVQDDTKTLIKTIITRINDISHTQSVSSKQKVTGLDFIPGLHPILTLSGMDQILATYQ

QILTSLQSRSVVQIANDLANLRALLRLLASAKSCPVPRARGSDTIKGLGNVLRASVHS

TEVVALSRLKAALQDMLRQLDRNPGC.

(SEQ ID NO: 60)
PIQRVQDDTKTLIKTIITRINDISPPQGVCSRPRVAGLDFIPRVQSVRTLSGMDQILATYQQ

ILTSLQSRSVVQIANDLANLRALLRLLASAKSCHLPWASGLETLDSLGGVLEASGYST

EVVALSRLKAALQDMLRQLDRNPGC.
```

-continued (SEQ ID NO: 61)
MPIQRVQDDTKTLIKTIITRINDISPPQGVCSRPRVAGLDFIPRVQSVRTLSGMDQILATYQ

QILTSLQSRSVVQIANDLANLRALLRLLASAKSCHLPWASGLETLDSLGGVLEASGY

STEVVALSRLKAALQDMLRQLDRNPGC.

(SEQ ID NO: 62)
PIQKVQDDTKTLIKTIVTRINDISPPQGVCSRPRVAGLDFIPRVQSVRTLSGMDQILATYQ

QILTSLQSRNVIQISNDLENLRDLLHVLAFSKSCPVPRARGSDTIKGLGNVLRASVHST

EVVALSRLKAALQDMLRQLDRNPGC (SEQ ID NO: 63)
MPIQKVQDDTKTLIKTIVTRINDISPPQGVCSRPRVAGLDFIPRVQSVRTLSGMDQILATY

QQILTSLQSRNVIQISNDLENLRDLLHVLAFSKSCPVPRARGSDTIKGLGNVLRASVH

STEVVALSRLKAALQDMLRQLDRNPGC (SEQ ID NO: 64)
PIQRVQDDTKTLIKTIITRINDISHTQSVSSKQKVTGLDFIPGLHPILTLSGMDQILATYQQI

LTSLQSRNVIQISNDLENLRDLLHVLAFSKSCPVPRARGSDTIKGLGNVLRASVHSTE

VVALSRLKAALQDMLRQLDRNPGC (SEQ ID NO: 65)
MPIQRVQDDTKTLIKTIITRINDISHTQSVSSKQKVTGLDFIPGLHPILTLSGMDQILATYQ

QILTSLQSRNVIQISNDLENLRDLLHVLAFSKSCPVPRARGSDTIKGLGNVLRASVHST

EVVALSRLKAALQDMLRQLDRNPGC (SEQ ID NO: 66)
PIQRVQDDTKTLIKTIITRINDISPPQGVCSRPRVAGLDFIPRVQSVRTLSGMDQILATYQQ

ILTSLQSRNVIQISNDLENLRDLLHVLAFSKSCHLPWASGLETLDSLGGVLEASGYST

EVVALSRLKAALQDMLRQLDRNPGC (SEQ ID NO: 67)
MPIQRVQDDTKTLIKTIITRINDISPPQGVCSRPRVAGLDFIPRVQSVRTLSGMDQILATYQ

QILTSLQSRNVIQISNDLENLRDLLHVLAFSKSCHLPWASGLETLDSLGGVLEASGYS

TEVVALSRLKAALQDMLRQLDRNPGC (SEQ ID NO: 68)
PIQRVQDDTKTLIKTIITRINDISHTQSVSSKQKVTGLDFIPGLHPILTLSGMDQILATYQQI

LTSLQSRSVVQIANDLANLRALLRLLASAKSCPVPRARGSDTIKGLGNVLRASVHST

EVVALSRLQGSLQDMLWQLDLNPGC (SEQ ID NO: 69)
MPIQRVQDDTKTLIKTIITRINDISHTQSVSSKQKVTGLDFIPGLHPILTLSGMDQILATYQ

QILTSLQSRSVVQIANDLANLRALLRLLASAKSCPVPRARGSDTIKGLGNVLRASVHS

TEVVALSRLQGSLQDMLWQLDLNPGC (SEQ ID NO: 70)
PIQRVQDDTKTLIKTIITRINDISHTQSVSSKQKVTGLDFIPGLHPILTLSGMDQILATYQQI

LTSLQSRSVVQIANDLANLRALLRLLASAKSCHLPWASGLETLDSLGGVLEASGYST

EVVALSRLKAALQDMLRQLDRNPGC (SEQ ID NO: 71)
MPIQRVQDDTKTLIKTIITRINDISHTQSVSSKQKVTGLDFIPGLHPILTLSGMDQILATYQ

QILTSLQSRSVVQIANDLANLRALLRLLASAKSCHLPWASGLETLDSLGGVLEASGY

STEVVALSRLKAALQDMLRQLDRNPGC

-continued (SEQ ID NO: 72)
PIQRVQDDTKTLIKTIITRINDISHTQSVSSKQKVTGLDFIPGLHPILTLSGMDQILATYQQI

LTSLQSRNVIQISNDLENLRDLLHVLAFSKSCHLPWASGLETLDSLGGVLEASGYSTE

VVALSRLKAALQDMLRQLDRNPGC (SEQ ID NO: 73)
MPIQRVQDDTKTLIKTIITRINDISHTQSVSSKQKVTGLDFIPGLHPILTLSGMDQILATYQ

QILTSLQSRNVIQISNDLENLRDLLHVLAFSKSCHLPWASGLETLDSLGGVLEASGYS

TEVVALSRLKAALQDMLRQLDRNPGC.

(SEQ ID NO: 74)
PIQKVQDDTKTLIKTIVTRINDISPPQGVSSRPRVAGLDFIPRVQSVRTLSGMDQILATYQ

QILTSLQSRSVVQIANDLANLRALLRLLASAKSCPVPRARGSDTIKGLGNVLRASVHS

TEVVALSRLKAALQDMLRQLDRNPGC.

(SEQ ID NO: 75)
MPIQKVQDDTKTLIKTIVTRINDISPPQGVSSRPRVAGLDFIPRVQSVRTLSGMDQILATY

QQILTSLQSRSVVQIANDLANLRALLRLLASAKSCPVPRARGSDTIKGLGNVLRASV

HSTEVVALSRLKAALQDMLRQLDRNPGC.

(SEQ ID NO: 76)
PIQRVQDDTKTLIKTIITRINDISPPQGVSSRPRVAGLDFIPRVQSVRTLSKMDQTLAVYQQ

ILTSLQSRSVVQIANDLANLRALLRLLASAKSCPVPRARGSDTIKGLGNVLRASVHST

EVVALSRLKAALQDMLRQLDRNPGC.

(SEQ ID NO: 77)
MPIQRVQDDTKTLIKTIITRINDISPPQGVSSRPRVAGLDFIPRVQSVRTLSKMDQTLAVY

QQILTSLQSRSVVQIANDLANLRALLRLLASAKSCPVPRARGSDTIKGLGNVLRASV

HSTEVVALSRLKAALQDMLRQLDRNPGC.

(SEQ ID NO: 78)
PIQRVQDDTKTLIKTIITRINDISPPQGVSSRPRVAGLDFIPRVQSVRTLSGMDQILATYQQI

LTSLQSRSVVQIANDLANLRALLRLLASAKSCPVPRARGSDTIKGLGNVLRASVHST

EVVALSRLQGSLQDMLWQLDLNPGC.

(SEQ ID NO: 79)
MPIQRVQDDTKTLIKTIITRINDISPPQGVSSRPRVAGLDFIPRVQSVRTLSGMDQILATYQ

QILTSLQSRSVVQIANDLANLRALLRLLASAKSCPVPRARGSDTIKGLGNVLRASVHS

TEVVALSRLQGSLQDMLWQLDLNPGC.

(SEQ ID NO: 80)
PIQRVQDDTKTLIKTIITRINDISPPQGVSSRPRVAGLDFIPRVQSVRTLSGMDQILATYQQI

LTSLQSRSVVQIANDLANLRALLRLLASAKSCHLPWASGLETLDSLGGVLEASGYST

EVVALSRLKAALQDMLRQLDRNPGC.

(SEQ ID NO: 81)
MPIQRVQDDTKTLIKTIITRINDISPPQGVSSRPRVAGLDFIPRVQSVRTLSGMDQILATYQ

QILTSLQSRSVVQIANDLANLRALLRLLASAKSCHLPWASGLETLDSLGGVLEASGY

STEVVALSRLKAALQDMLRQLDRNPGC.

(SEQ ID NO: 82)
PIQKVQDDTKTLIKTIVTRINDISPPQGVSSRPRVAGLDFIPRVQSVRTLSGMDQILATYQ

QILTSLQSRNVIQISNDLENLRDLLHVLAFSKSCPVPRARGSDTIKGLGNVLRASVHST

EVVALSRLKAALQDMLRQLDRNPGC

-continued

```
                                                  (SEQ ID NO: 83)
MPIQKVQDDTKTLIKTIVTRINDISPPQGVSSRPRVAGLDFIPRVQSVRTLSGMDQILATY

QQILTSLQSRNVIQISNDLENLRDLLHVLAFSKSCPVPRARGSDTIKGLGNVLRASVH

STEVVALSRLKAALQDMLRQLDRNPGC (SEQ ID NO: 84)
PIQRVQDDTKTLIKTIITRINDISPPQGVSSRPRVAGLDFIPRVQSVRTLSGMDQILATYQQI

LTSLQSRNVIQISNDLENLRDLLHVLAFSKSCHLPWASGLETLDSLGGVLEASGYSTE

VVALSRLKAALQDMLRQLDRNPGC (SEQ ID NO: 85)
MPIQRVQDDTKTLIKTIITRINDISPPQGVSSRPRVAGLDFIPRVQSVRTLSGMDQILATYQ

QILTSLQSRNVIQISNDLENLRDLLHVLAFSKSCHLPWASGLETLDSLGGVLEASGYS

TEVVALSRLKAALQDMLRQLDRNPGC (SEQ ID NO: 86)
KCNTATCATQRLANFLVRSSNNLGPVLPPTNVGSNTY;

(SEQ ID NO: 87)
KCNTATCATQRLANFLVHSSNNFGAILSSTNVGSNTY;

(SEQ ID NO: 88)
KCNTATCATQRLANFLVHSSNNFGPILPPTNVGSNTY.

(SEQ ID NO: 89)
CGNLSTCMLGTYTQDFNKFHTFPQTAIGVGAP;

(SEQ ID NO: 90)
CSNLSTCVLGKLSQELHKLQTYPRTNTGSGTP;

(SEQ ID NO: 91)
KCNTATCVLGRLSQELHRLQTYPRTNTGSNTY.
```

$$X'-Xaa^1-Cys^2-Asn^3-Thr^4-Ala^5-Thr^6-Cys^7-Ala^8-Thr^9-Gln^{10}-Arg^{11}-Leu^{12}-Ala^{13}-Asn^{14}-Phe^{15}-Leu^{16}-Val^{17}-His^{18}-Ser^{19}-Ser^{20}-Xaa^{21}-Asn^{22}-Phe^{23}-Xaa^{24}-Xaa^{25}-Xaa^{26}-Xaa^{27}-Xaa^{28}-Xaa^{29}-Thr^{30}-Xaa^{31}-Val^{32}-Gly^{33}-Ser^{34}-Asn^{35}-Thr^{36}-Tyr^{37}-X$$

(SEQ ID NO: 92)

```
                                                  (SEQ ID NO: 93)
CNTATCATQRLANFLVRSSNNLGPVLPPTNVGSNTY-NH2

(SEQ ID NO: 94)
KCNTATCATQRLANFLVRSSKNLGPVLPPTNVGSNTY-NH2

(SEQ ID NO: 95)
CNTATCATQRLANFLVRSSKNLGPVLPPTNVGSNTY-NH2

(SEQ ID NO: 96)
KCNTATCATQRLANFLVRSSNNLGPKLPPTNVGSNTY-NH2

(SEQ ID NO: 97)
CNTATCATQRLANFLVRSSNNLGPKLPPTNVGSNTY-NH2

(SEQ ID NO: 98)
KCNTATCATQRLANFLVRSSNNLGPVLPPTKVGSNTY-NH2

(SEQ ID NO: 99)
CNTATCATQRLANFLVRSSNNLGPVLPPTKVGSNTY-NH2

(SEQ ID NO: 100)
KCNTATCATQRLANFLVHSSNNFGPILPPTNVGSNTY-NH2

(SEQ ID NO: 101)
CNTATCATQRLANFLVHSSNNFGPILPPTNVGSNTY-NH2

(SEQ ID NO: 102)
CNTATCATQRLANFLVHSSKNFGPILPPTNVGSNTY-NH2

(SEQ ID NO: 103)
CNTATCATQRLANFLVHSSNNFGPKLPPTNVGSNTY-NH2

(SEQ ID NO: 104)
CNTATCATQRLANFLVHSSNNFGPILPPTKVGSNTY-NH2
```

-continued

```
                                                            (SEQ ID NO: 105)
CNTATCATQRLANFLVHSSNNFKPILPPTNVGSNTY-NH2

(SEQ ID NO: 106)
CNTATCATQRLANFLVHSSNNFGKILPPTNVGSNTY-NH2

(SEQ ID NO: 107)
CNTATCATQRLANFLVHSSNNFGPIKPPTNVGSNTY-NH2

(SEQ ID NO: 108)
CNTATCATQRLANFLVHSSNNFGPILKPTNVGSNTY-NH2

(SEQ ID NO: 109)
CNTATCATQRLANFLVHSSNNFGPILPKTNVGSNTY-NH2
```

---

The invention claimed is:

1. A chimeric polypeptide comprising a wild type seal leptin polypeptide wherein at least one contiguous region of 1-30 amino acids of a wild type seal leptin sequence has been replaced with a contiguous region of 1-30 amino acids of a mature human leptin sequence, and wherein the chimeric polypeptide comprises an amino acid sequence having at least 95% identity to the amino acid sequence of SEQ ID NO: 30.

2. The chimeric polypeptide of claim 1, wherein the chimeric polypeptide comprises an amino acid sequence having at least 98% identity to the amino acid sequence SEQ ID NO: 30.

3. The chimeric polypeptide of claim 1, wherein the chimeric polypeptide comprises the amino acid sequence SEQ ID NO: 30.

4. The chimeric polypeptide of claim 1, wherein the chimeric polypeptide comprises the amino acid sequence SEQ ID NO 32.

5. The chimeric polypeptide of claim 1, wherein the chimeric polypeptide comprises the amino acid sequence SEQ ID NO:33.

6. A method for treating a disease or disorder in a subject, comprising administering a chimeric polypeptide of claim 1 to a subject in need thereof in an amount effective to treat said disease or disorder, wherein the disease or disorder is selected from the group consisting of: overweight, obesity, overweight, obesity, lipodystrophy, dyslipidemia, hyperlipidemia, hypothalamic amenorrhea, Alzheimer's disease, leptin deficiency, fatty liver disease, diabetes (including type I and type II), nonalcoholic steatohepatitis (NASH), nonalcoholic fatty liver disease (NAFLD), metabolic syndrome X, and Huntington's Disease.

7. A pharmaceutical composition comprising a chimeric polypeptide according to claim 1 and a pharmaceutically acceptable excipient.

* * * * *